United States Patent
Chan et al.

(10) Patent No.: US 10,087,416 B2
(45) Date of Patent: Oct. 2, 2018

(54) CULTURING PLURIPOTENT STEM CELLS

(71) Applicant: Agency for Science, Technology and Research, Singapore (SG)

(72) Inventors: Yun Shen Chan, Singapore (SG); Huck Hui Ng, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 15/031,614

(22) PCT Filed: Oct. 27, 2014

(86) PCT No.: PCT/SG2014/000504
§ 371 (c)(1),
(2) Date: Apr. 22, 2016

(87) PCT Pub. No.: WO2015/060790
PCT Pub. Date: Apr. 30, 2015

(65) Prior Publication Data
US 2016/0319240 A1    Nov. 3, 2016

(30) Foreign Application Priority Data
Oct. 25, 2013 (SG) .............................. 201307979-3

(51) Int. Cl.
*C12N 5/0735* (2010.01)

(52) U.S. Cl.
CPC ...... *C12N 5/0606* (2013.01); *C12N 2501/155* (2013.01); *C12N 2501/235* (2013.01); *C12N 2501/724* (2013.01); *C12N 2501/727* (2013.01); *C12N 2501/999* (2013.01); *C12N 2533/90* (2013.01)

(58) Field of Classification Search
None
See application file for complete search history.

(56) References Cited

FOREIGN PATENT DOCUMENTS

| WO | WO-2007/113505 A2 | 10/2007 |
|---|---|---|
| WO | WO-2009/101407 A2 | 8/2009 |
| WO | WO-2011/082038 A2 | 7/2011 |

OTHER PUBLICATIONS

Hao, Jijun; et al; "Recent Progress on Chemical Biology of Pluripotent Stem Cell Self-renewal, Reprogramming and Cardiomyogenesis" Recent Patents in Regenerative Medicine, 1, 263-274, 2011 (Year: 2011).*
Silva, Jose; et al; "Promotion of Reprogramming to Ground State Pluripotency by Signal Inhibition" PLoS Biology, 6, 2237-2247, 2008 (Year: 2008).*
Yeo, J-C. et al, The transcriptional regulation of pluripotency, Cell Research, 23(1): 20-32 (2012).
Acampora, D. et al., Otx2 is an intrinsic determinant of the embryonic stem cell state and is required for transition to a stable epiblast stem cell condition, Development and Stem Cells, 140:43-55 (2013).
Chan, Y.S. et al., Induction of a human pluripotent state with distinct regulatory circuitry that resembles preimplantation epiblast, Cell Stem Cell, 13:663-675 (2013).
Frank, S. et al., Small molecule-assisted, line-independent maintenance of human pluripotent stem cells in defined conditions, PLoS One, 7(7): e41958, (2012).
Hanna, J. et al., Human embryonic stem cells with biological and epigenetic characteristics similar to those of mouse ESCs, PNAS, 107(20):9222-9227 (2010).
Harris, D. et al., Inhibition of MAP2K and GSK3 signaling promotes bovine blastocyst development and epiblast-associated expression of pluripotency factors, Biology of Reproduction, 88(3):74, 1-10 (2013).
Hassani, S.N. et al., Inhibition of TGFβ signaling promotes ground state pluripotency, Stem Cell Rev and Rep, 10:16-30 (2014).
International Search Report for PCT/SG2014/000504, 3 pages (dated Dec. 23, 2014).
Na, J. et al., Inhibition of ERK 1/2 prevents neural and mesendodermal differentiation and promotes human embryonic stem cell self-renewal, Stem Cell Research, 5:157-169 (2010).
Written Opinion for PCT/SG2014/000504, 7 pages (dated Dec. 23, 2014).

* cited by examiner

*Primary Examiner* — David W Berke-Schlessel
(74) *Attorney, Agent, or Firm* — Choate, Hall & Stewart LLP

(57) ABSTRACT

A method for culturing and maintaining a pluripotent stem cell in an undifferentiated state is provided. The method comprises culturing the pluripotent stem cell in a medium comprising an MEK inhibitor, a GSK3 inhibitor, a dual inhibitor of AMPK and/or BMP signaling and LIF. A cell produced by the method, cell culture medium and a kit for performing the method described is also provided.

10 Claims, 66 Drawing Sheets

| List of small molecules compounds | |
|---|---|
| Small molecules | Target pathway |
| PD0325901 (PD03) | MAPK/ERK |
| BIO | Wnt/β catenin |
| ChIR99021 (CHIR) | Wnt/β catenin |
| RepSox (SOX) | Activin/TGFβ |
| A83-01 (A83) | Activin/TGFβ |
| IDE-1 | Activin/TGFβ |
| Pifithrin-α (PFTα) | P53 |
| Forskolin (FOR) | PKA |
| PD173074 (PD17) | FGF |
| Dorsomorphin (DOR) | BMP |
| PD153035 (PD15) | EGF |

F

E

F

G

H

E

F

G

H

A

B

E

F

G

H

I

J

O

P

R

C

A

B

J

K

CULTURING PLURIPOTENT STEM CELLS

CROSS-REFERENCE TO RELATED APPLICATIONS

This patent application is a National Stage Entry of International Patent Application No. PCT/SG2014/000504, filed on Oct. 27, 2014, which claims priority to SG 201307979-3, filed on Oct. 25, 2013, the entire contents of each of which are hereby incorporated by reference herein.

FIELD OF THE INVENTION

The present invention relates stem cells. In particular the present invention relates to a method for culturing and maintaining a pluripotent stem cell in an undifferentiated state.

BACKGROUND OF THE INVENTION

Embryonic stem cells (ESCs) are derived from the inner cell mass (ICM) of the blastocyst. ESCs are able to differentiate into three germ layers and potentially all cells from the adult body.

This pluripotent characteristic makes them desirable in the field of regenerative medicine and provides an invaluable tool for dissecting early embryonic development. Even though ESCs share this property with the pluripotent epiblast cells of the inner cell mass, differences have been observed.

While it would be of great benefit to have a human embryonic stem cell (hESC) state that closely resembles in vivo development, it is not clear how far the in vitro culture conditions of hESCs are limited in imitating the environment of the blastocyst where pluripotency exists only transiently.

In mouse, it has been reported that multiple cell types fulfill the requirements of pluripotency and that these distinct cells match different embryonic developmental stages.

Factor mediated isolation of different pluripotent states has also been successfully applied on human cells, showing the in principle feasibility to interconvert between multiple pluripotent cell types.

In order to obtain hESCs which more closely resemble the native pluripotent epiblast, a transgene free method would be advantageous.

Accordingly, it is an aim of the present invention to provide and maintain a pluripotent stem cell state that ameliorates the disadvantages of the prior art and differentiates more efficiently.

SUMMARY OF THE INVENTION

In a first aspect there is provided a method for culturing and maintaining a pluripotent stem cell in an undifferentiated state comprising culturing the pluripotent stem cell in a medium comprising an MEK inhibitor, a GSK3 inhibitor, a dual inhibitor of AMPK and/or BMP signaling and LIF.

In a second aspect there is provided a pluripotent stem cell produced by the method as described herein.

In a third aspect there is provided a method for generating lineage specific cells from a pluripotent stem cell, comprising: a) culturing a pluripotent stem cell in an undifferentiated state according to the method described herein; b) isolating the undifferentiated pluripotent stem cell; and c) culturing the isolated undifferentiated pluripotent stem cell in a culture medium suitable to differentiate the isolated pluripotent stem cell into a lineage specific cell.

In a fourth aspect there is provided a kit when used in the method as described herein for culturing and maintaining a pluripotent stem cell in an undifferentiated state comprising a culture medium as described and instructions for use.

Definitions

As used herein the phrase "culture medium" refers to a liquid substance used to support the growth of stem cells and any of the cell lineages. The culture medium used by the invention according to some embodiments can be a water-based medium which may comprise a combination of substances such as salts, nutrients, minerals, vitamins, amino acids, nucleic acids, proteins such as cytokines, growth factors and hormones.

As used herein, the term "feeder cell" refers to feeder cells (e.g., fibroblasts) that maintain stem cells in a proliferative state when the stem cells are co-cultured on the feeder cells or when the pluripotent stem cells are cultured on a matrix (e.g., an extracellular matrix, a synthetic matrix) in the presence of a conditioned medium generated by the feeder cells. The support of the feeder cells depends on the structure of the feeder cells while in culture (e.g., the three dimensional matrix formed by culturing the feeder cells in a tissue culture plate), function of the feeder cells (e.g., the secretion of growth factors, nutrients and hormones by the feeder cells, the growth rate of the feeder cells, the expansion ability of the feeder cells before senescence) and/or the attachment of the stem cells to the feeder cell layer(s).

As used herein the term "laminin" refers to any of the family of glycoproteins that are typically involved in the formation and maintenance of extracellular matrices. Laminin is a heterotrimer formed from an $\alpha$ chain, $\beta$ chain, and a $\gamma$ chain. In some aspects of the present disclosure, fragments, derivatives, or analogs of various laminins can be used, such as laminins having at least a portion at least substantially homologous to the laminin al chain.

As used herein, the term "collagen" as used herein is understood as meaning all collagen types and any form of collagen, whether native nor not, atelocollagen, insoluble collagen, collagen fibers, soluble collagen, and acid-soluble collagen.

As used herein the term "fibronectin" refers to a disulfide linked dimeric glycoprotein (which is present in a soluble form in blood plasma and other body fluids, and is deposited in a fibrillar form as a major constituent of the extracellular matrix of loose connective tissue. It is composed of three different structural motifs, termed type I, II, and III homologies resulting in a modular organization of the fibronectin molecule in which its several biological activities can each be attributed to specific domains.

As used herein the term "proteoglycan" means "human secretory proteoglycan" which may or may not contain glycosaminoglycan chains covalently bound to the proteoglycan's core protein. The term is also meant to include peptide fragments of human secretory proteoglycan wherein the peptide core protein contains less than the naturally-occurring number of amino acids, such as partial fragments of proteoglycan which retain biological (functional or structural) activity.

As used herein the term "functional" is the ability to induce a specific biological response in the same manner that the native non-recombinant protein does. An example of a structural activity is the ability to bind antibodies which also recognize the native non-recombinant protein. The term is also used to include any peptide which comprises the sequence of a naturally-occurring protein or an analog thereof together with one or more flanking amino acids, which show biological (functional or structural) activity.

A "functional derivative" refers to a biological activity (either functional or structural) that is substantially similar to a biological activity of non-recombinant protein or other biological molecule. A functional derivative may or may not contain post-translational modifications. The term "functional derivative" is intended to include the "fragments," "variants," "analogues," or "chemical derivatives" of a molecule.

As used herein the term "fragment" is intended to refer to any variant of the molecule, such as the peptide core, or a variant of the peptide core which may or may not be functional.

As used herein the term "variant" is intended to refer to a molecule substantially similar in structure and biological activity to either the entire molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical.

As used herein an "analog" of a molecule is intended to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Moieties capable of mediating such effects are disclosed in Remington's Pharmaceutical Sciences (1980). Procedures for coupling such moieties to a molecule are well known in the art.

As used herein the term "entactin" is also intended to refer to nidogen-1 (NID-1). Entactin is a component of the basement membrane alongside other components such as collagen type IV, proteoglycans (heparan sulfate and glycosaminoglycans), laminin and fibronectin.

As used herein "heparan sulfate" is a member of the glycosaminoglycan family of carbohydrates and is very closely related in structure to heparin. Both consist of a variably sulfated repeating disaccharide unit.

The term "biopolymer" as used herein refers to a single biopolymer or a mixture of two or more biopolymers. "Biopolymers" is used to denote both natural polymers, including but not limited to polysaccharides (cellulose, Starch, and the like); polymers synthesized from natural products and by-products.

As used herein, RNA-sequencing refers to techniques used to determine the sequence of RNA molecules and/or to quantify the amount of RNA molecules in a sample. RNA molecules include but are not limited to total RNA, messenger RNA (mRNA), ribosomal RNA (rRNA), transfer RNA (tRNA), small interfering RNA (siRNA), micro RNA (miRNA) or RNA fragments.

As used herein, real-time PCR refers to polymerase chain reaction (PCR) techniques used to monitor the signal emitted from the PCR assay during the reaction as an indicator of amplicon production during each PCR amplification cycle (i.e., in "real time"), as opposed to conventional PCR methods, in which an assay signal is detected at the endpoint of the PCR reaction.

As used herein, a "MEK inhibitor" is a chemical or drug that inhibits the mitogen-activated protein kinase enzymes MEK1 and/or MEK2.

As used herein, a GSK3 inhibitor is a chemical or drug that inhibits glycogen synthase kinase 3.

As used herein, an AMPK inhibitor is a chemical or drug that inhibits 5' adenosine monophosphate-activated protein kinase.

As used herein, a BMP signaling inhibitor is a chemical or drug that inhibits bone morphogenic protein (BMP) signaling.

As used herein, "LIF" refers to leukemia inhibitory factor.

As used herein, the term "lineage specific cell" may be somatic cells or organoids. In another embodiment, the lineage specific cells may be endoderm lineage cells. In another embodiment, the somatic cell may be a committed progenitor cell capable of self-renewal or differentiation into one or several somatic lineages, or a fully mature somatic differentiated cell.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

BRIEF DESCRIPTION OF THE DRAWINGS

The invention will be better understood with reference to the detailed description when considered in conjunction with the non-limiting examples and the accompanying drawings, in which.

Figure 1:
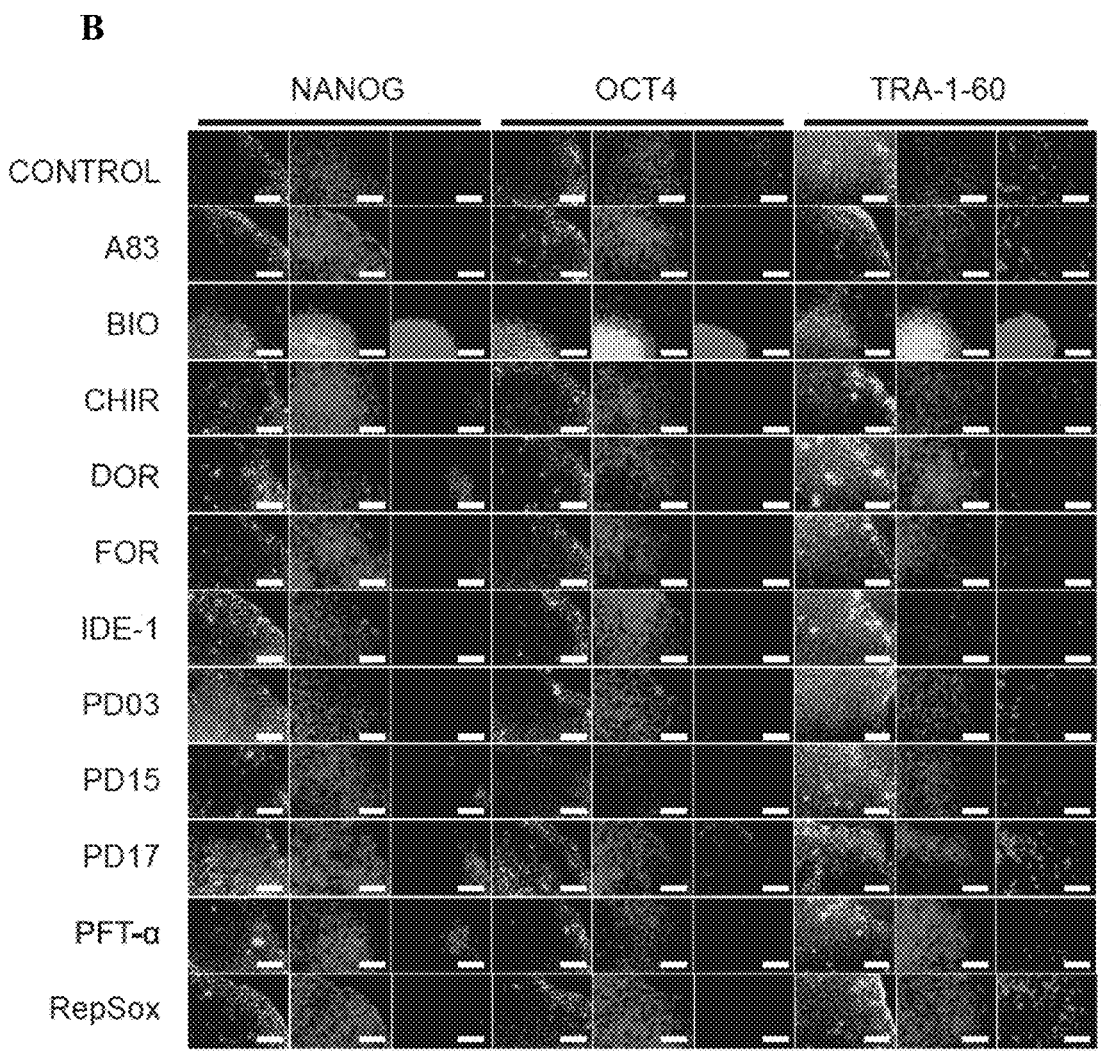
FIG. 1. Small molecule screening for novel culture conditions that support the human pluripotent cell state.
A) List of small molecules used to identify culture conditions that support novel pluripotent cell states. The names of the chemicals and the respective pathways which they target are shown.
B) Staining of hESCs treated with the individual chemicals for pluripotency markers NANOG, OCT4 and TRA-1-60.
Figure 1:
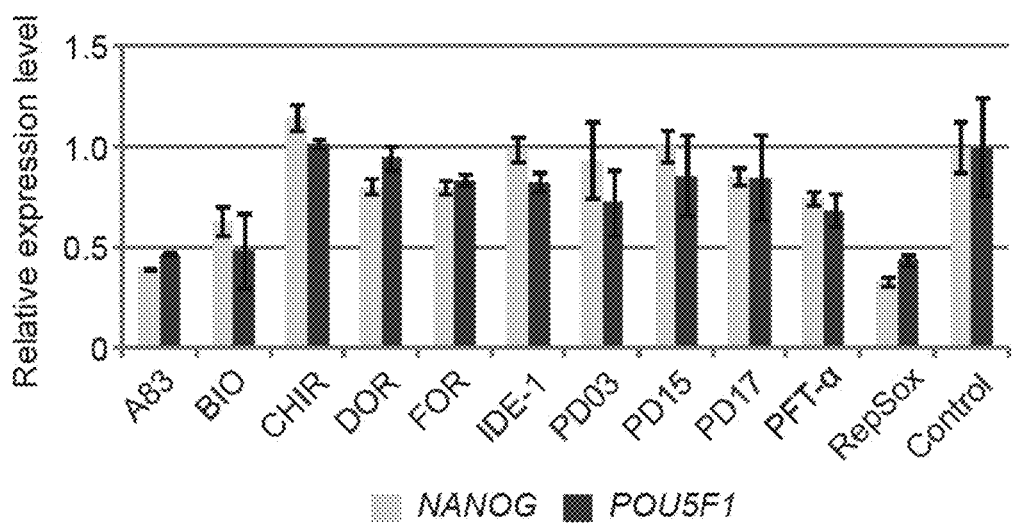
Figure 1:
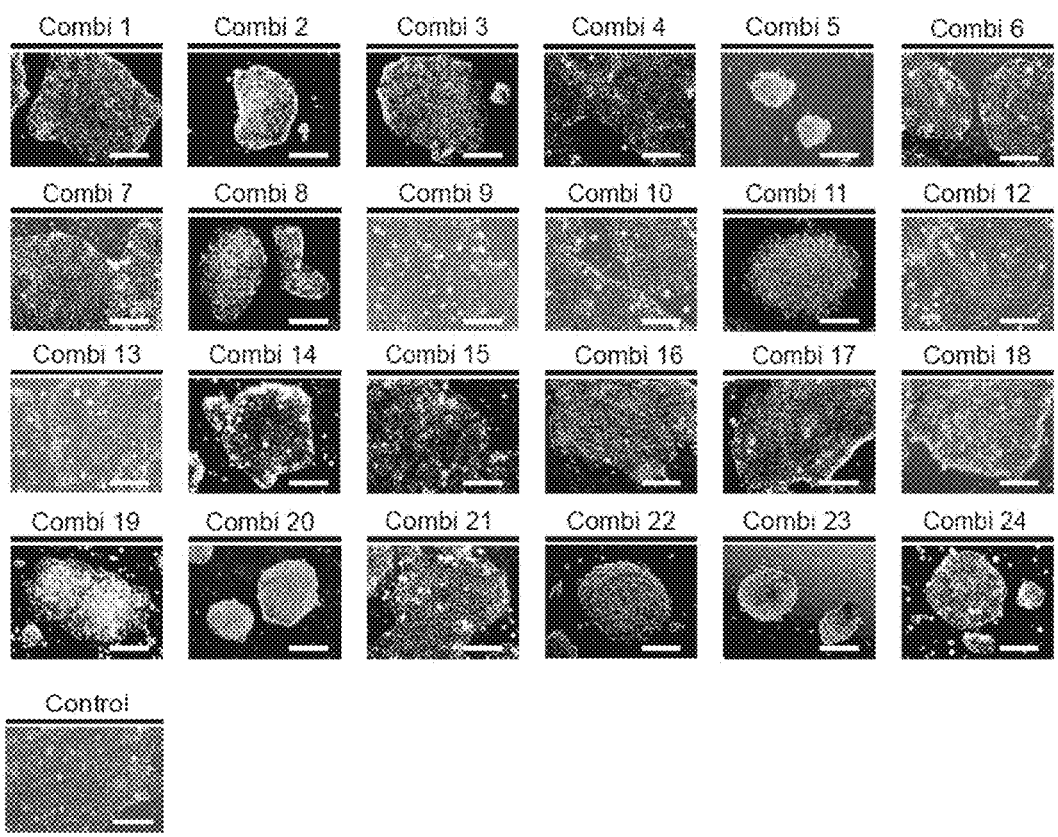
Figure 1:
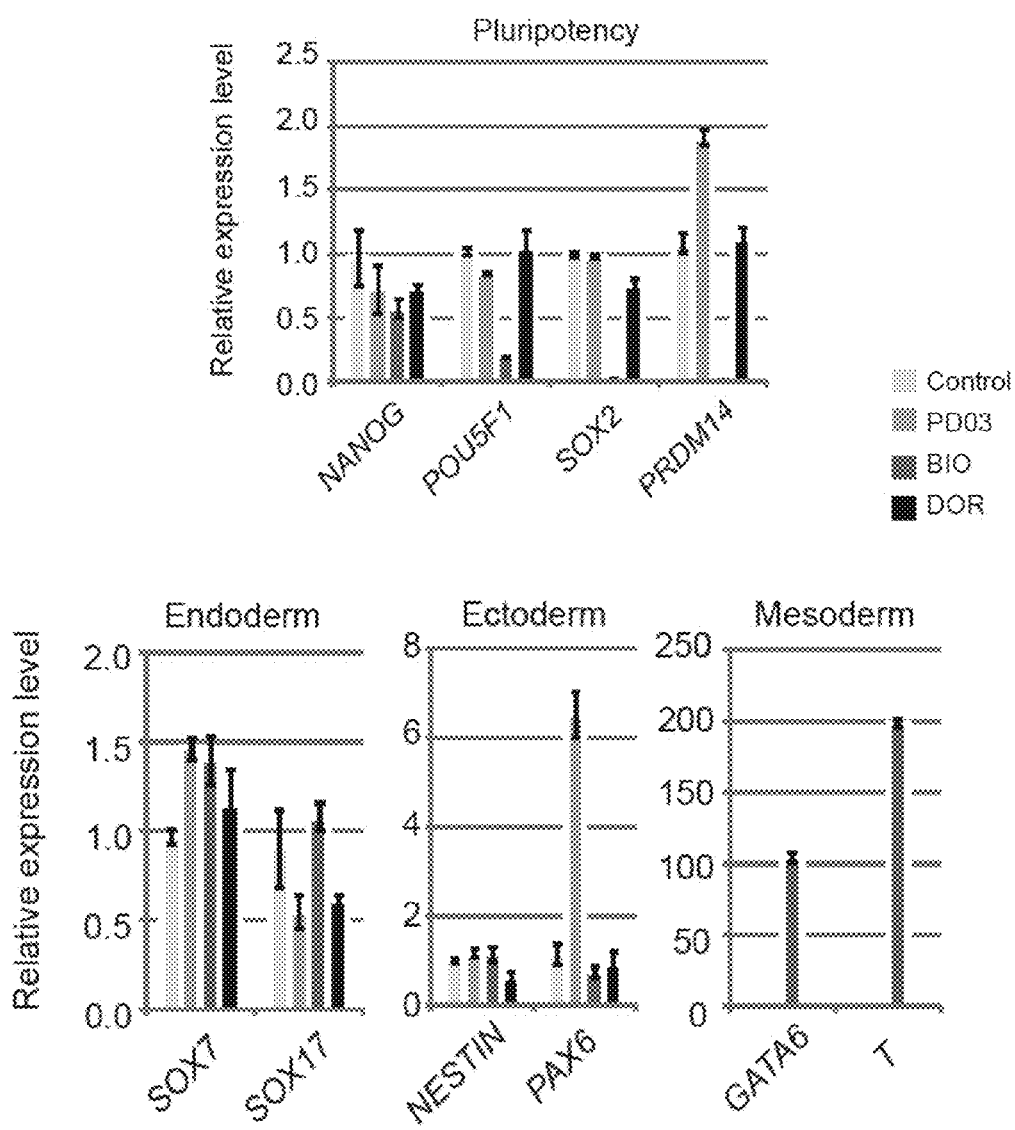
Figure 1:
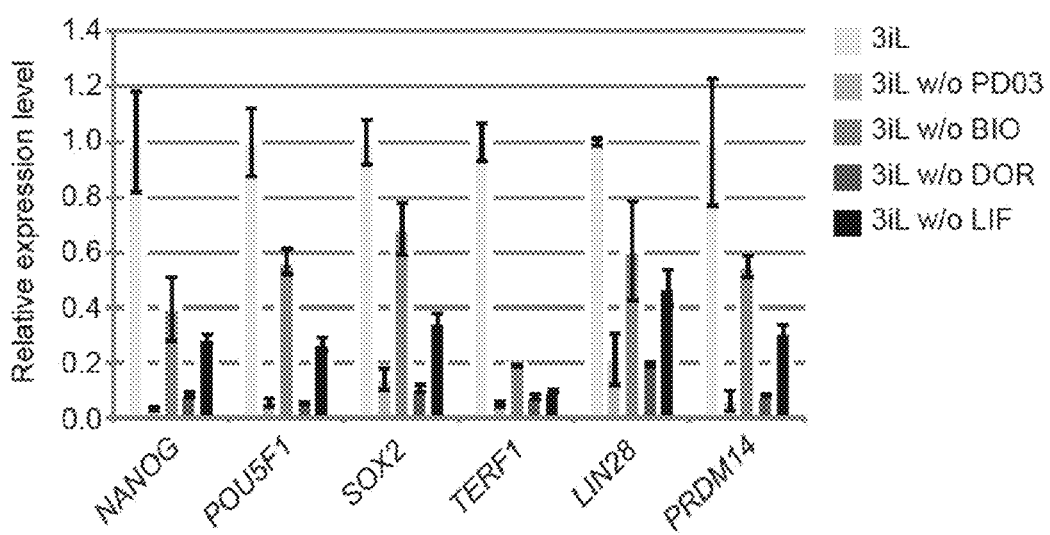

hESCs are seeded at a ratio of 1:12 and treated with the individual chemicals 48 hrs post seeding for 4 days. The level of pluripotency markers remains largely unchanged as compared to the control cells treated with DMSO. Scale bar represents 200 μm.

C) Gene expression levels of pluripotency markers in hESCs treated with the individual chemicals. hESCs treated with TGFβ inhibitors RepSOX and A83-01 as well as the GSK3β inhibitor BIO show downregulation of NANOG and POU5F1.

D) The 24 combinations of small molecule compounds that are used in this study.

E) Morphology of hESC colonies after treatment with the 24 combinations of small molecules. Scale bar represents 200 μm.

F) Cells were treated with the individual chemicals of combination 22 (PD03/BIO/DOR), subcultured onto feeders and harvested after 4 days to check for pluripotency marker expression. Expression of NANOG and POU5F1 remains in a comparable range for cells treated with PD03 or DOR. NANOG and POU5F1 were downregulated in BIO treated cells. The expression level of lineage markers was also analysed. There is an increase in the PAX6 transcript in PD03 treated cells and cells treated with BIO show a stronger upregulation of T and GATA6. All values are means±s.d from 3 independent experiments.

G) Removal of individual small molecules or LIF from the 3iL hESC culture conditions during conversion. hESCs were treated with the 3iL hESC conditions but without 1 of the 3 small molecules or without LIF. Cells were harvested for expression analysis when the hESC colony could no longer be sustained. Cells cultured without PD03 or LIF were harvested after 2 passages while cells cultured without BIO or DOR were harvested after 4 passages. Removal of the small molecules and LIF resulted in a decrease in pluripotency gene expression. Relative expression level is obtained via normalization against the control 3iL hESCs. All values are means±s.d from 3 independent experiments.

Figure 2:
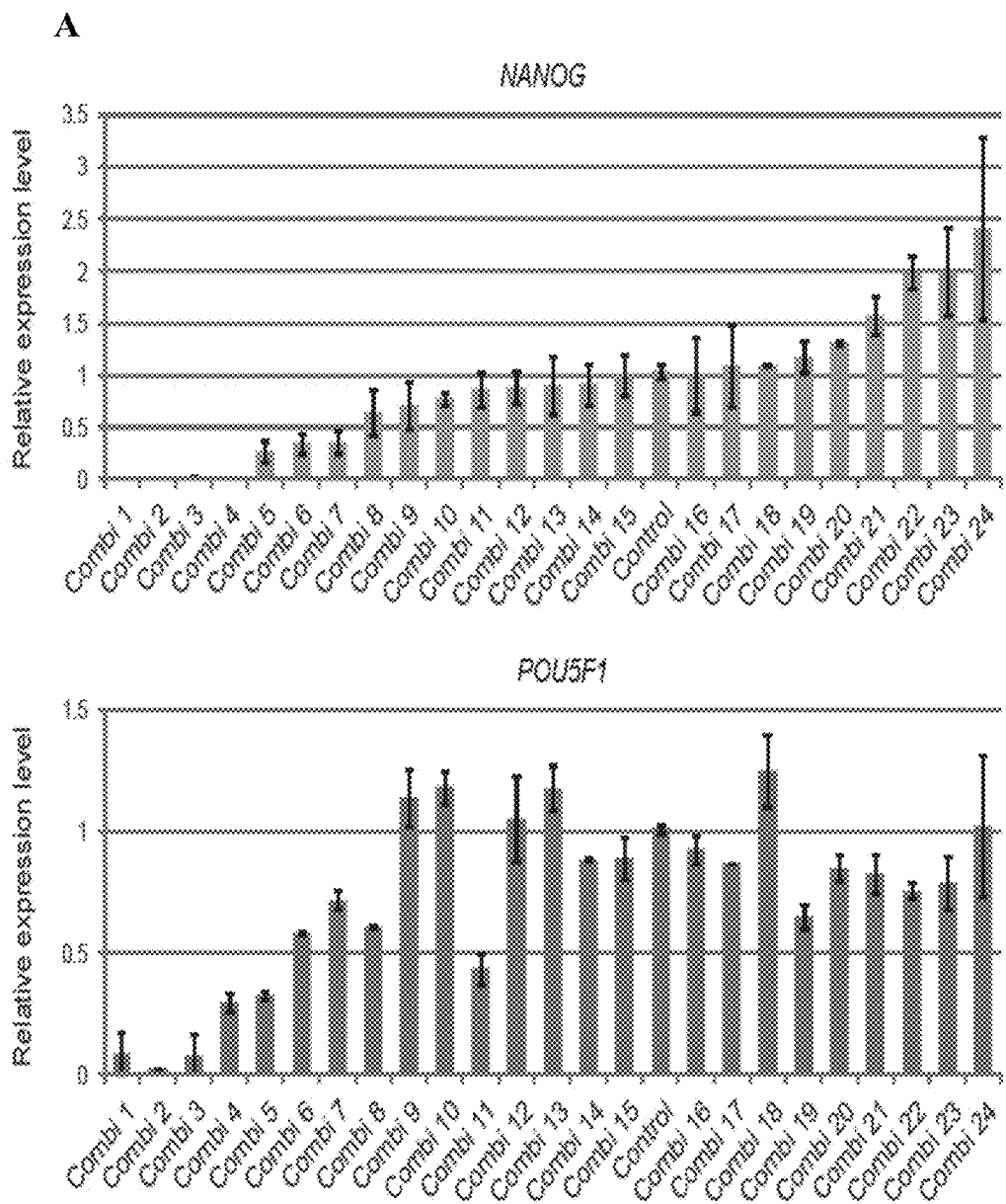
Figure 2:
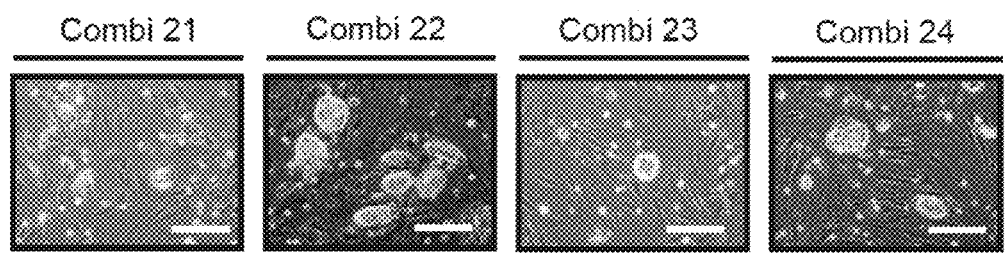
Figure 2:
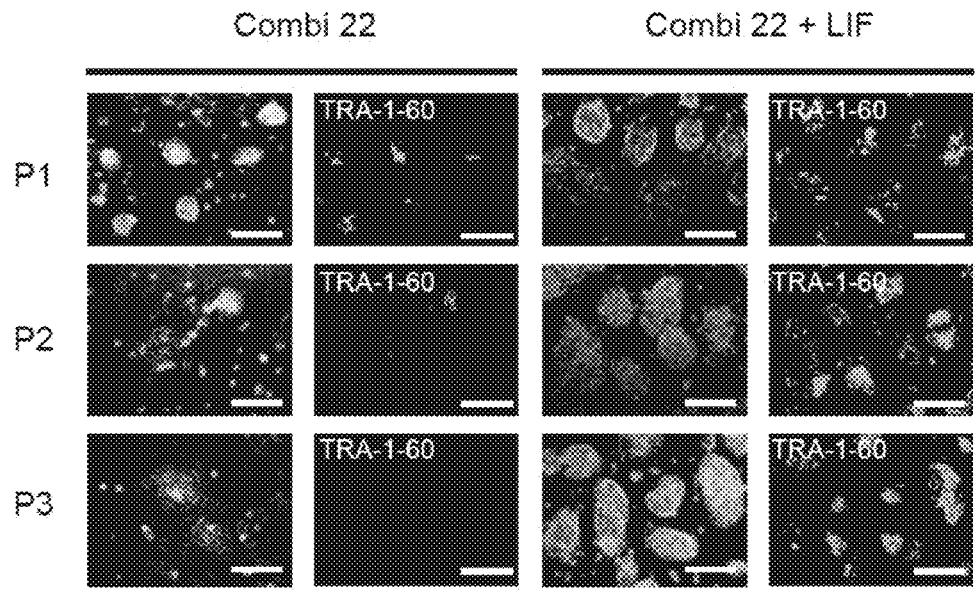
Figure 2:
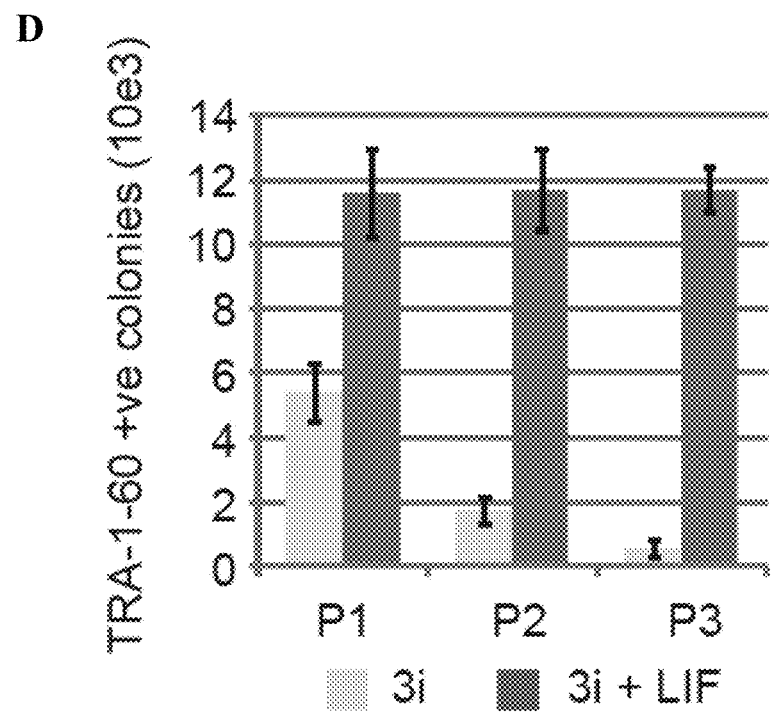
Figure 2:
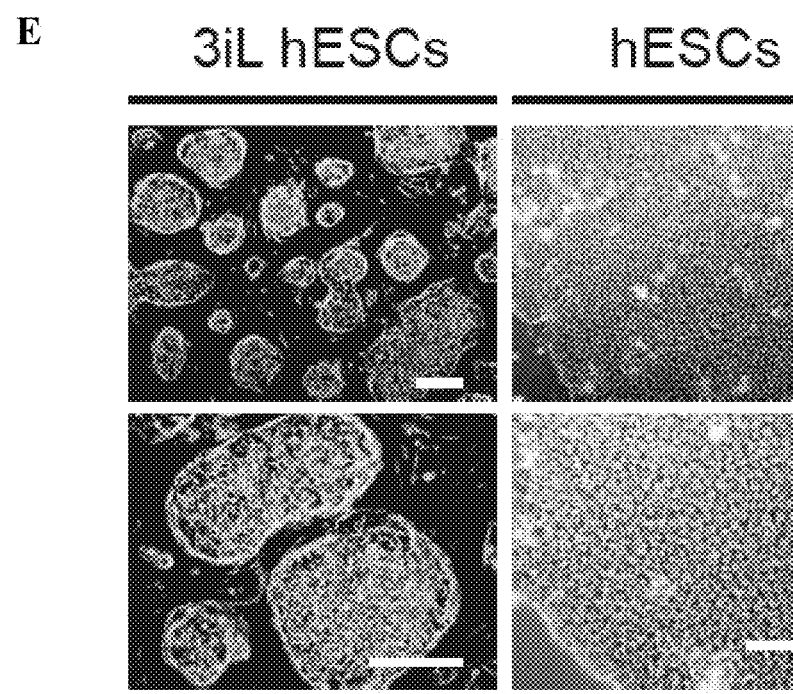
Figure 2:
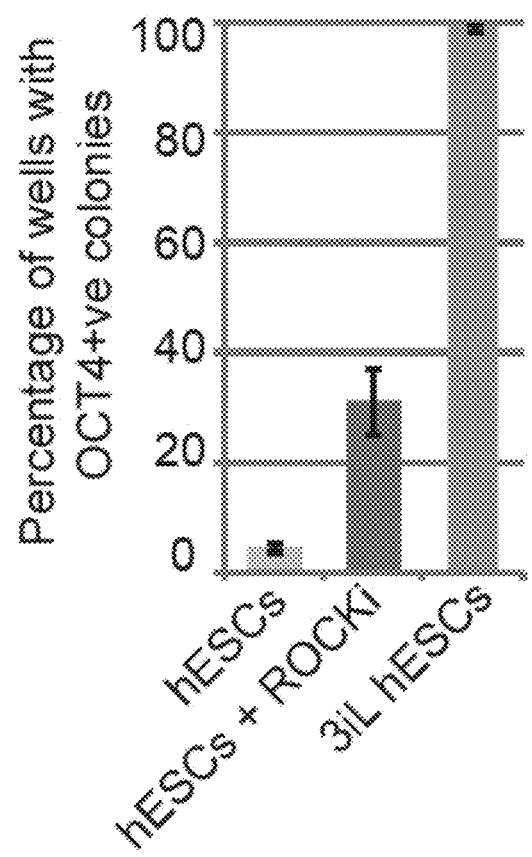

FIG. 2. Small-molecule treatment of hESCs induces a novel LIF-dependent hESC state.

A) Expression levels of pluripotency markers NANOG (top) and POU5F1 (bottom) for hESCs which were treated for 4 days with 24 different combinations of small molecules 48 hr post-seeding. Relative expression is obtained via normalization against the control samples treated with DMSO. All values are means±s.d from 3 independent experiments.

B) Propagation of hESCs treated with chemical combinations 21 to 24 on mouse fibroblast feeders. Only hESCs treated with combination 22 form small compact colonies. Scale bar represents 200 μm.

C) Cells treated with combination 22 proliferate only in the presence of human LIF. Cells treated combination 22 were continuously subcultured with or without LIF. For each passage (P1-P3), cells were fixed upon confluency and stained with hESC specific surface marker TRA-1-60. Scale bar represents 200 μm.

D) Shown are the numbers of TRA-1-60 positive colonies for hESCs cultured in 3i, with or without LIF (P1-3). All values are means±s.d from 3 independent experiments.

E) Morphology of 3iL hESCs and hESCs. Scale bar represents 200 μm.

F) 3iL hESCs can be subcultured as single cells. 3iL hESCs and hESCs were subcultured as single cells into 96 well culture dishes at clonal density. hESCs treated with and without ROCK inhibitor (1 μM Thiazovivin) served as control. The cells were maintained for 5 days, fixed and stained for OCT4. All values are means±s.d from 3 independent experiments.

Figure 3:
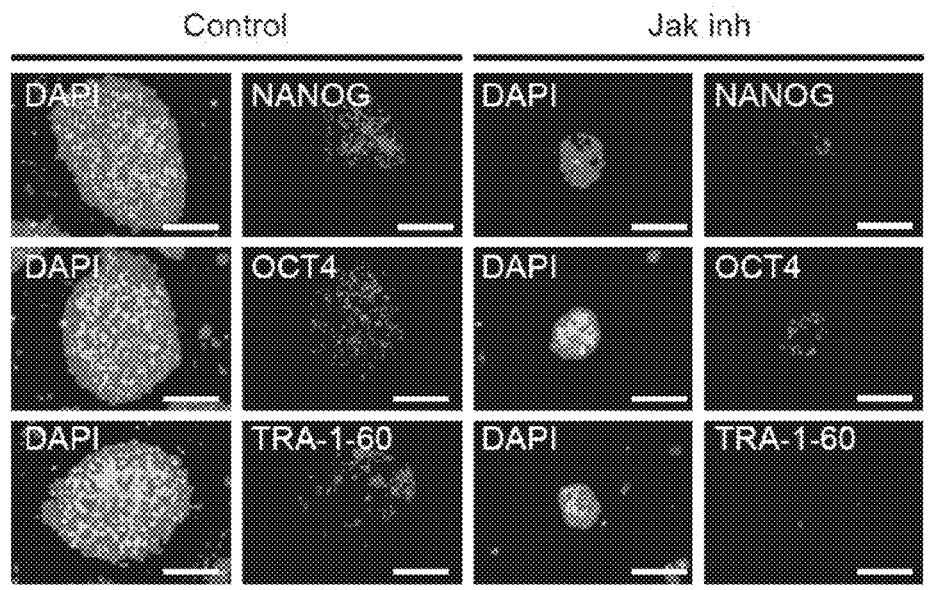
Figure 3:
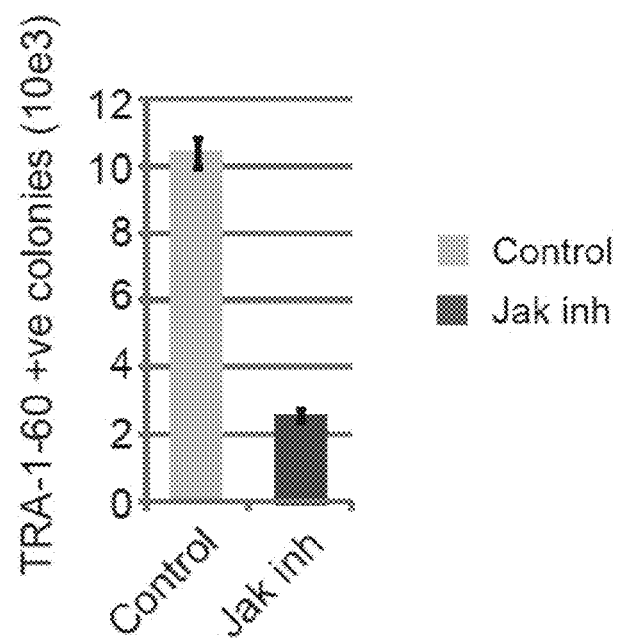
Figure 3:
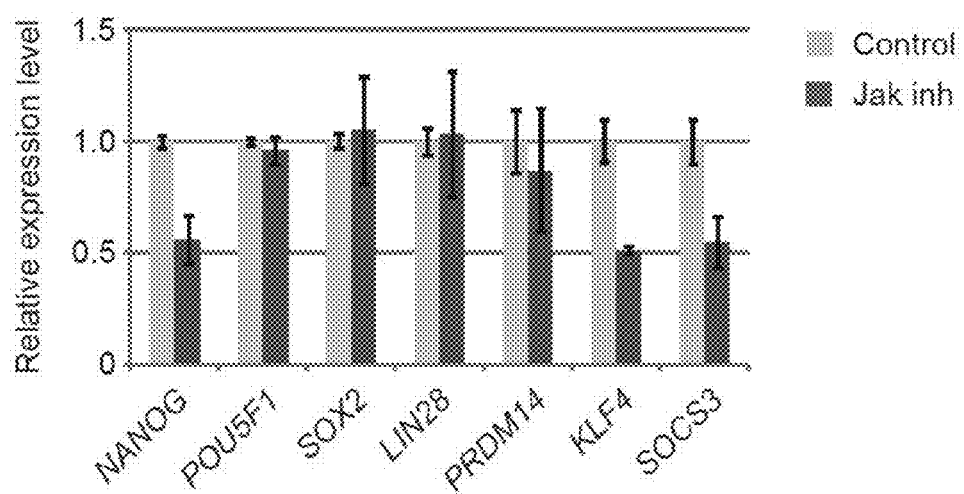
Figure 3:
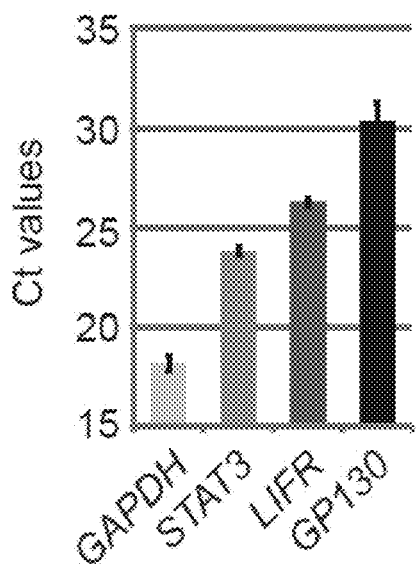
Figure 3:
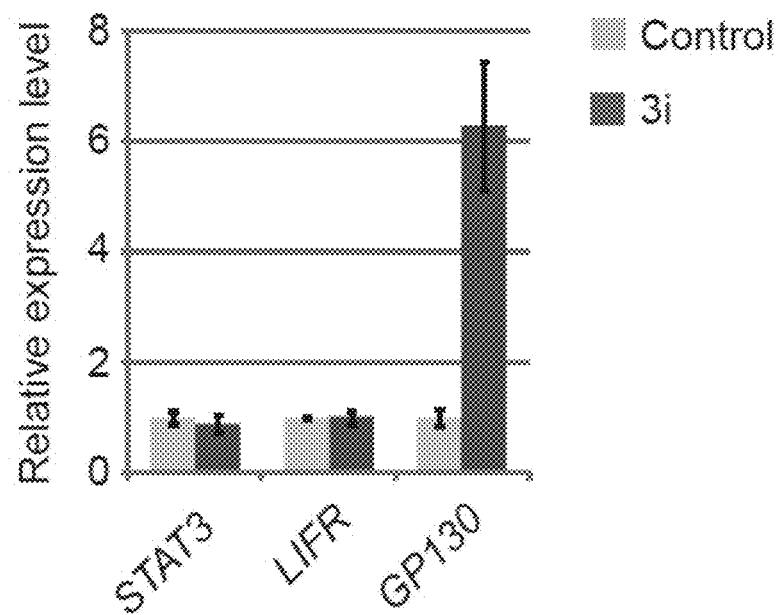
Figure 3:
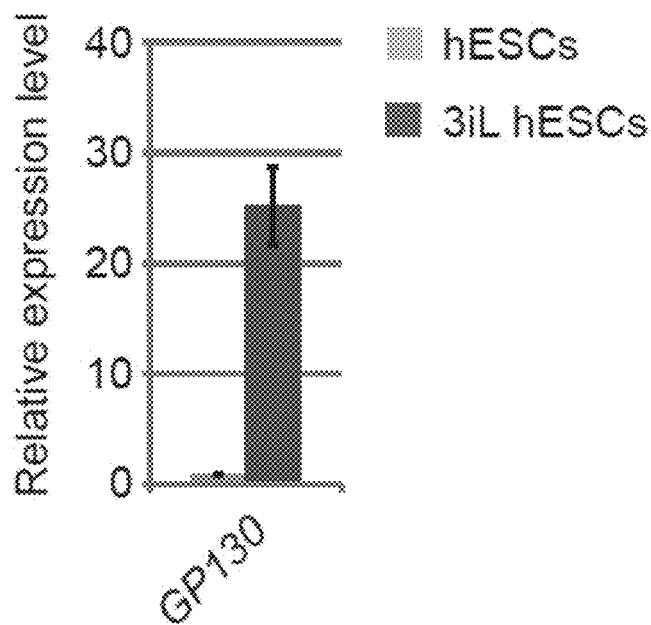
Figure 3:
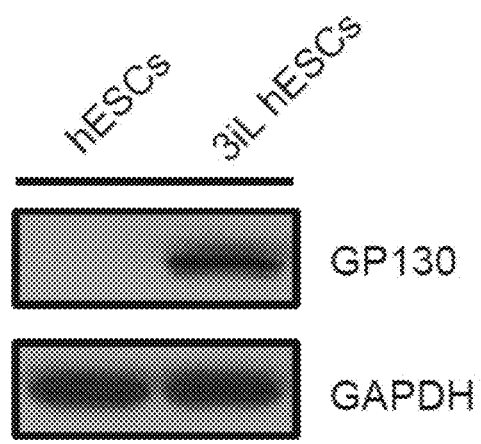
Figure 3:
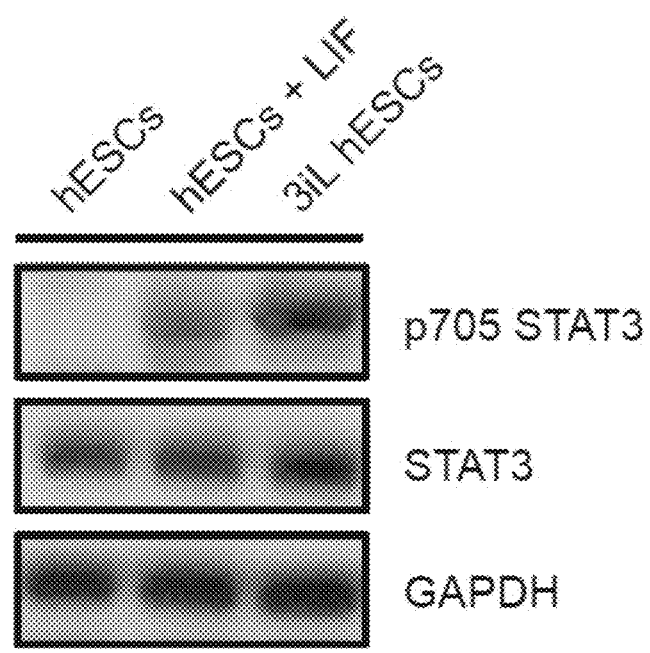
Figure 3:
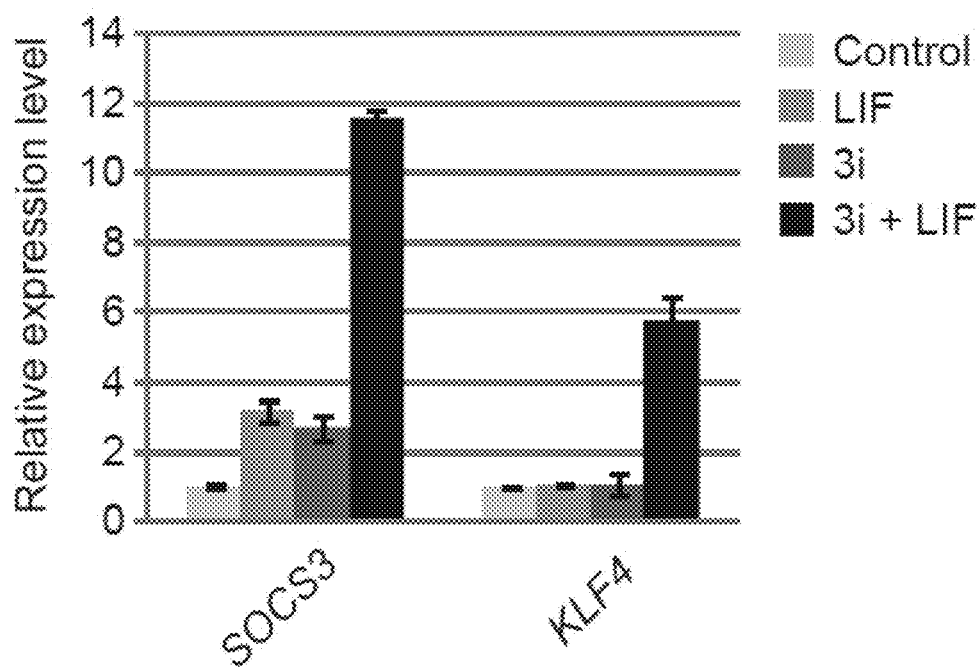

FIG. 3. Self renewal of 3iL hESCs is dependent on LIF signaling.

A) 3iL hESCs were treated with 0.6 μM of Jak inhibitor (inh). Control cells were treated with DMSO. The cells were fixed after 10 days of treatment and stained for pluripotency markers NANOG, OCT4 and TRA-1-60.

B) Number of TRA-1-60 positive colonies in 3iL hESCs with and without Jak inh. All values are means±s.d from 3 independent experiments.

C) Expression of pluripotency genes and LIF signaling responsive genes in hESCs with and without Jak inh. All values are means±s.d from 3 independent experiments.

D) Expression of LIF signaling components in hESCs. Shown are the average Ct values of STAT3, LIFR, GP130 and housekeeping gene GAPDH. The high Ct value indicates that GP130 is poorly expressed in hESCs. All values are means±s.d from 3 independent experiments.

E) Induction of GP130 expression when hESCs were treated with 3i. Relative expression levels were obtained via normalization against a control sample treated with DMSO. All values are means±s.d from 3 independent experiments.

F) Relative expression level of GP130 in 3iL hESCs and hESCs. All values are means±s.d from 3 independent experiments.

G) Upregulation of GP130 protein in 3iL hESCs compared to hESCs. Antibody specific to GP130 was used to detect the presence of GP130 in whole cell extract of 3iL hESCs and hESCs.

H) 3iL hESCs show higher levels of phosphorylated STAT3 compared to LIF treated hESCs. Whole cell extracts of hESCs, hESCs cultured with 10 ng/ml of LIF and 3iL hESCs were used to determine the level of STAT3 phosphorylation in the respective culture condition. The GAPDH protein level served as a loading control. Addition of LIF weakly activates STAT3 phosphorylation compared to the 3iL culture condition.

I) Activation of STAT3 responsive genes SOCS3 and KLF4 in hESCs after treatment with 3i, 3iL, or LIF for 4 days. All values are means±s.d from 3 independent experiments.

Figure 4:
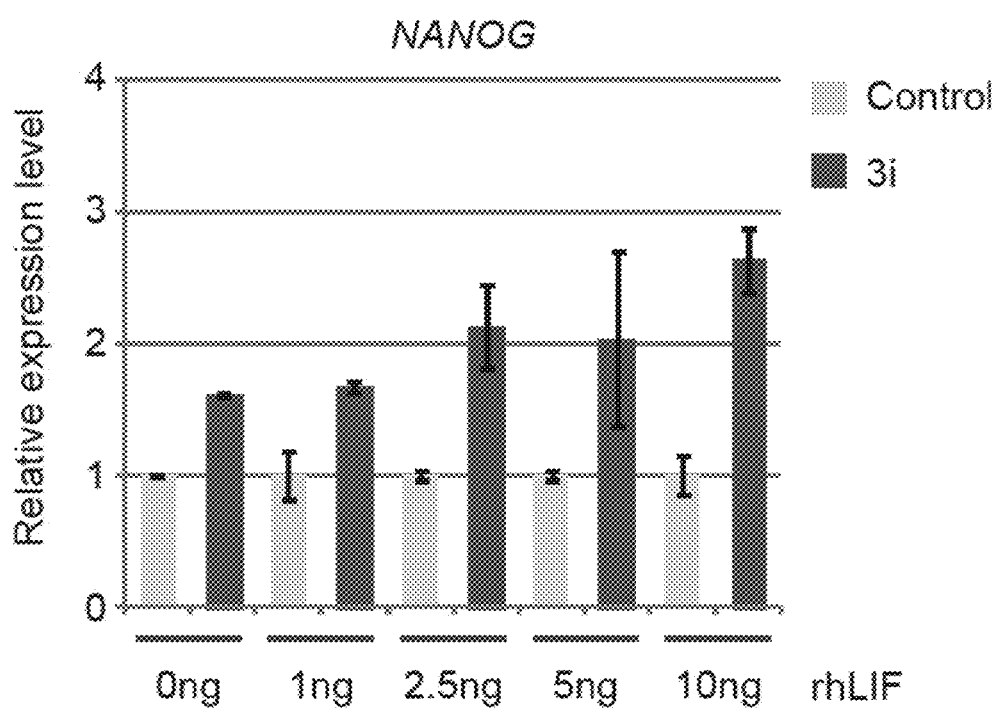
Figure 4:
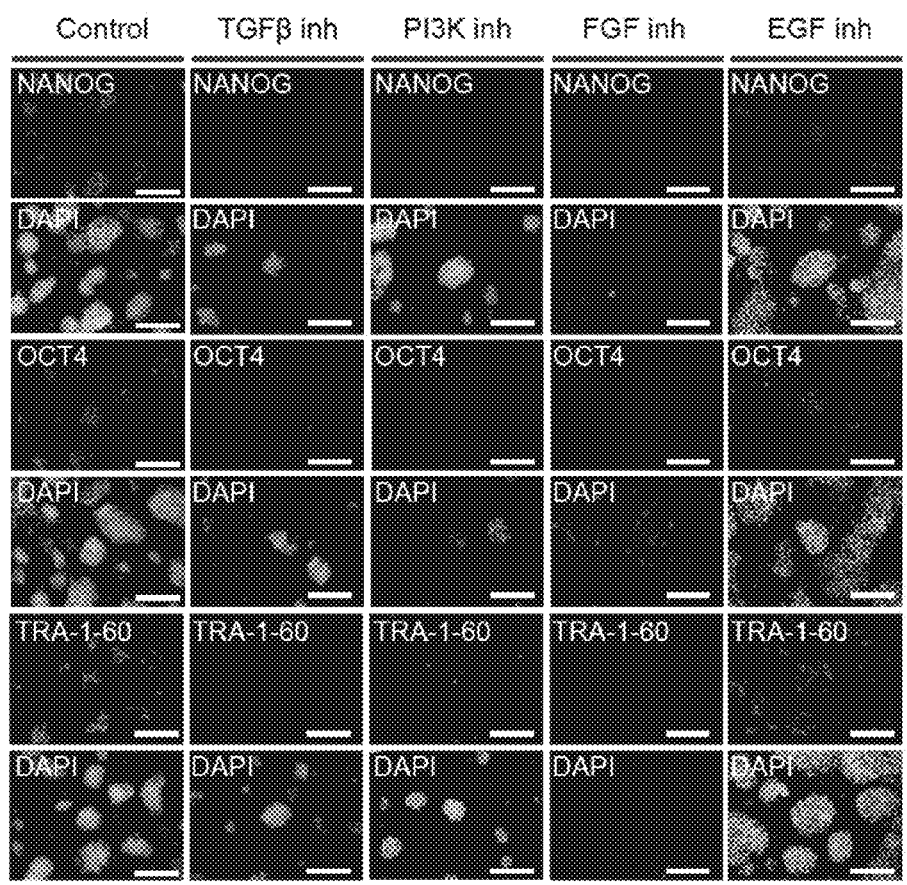
Figure 4:
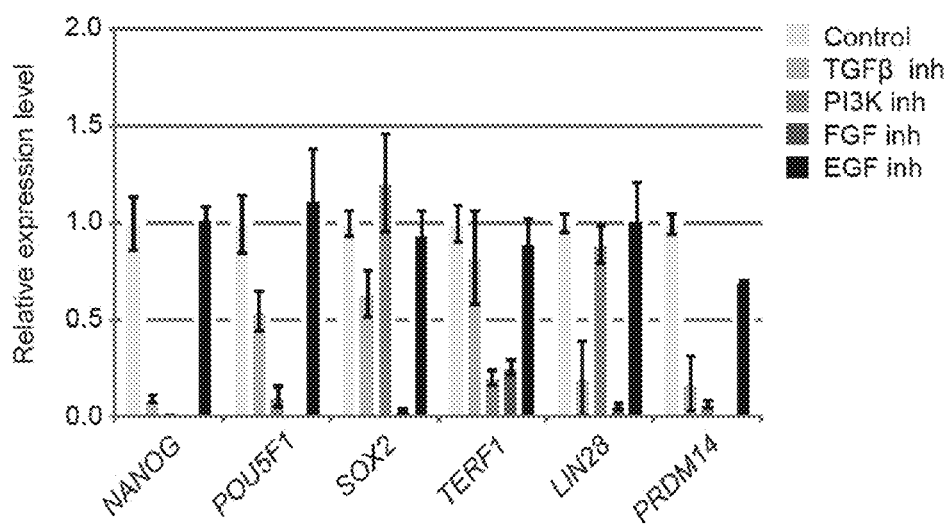

FIG. 4. Signaling pathway important for 3iL culture conditions.

A) NANOG expression level is responsive to LIF signaling in hESCs treated with 3i. hESCs were cultured with and without 3i, and treated with increasing amount of human recombinant LIF. After 5 days of treatment, the cells were harvested for expression analysis. The level of pluripotency gene NANOG is responsive to LIF signaling in a dosage dependent manner in the presence of the 3i small molecules as compared to control hESCs treated with DMSO.

B) Inhibition of key hESC signaling pathways results in the differentiation of 3iL hESCs. 3iL hESCs were treated with chemicals that inhibit the TGFβ signaling pathway (A83-01), FGF signaling pathway (PD173074), PI3K pathway (LY294002) and EGF pathway (PD15035). 3iL hESCs were treated for 10 days and stained for pluripotency markers. Inhibition of TGFβ, FGF and PI3K pathway in the 3iL hESCs results in the loss of pluripotency markers NANOG, OCT4 and TRA-1-60 as compared to the 3iL hESC control. Scale bar represents 200 μm.

C) Downregulation of pluripotency genes in 3iL hESCs treated with the signaling pathway inhibitors. All values are mean±s.d from 3 independent experiments.

Figure 5:
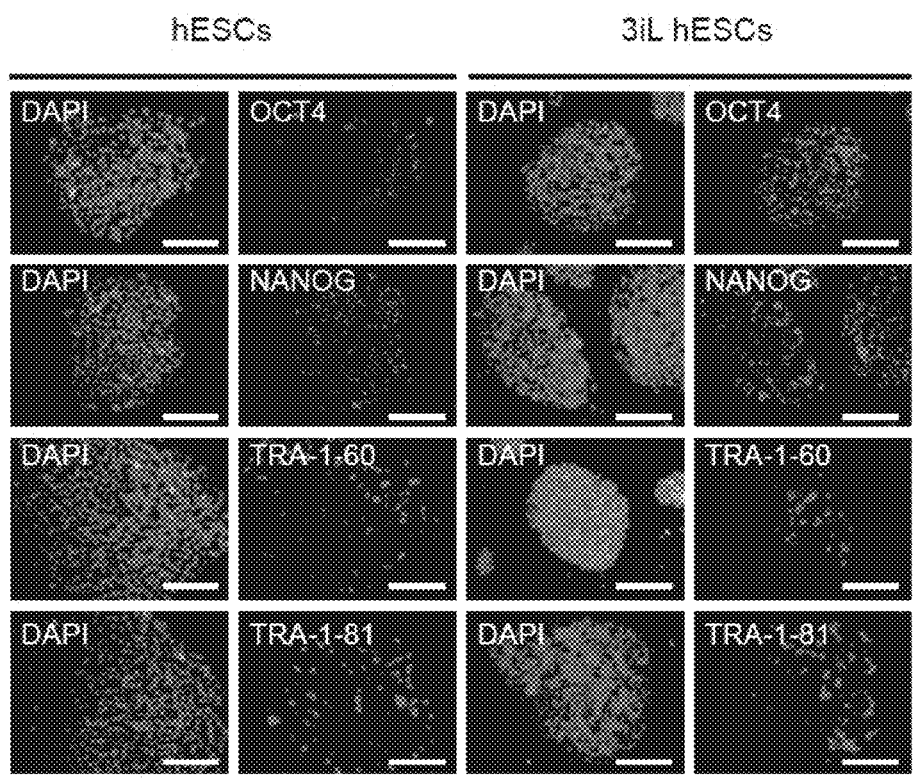
Figure 5:
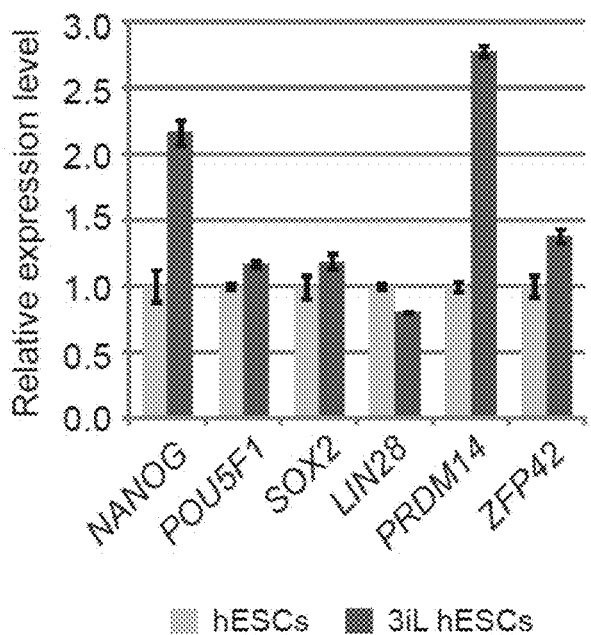
Figure 5:
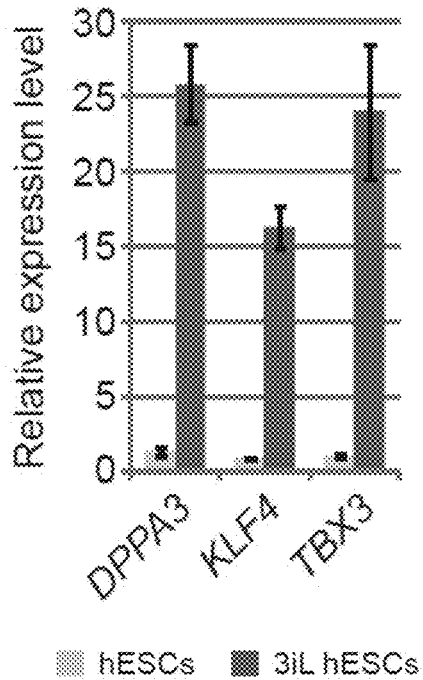
Figure 5:
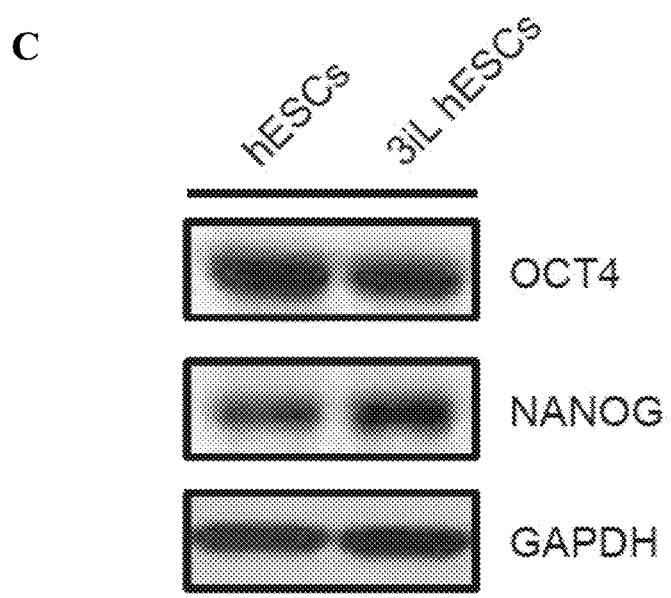
Figure 5:
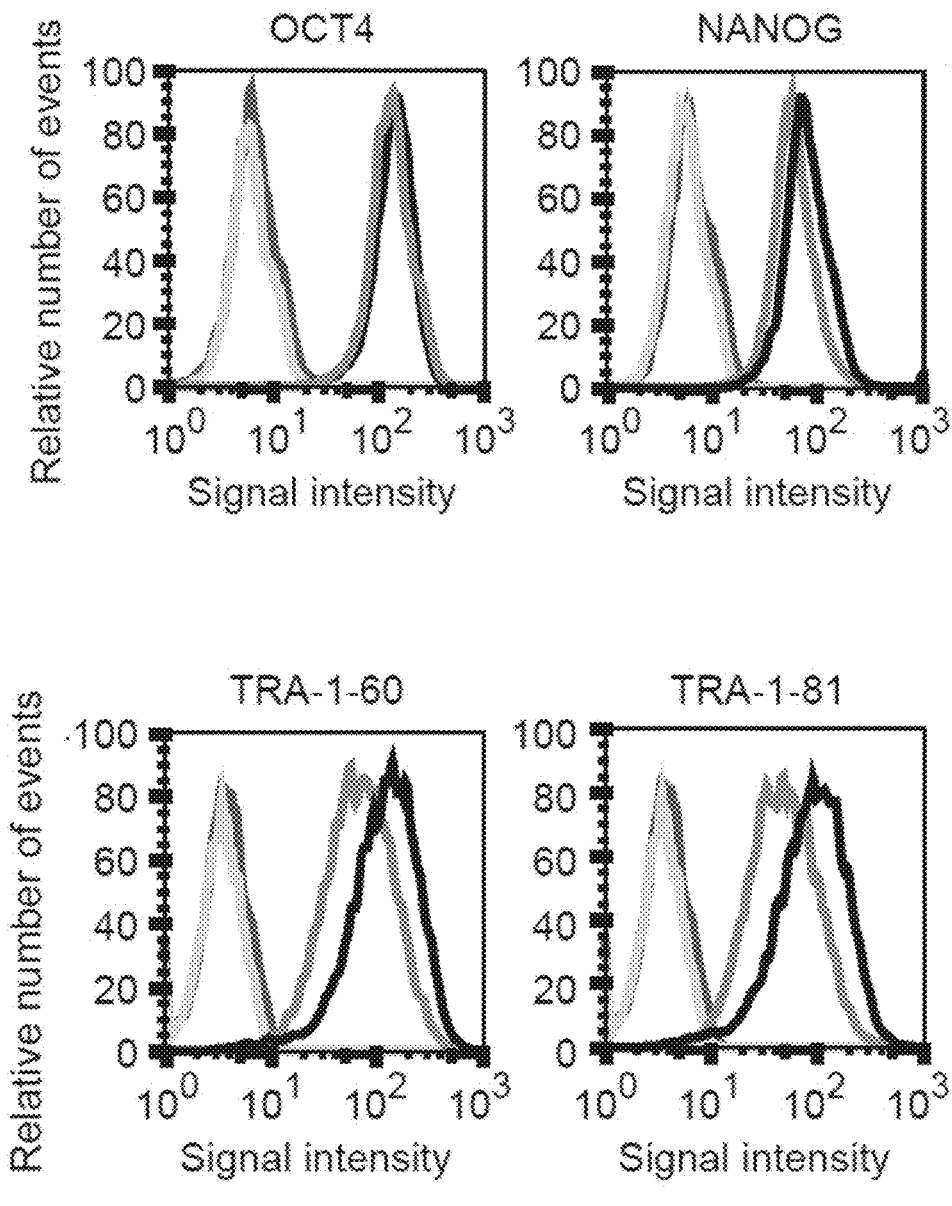
Figure 5:
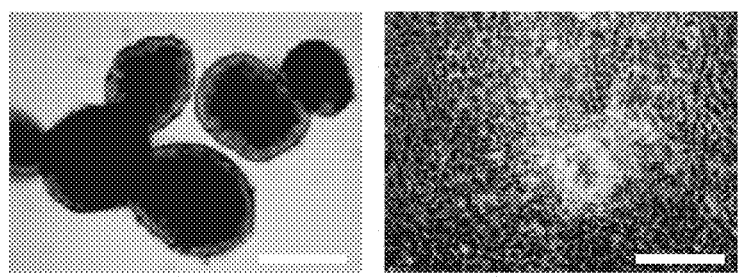
Figure 5:
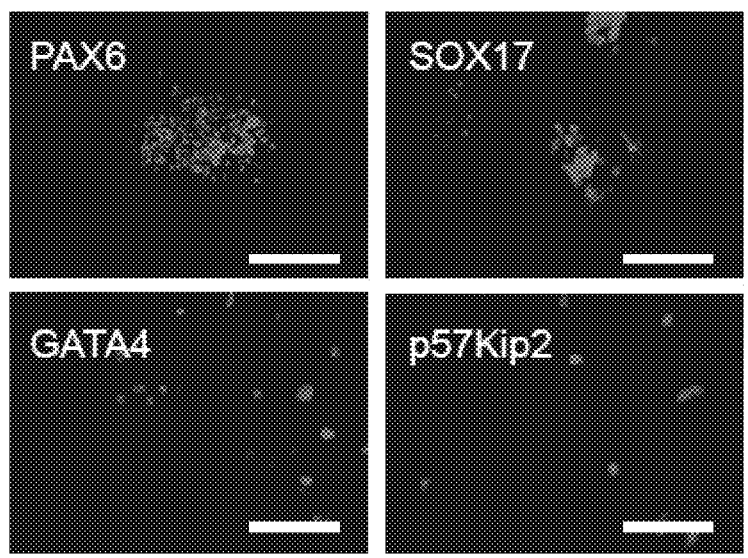
Figure 5:
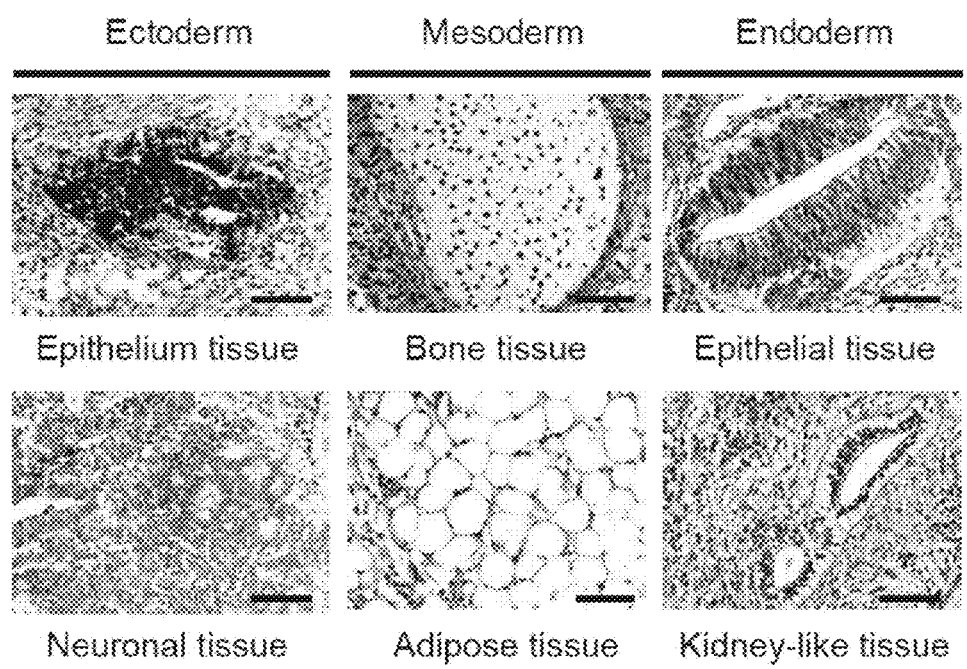
Figure 5:
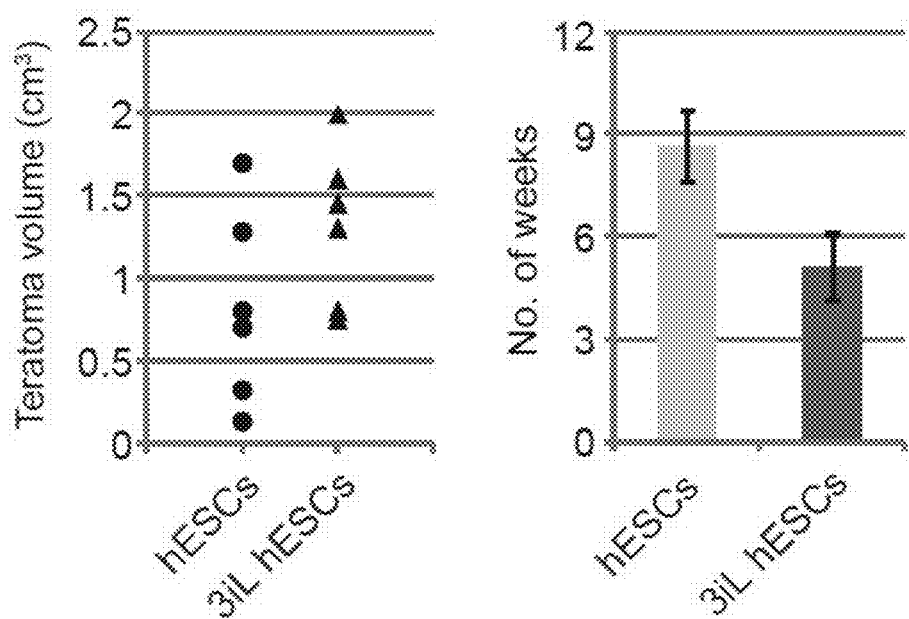
Figure 5:
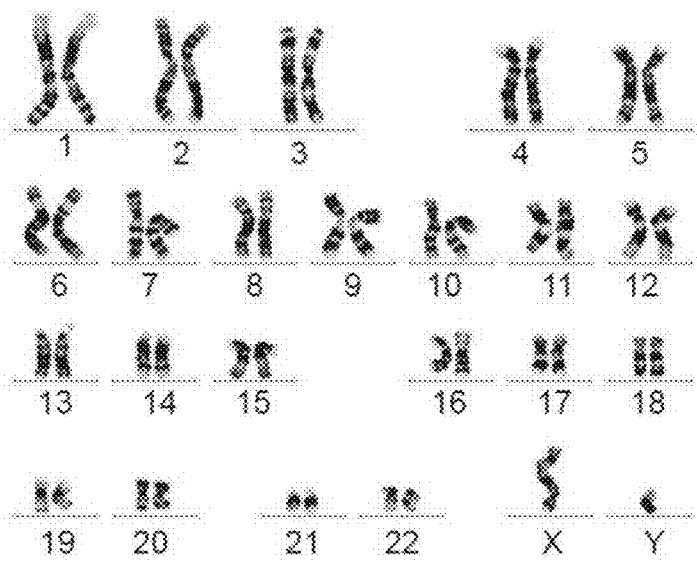

FIG. 5. 3iL hESCs are pluripotent.
A) Staining of 3iL hESCs and hESCs for pluripotency markers NANOG and OCT4, and hESCs specific cell surface markers TRA-1-60 and TRA-1-81. Scale bar: 200 µm.
B) Relative expression of pluripotency associated genes and epiblast genes in hESCs and 3iL hESCs. All values are mean±s.d from 3 independent experiments.
C) Western blot analysis of protein levels for NANOG and OCT4 in hESCs and 3iL hESCs. Corresponding to the increase in NANOG gene expression level, the NANOG protein level in 3iL hESCs is higher compared to hESCs.
D) FACS analysis of pluripotency markers in 3iL hESCs and hESCs indicates that 3iL hESCs express higher levels of NANOG, TRA-1-60 and TRA-1-81.
E) 3iL hESCs form embryoid bodies (EBs) in suspension culture and differentiate into the 3 germ layers and trophectoderm in vitro. Shown are 3iL hESC-derived EBs cultured for 20 days in suspension (top left panel) and the adhesion and expansion of embryoid bodies plated onto gelatin plates (top right panel).
F) 3iL hESCs can differentiate into ectoderm (PAX6), definitive endoderm (SOX17), mesoderm (GATA4) and trophectoderm (p57Kip2). Scale bar: 200 µm.
F) 3iL hESCs form teratomas when injected into SCID mice. Shown are teratoma sections containing tissues which are representative of all three embryonic germ layers. Scale bar: 50 µm.
G) 3iL hESCs form teratomas more efficiently than hESCs. Volume of teratoma formed by 3iL hESCs (left panel) and average time taken for the formation of the teratoma (right panel. Shown are 6 replicates for each condition.
H) 3iL hESCs exhibit a normal karyotype after 2 months in culture.

Figure 6:
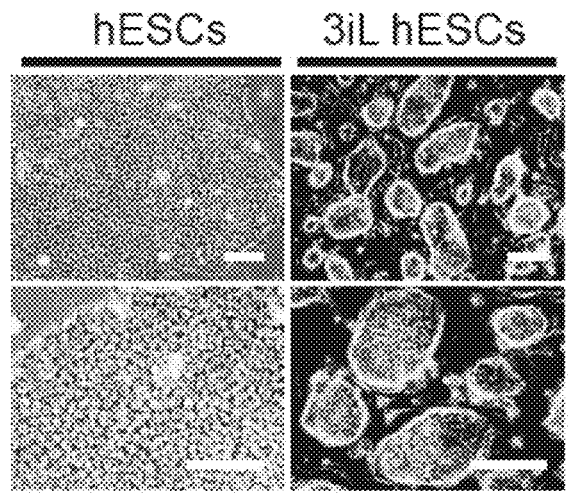
Figure 6:
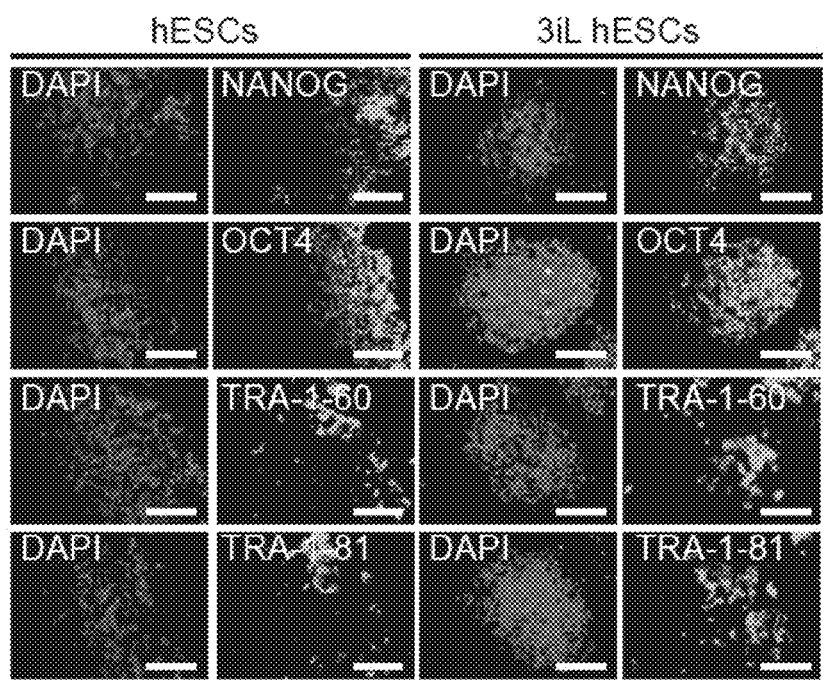
Figure 6:
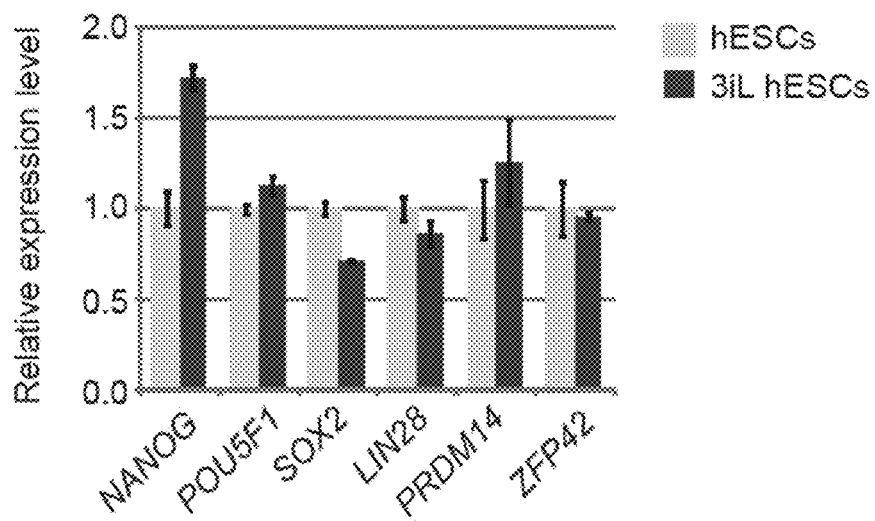
Figure 6:
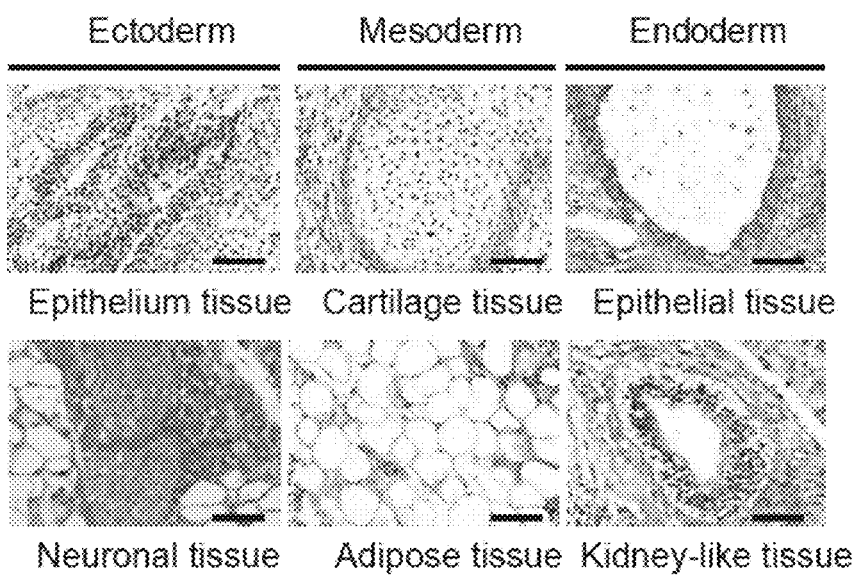
Figure 6:
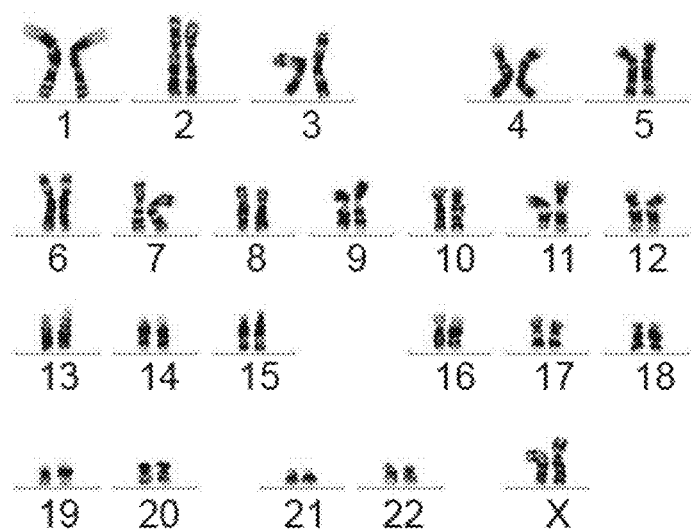
Figure 6:
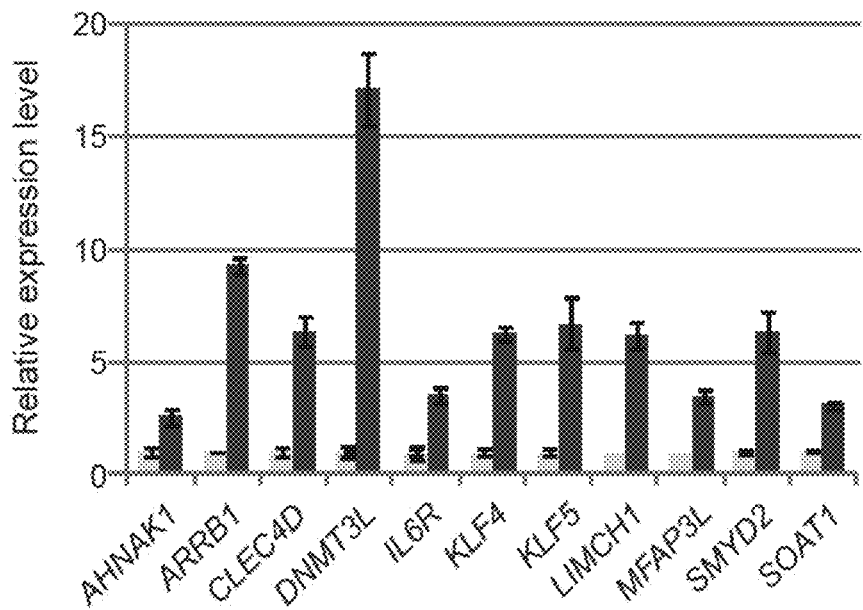
Figure 6:
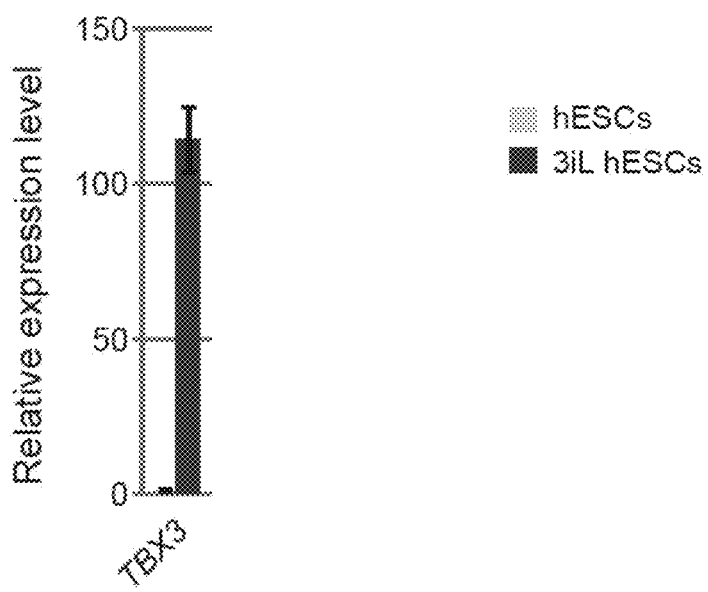
Figure 6:
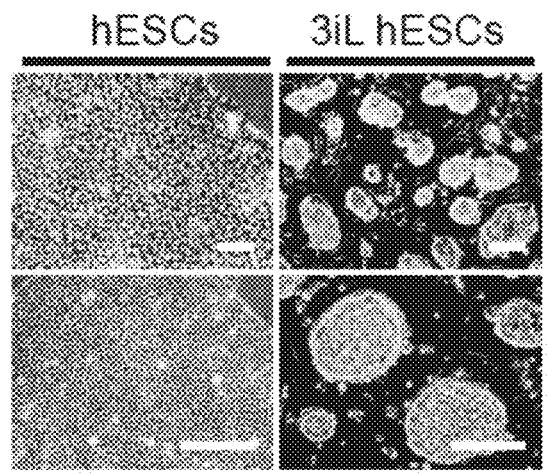
Figure 6:
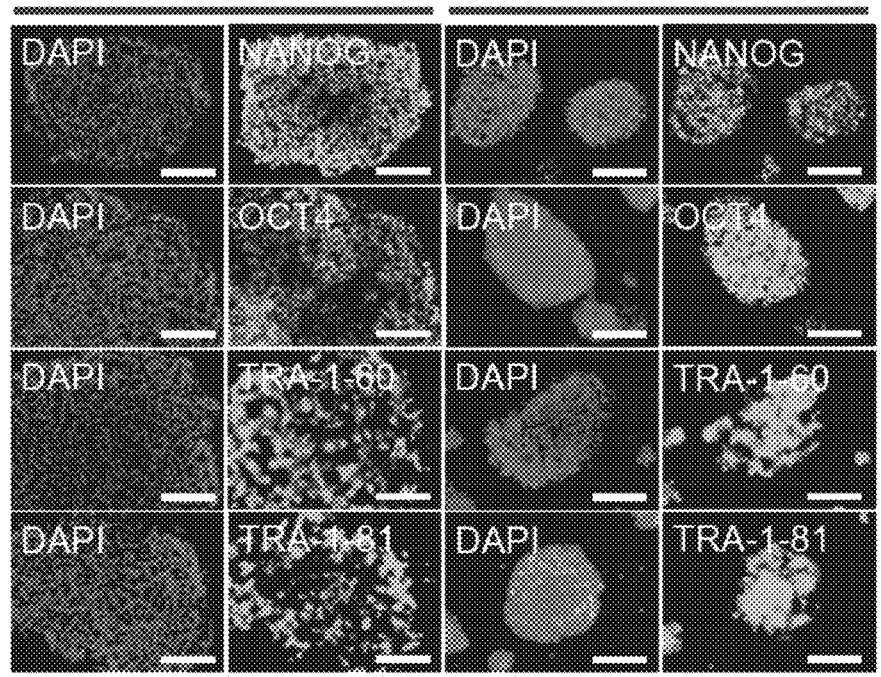
Figure 6:
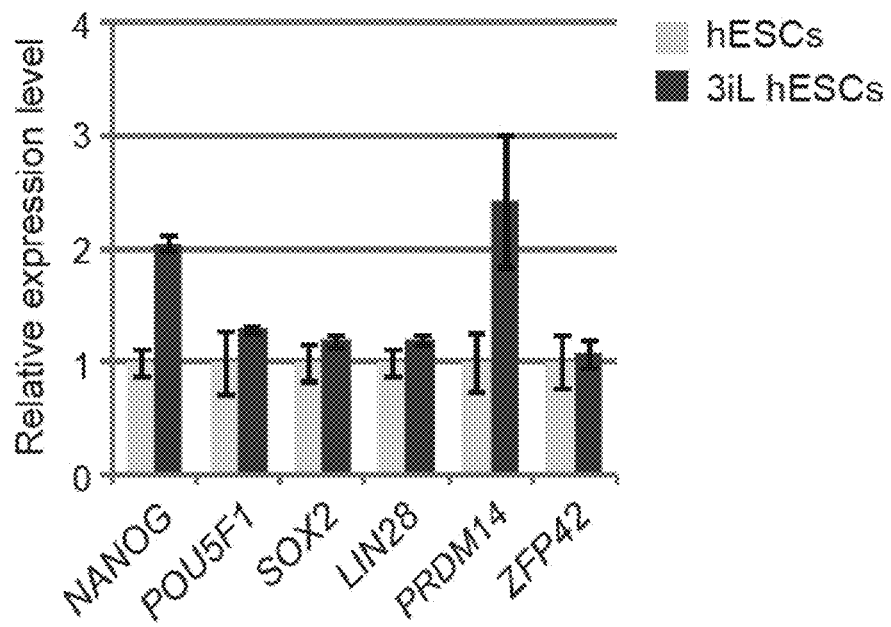
Figure 6:
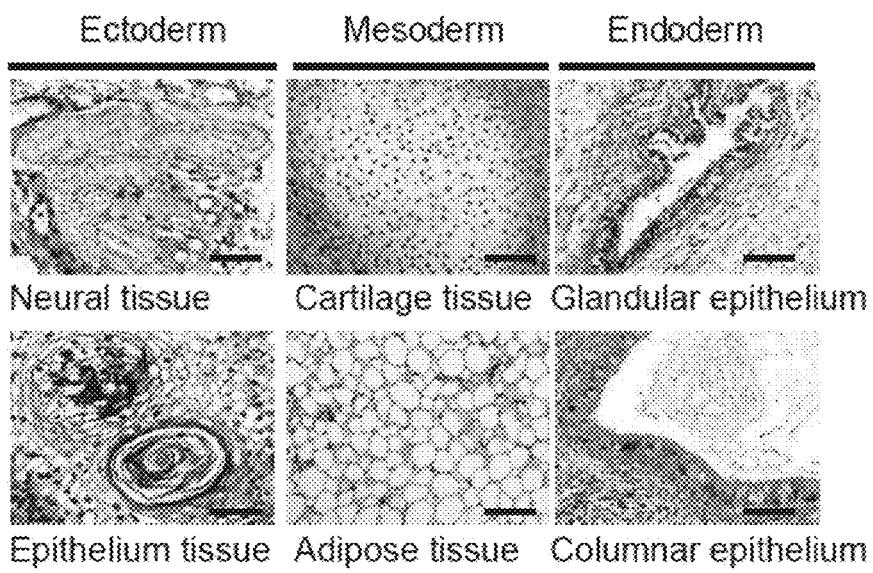
Figure 6:
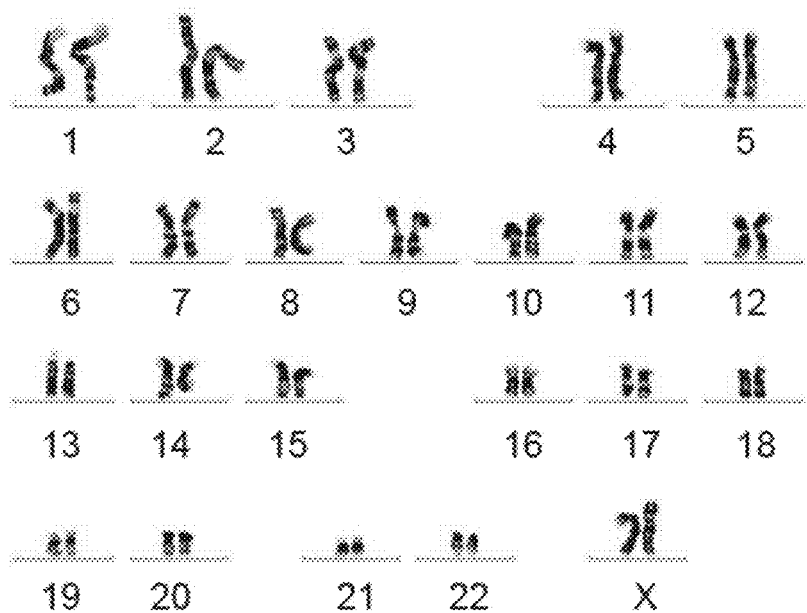
Figure 6:
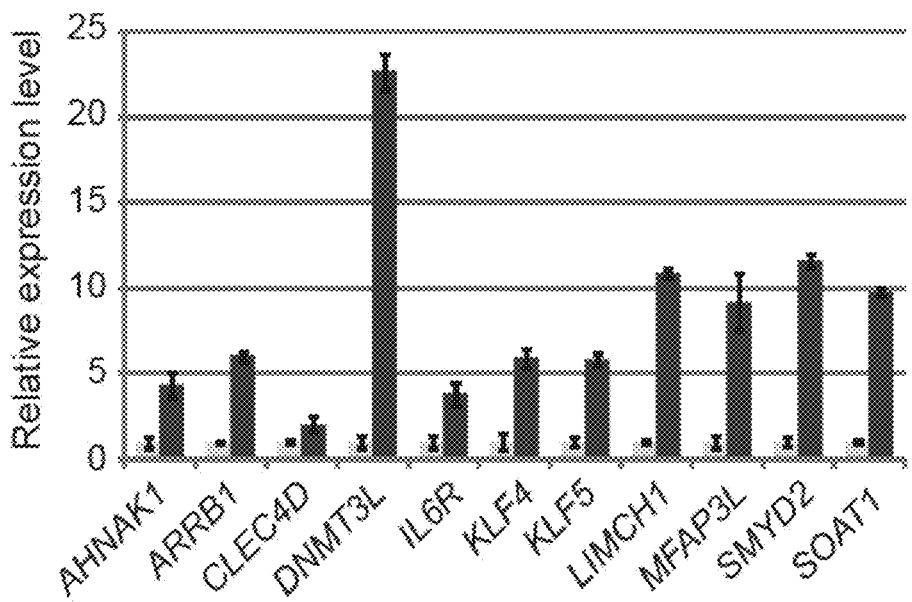
Figure 6:
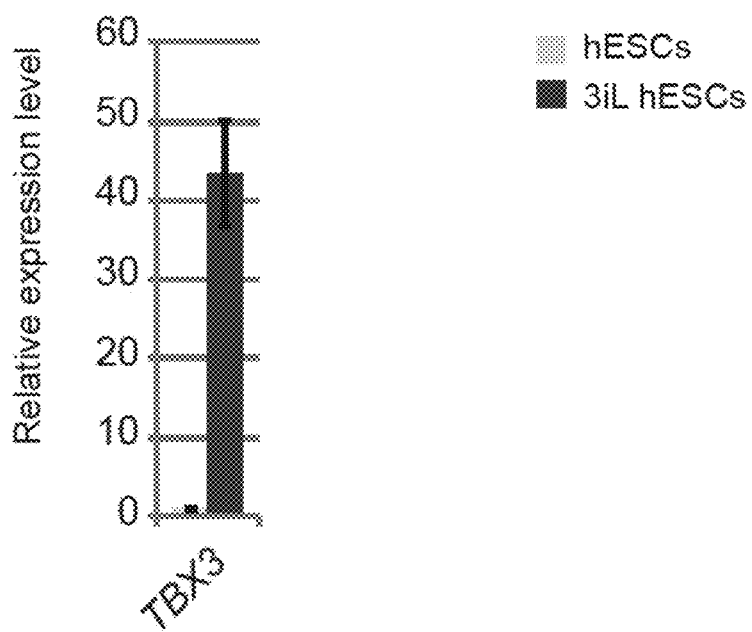
Figure 6:
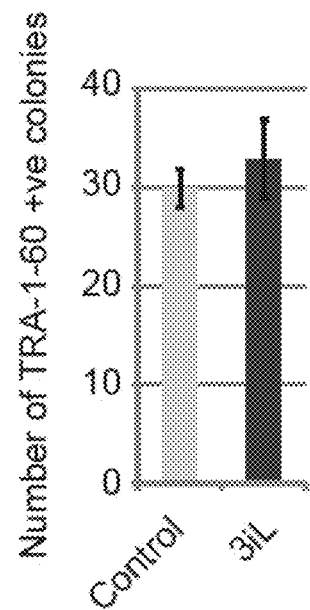
Figure 6:
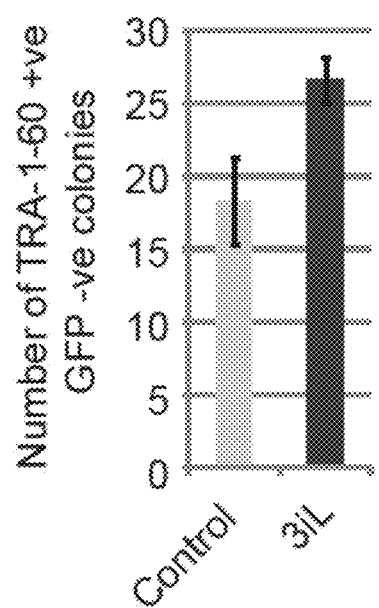
Figure 6:
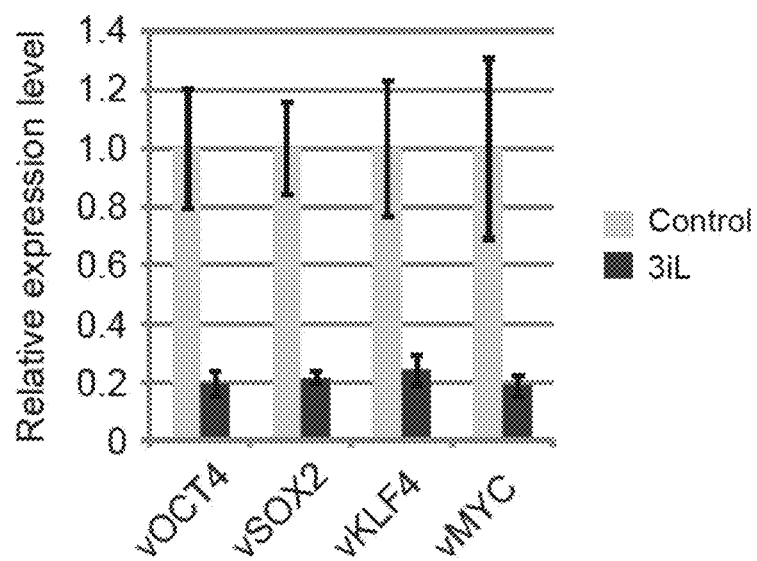
Figure 6:
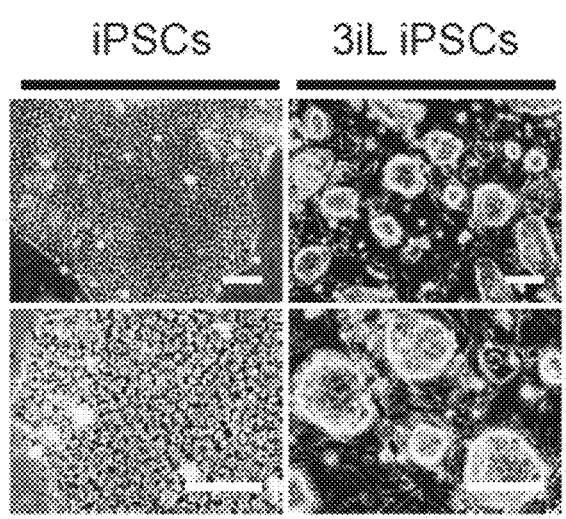
Figure 6:
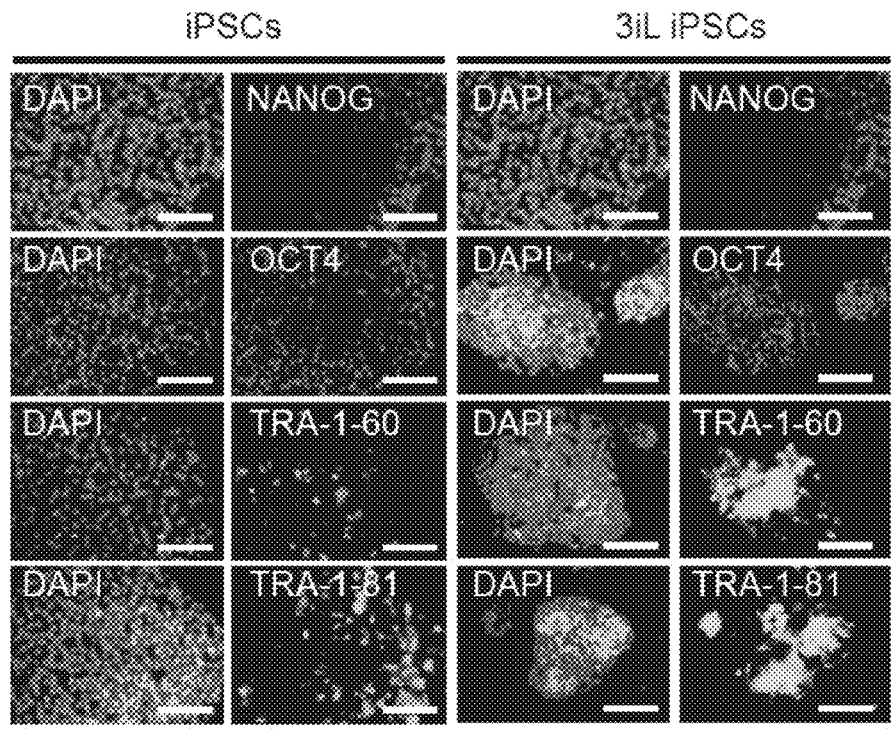
Figure 6:
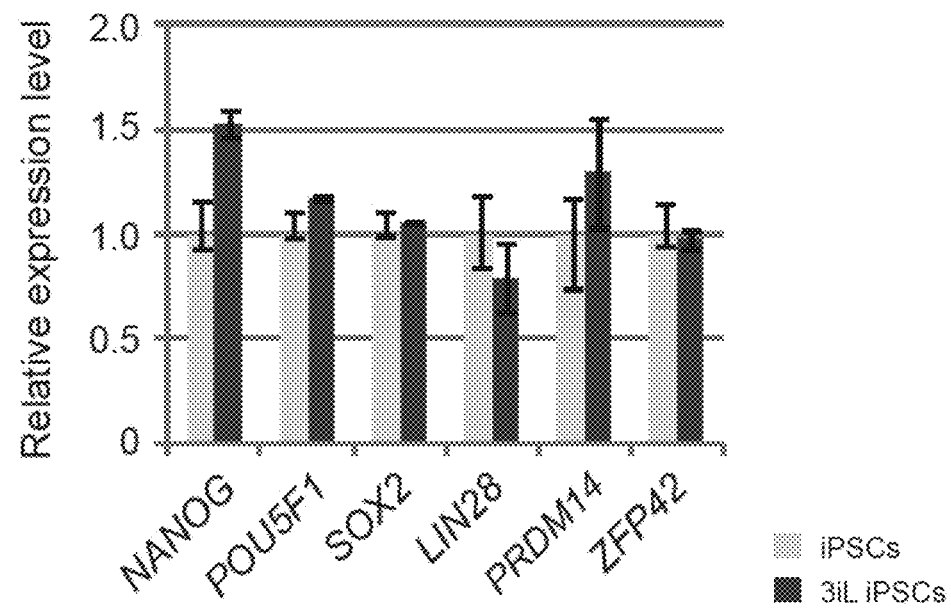
Figure 6:
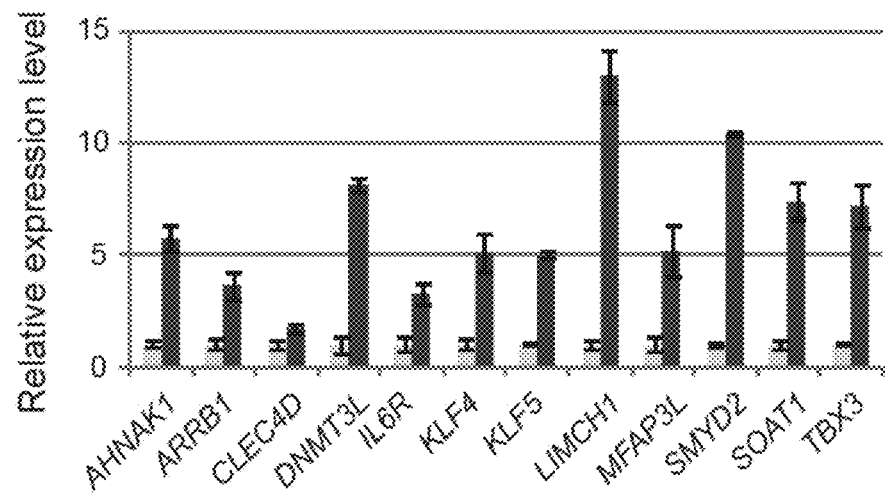

FIG. 6. 3iL culture conditions support the stable culture of other hESC cell lines and iPSC.
A) Morphology of hES3 hESCs and hES3-derived 3iL hESCs. Scale bar represents 200 µm.
B) Staining of hES3 hESCs and hES3-derived 3iL hESCs for pluripotency markers NANOG and OCT4, and cell surface markers TRA-1-60 and TRA-1-81. Scale bar represents 200 µm.
C) hES3-derived 3iL hESCs express higher levels of NANOG as compared to hES3 hESCs. All values are mean±s.d from 3 independent experiments.
D) hES3-derived 3iL hESCs form teratomas when injected into SCID mice. Shown are teratoma sections containing tissues which are representative of all three embryonic germ layers. Scale bar represents 50 µm.
E) hES3-derived 3iL hESCs exhibit normal karyotype after 2 months in culture.
F) Expression of epiblast-specific genes (Yan et al., 2013) in hES3-derived 3iL hESCs. Epiblast-specific genes are upregulated in 3iL hESCs as compared to hESCs. All values are mean±s.d from 3 independent experiments.
G) Morphology of hES2 hESCs and hES2-derived 3iL hESCs. Scale bar represents 200 µm.
H) Staining of hES2 hESCs and hES2-derived 3iL hESCs for pluripotency markers NANOG and OCT4, and cell surface markers TRA-1-60 and TRA-1-81. Scale bar represents 200 µm.
I) hES2-derived 3iL hESCs express higher levels of NANOG as compared to hES2 hESCs. All values are mean±s.d from 3 independent experiments.
J) hES2-derived 3iL hESCs form teratomas when injected into SCID mice. Shown are teratoma sections containing tissues which are representative of all three embryonic germ layers. Scale bar represents 50 µm.
K) hES2-derived 3iL hESCs exhibit normal karyotype after 2 months in culture.
L) Expression of epiblast-specific genes in hES2-derived 3iL hESCs. Epiblast-specific genes are upregulated in 3iL hESCs as compared to hESCs. All values are mean±s.d from 3 independent experiments.
M) Human MRC5 fibroblasts were retrovirally transduced with the four Yamanaka reprogramming factors (OCT4, SOX2, KLF4 and MYC) and pMX-GFP. After 3 weeks, cells were treated with either standard medium or 3i+LIF medium. After 1 week of treatment, the number of TRA-1-60 colonies was counted.
N) The 3iL treatment (see M) resulted in a higher number of TRA-1-60 positive colonies that are also GFP negative, indicating that more high quality iPSC colonies were obtained after the 3iL treatment.
O) Quantitative PCR data showing a greater downregulation of viral transgenes in the iPSCs cultured in 3iL condition. All values are mean±s.d from 3 independent experiments.
P) Morphology of a previously characterized human iPSCs after passages in 3iL culture condition. Scale bar represents 200 µm.
Q) Staining of human iPSCs and the same cells cultured in 3iL condition for 6 passages for pluripotency markers NANOG and OCT4, and cell surface markers TRA-1-60 and TRA-1-81. Scale bar represents 200 µm.
R) Expression of epiblast-specific genes in the 3iL hiPSCs. Epiblast-specific genes are upregulated in 3iL hiPSCs as compared to iPSCs. All values are mean±s.d from 3 independent experiments.

Figure 7:
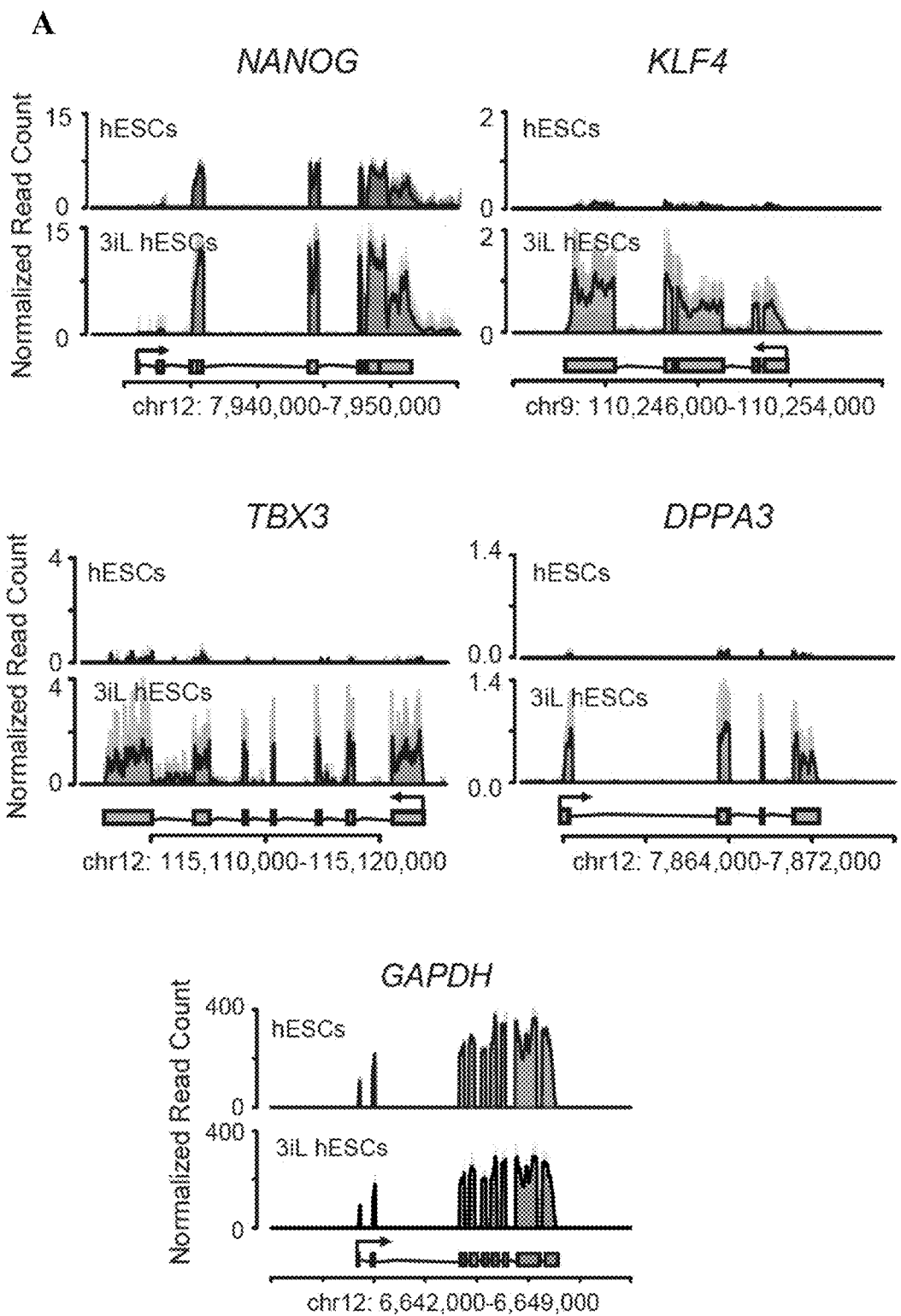
Figure 7:
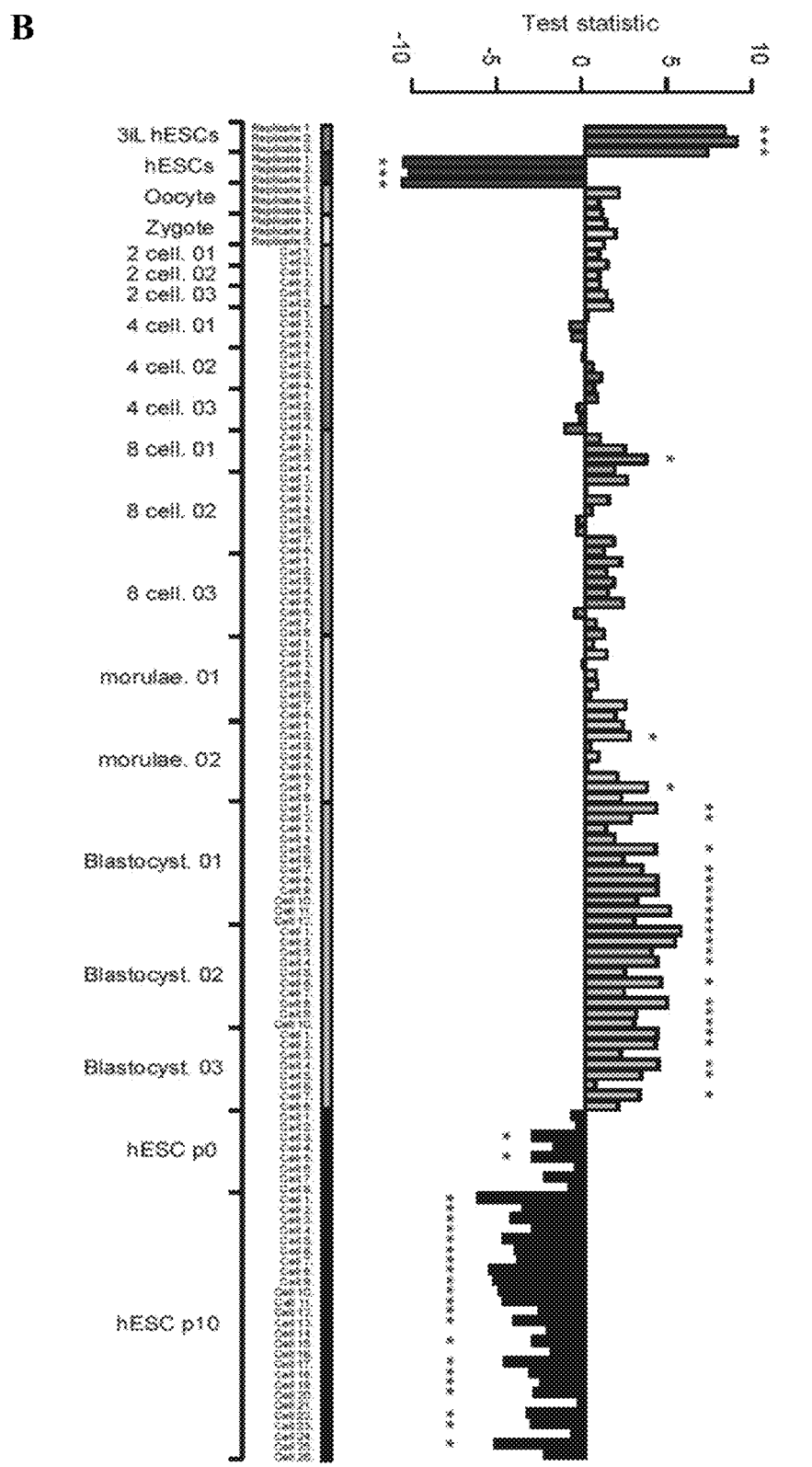
Figure 7:
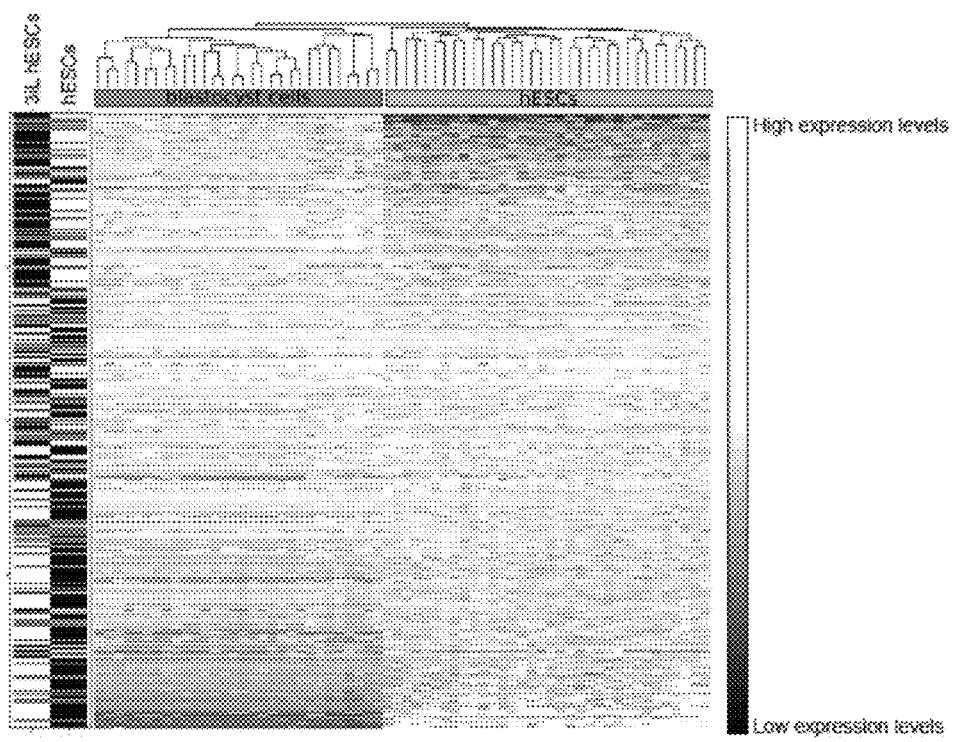
Figure 7:
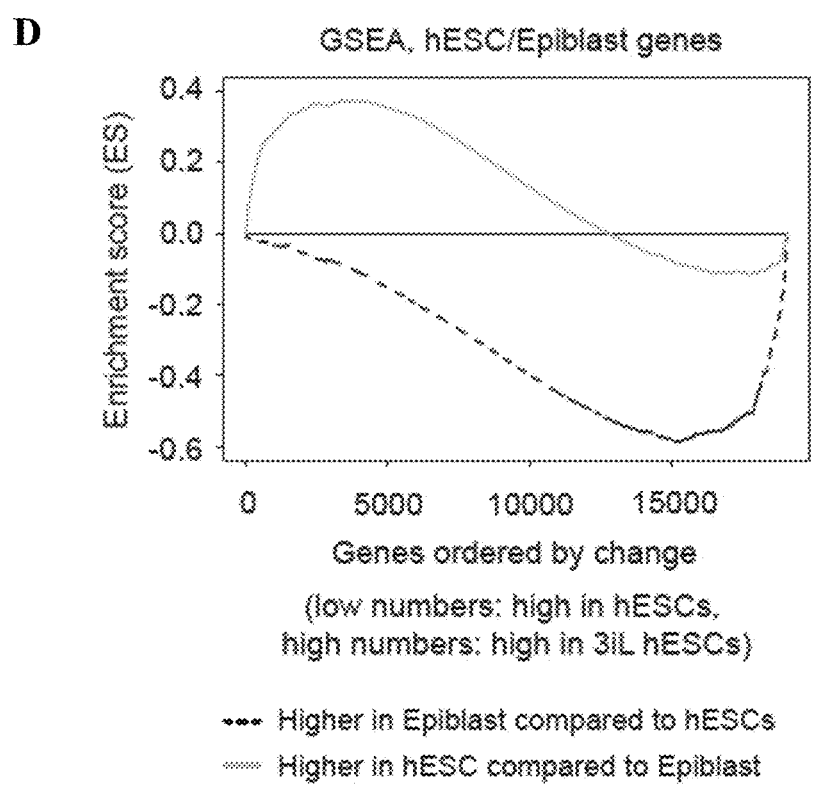
Figure 7:
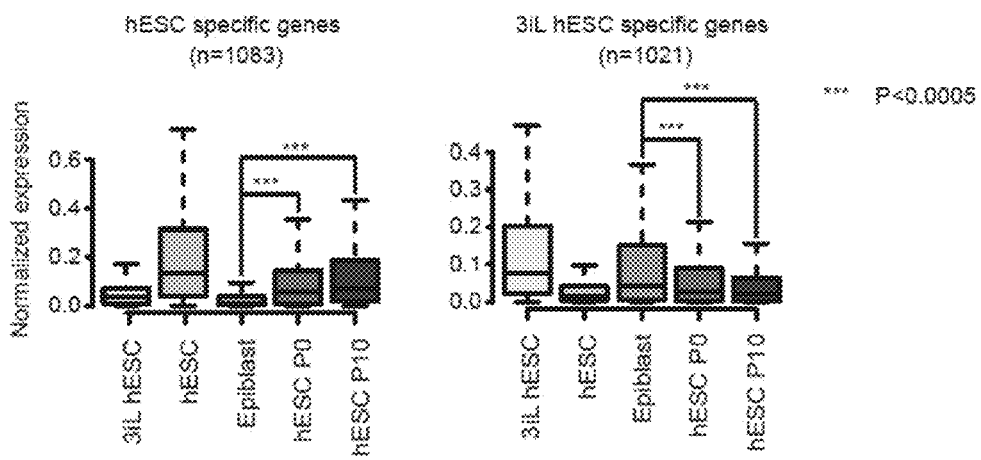
Figure 7:
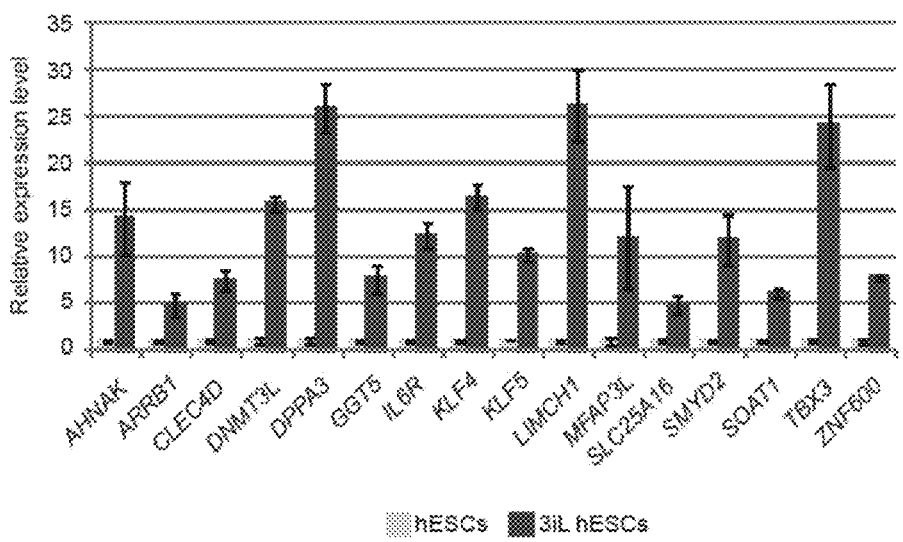

FIG. 7. The transcriptome of 3iL hESCs resembles in vivo preimplantation epiblast.
A) The normalized RNA-Seq read count of NANOG, KLF4, TBX3, DPPA3 and GAPDH in hESCs and 3iL hESCs. The black line shows the mean of three replicates, the individual replicates are shown in shades of grey respectively (overlayed). Read counts were normalized by the number of mapped reads for every replicate. Coordinates are for human genome version hg19.
B) Comparison of expression of 3iL-specific genes with expression of hESC-specific genes in pre-implantation embryos. Shown is the test statistic from an unpaired t-test, positive values indicate that 3iL-specific genes show higher expression than hESC-specific genes and vice versa for negative values. Significant differences (multiple testing adjusted p-value<0.05) are marked with *. The data was normalized per sample and gene prior to testing.
C) Heatmap showing single cell gene expression from pre-implantation blastocyst and hESCs for genes which are differentially expressed between 3iL hESCs and hESCs. Clustering was done on this set of genes using hierarchical clustering. Genes are sorted by the fold change of average expression between blastocyst and hESCs (black to white scale bar). Differentially expressed genes (3iL hESCs vs. hESCs) are marked by black lines.
D) Gene Set Enrichment Analysis (GSEA). Genes were ranked according to the fold change in expression between 3iL hESCs and hESCs. Shown is the enrichment for genes which are differentially expressed in hESCs and human epiblast. Genes that show increased expression in 3iL hESCs are enriched in the set of epiblast-specific genes (dotted line, Wilcoxon rank-sum test p-value=1.03e-48), whereas genes that show increased expression in conventional hESCs are enriched in the set of genes that show higher expression in hESCs compared to human epiblast (solid line, p-value=1.61e-20).

E) Normalized expression of hESC-specific genes and 3iL hESC-specific genes in 3iL hESCs, hESCs, human pre-implantation epiblast (average from single cell data), hESCs passage 0 (average from single cell data), hESCs passage 10 (average from single cell data). P-values were calculated using a paired t-test. The number of genes corresponds to genes which are differentially expressed in 3iL hESCs and hESCs and where expression is previously provided.

F) Real time qPCR validation of epiblast-specific genes that are upregulated in 3iL hESCs compared to hESCs. All values are mean±s.d from 3 independent experiments.

Figure 8:
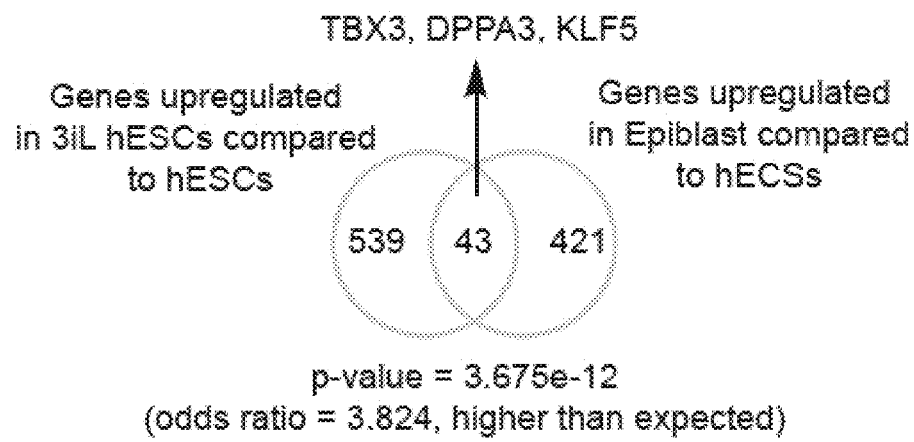
Figure 8:
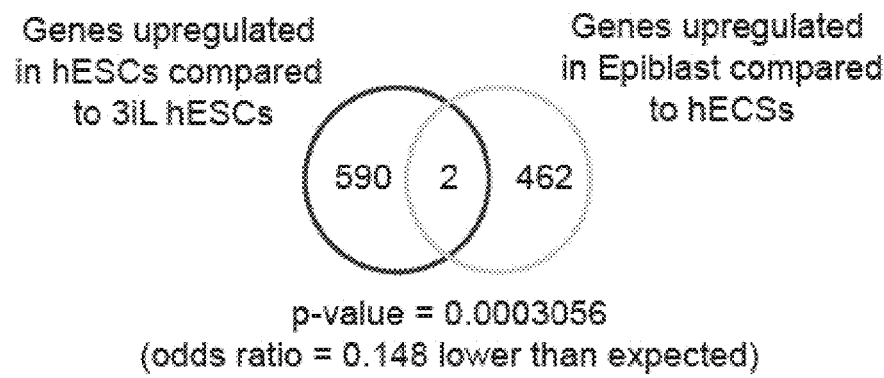
Figure 8:
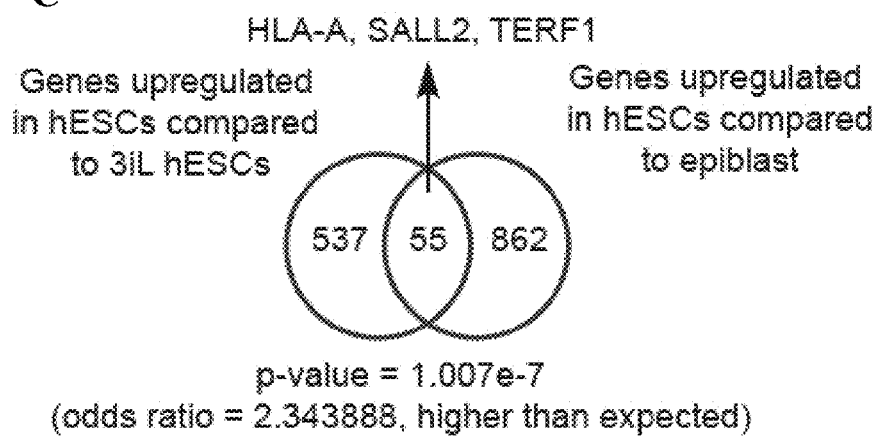
Figure 8:
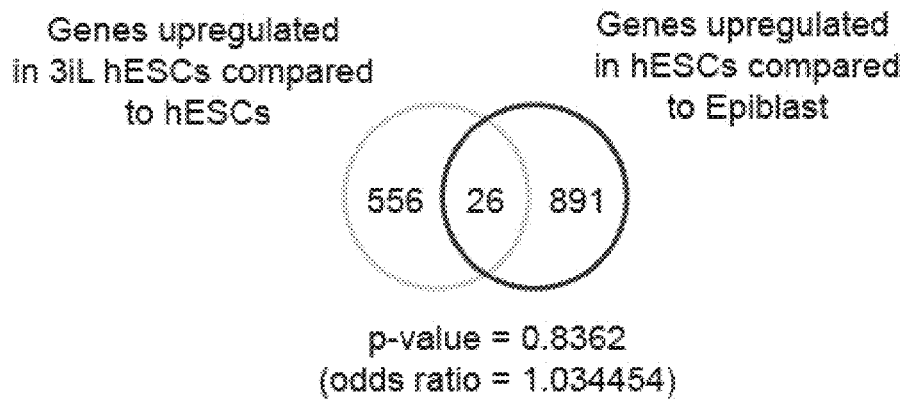
Figure 8:
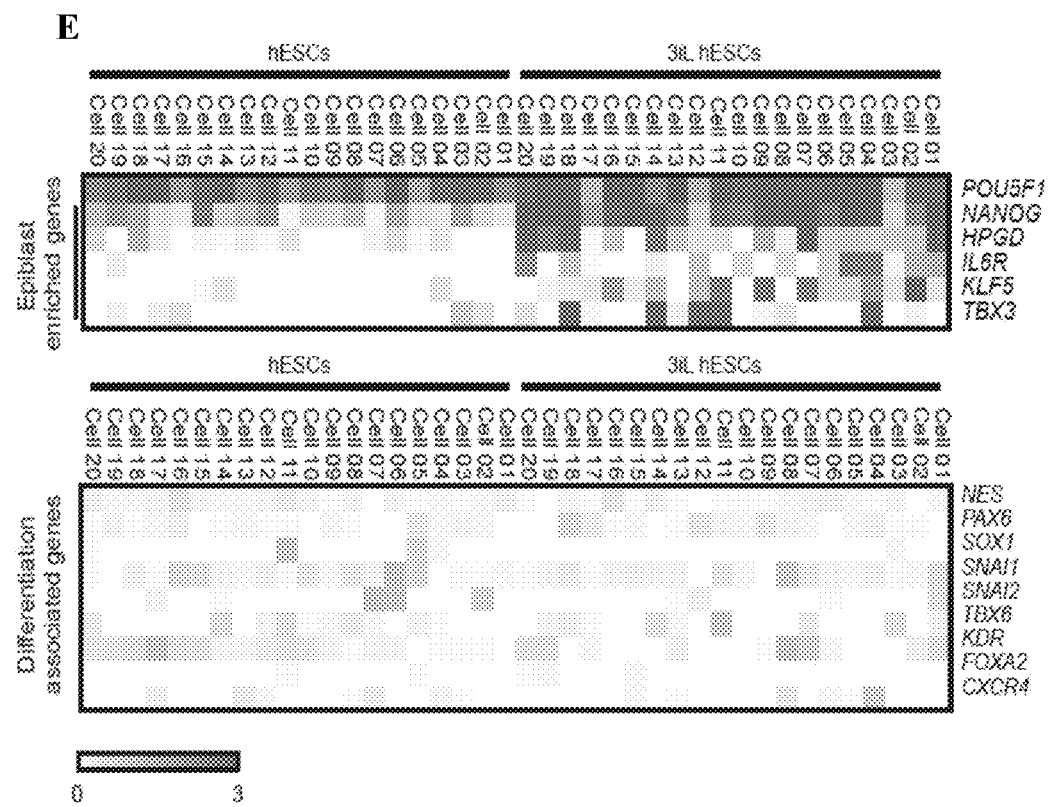
Figure 8:
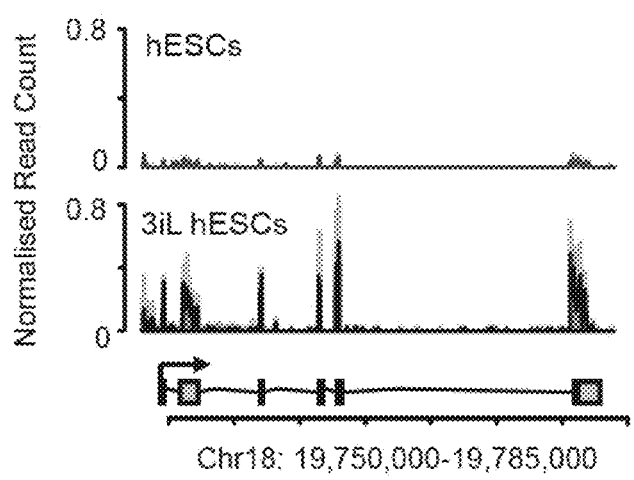
Figure 8:
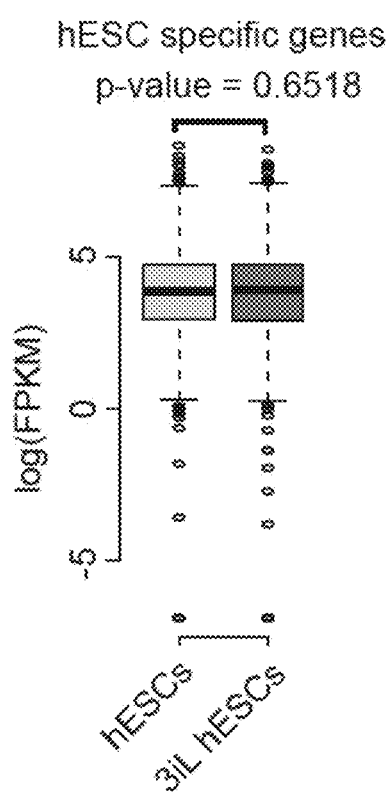
Figure 8:
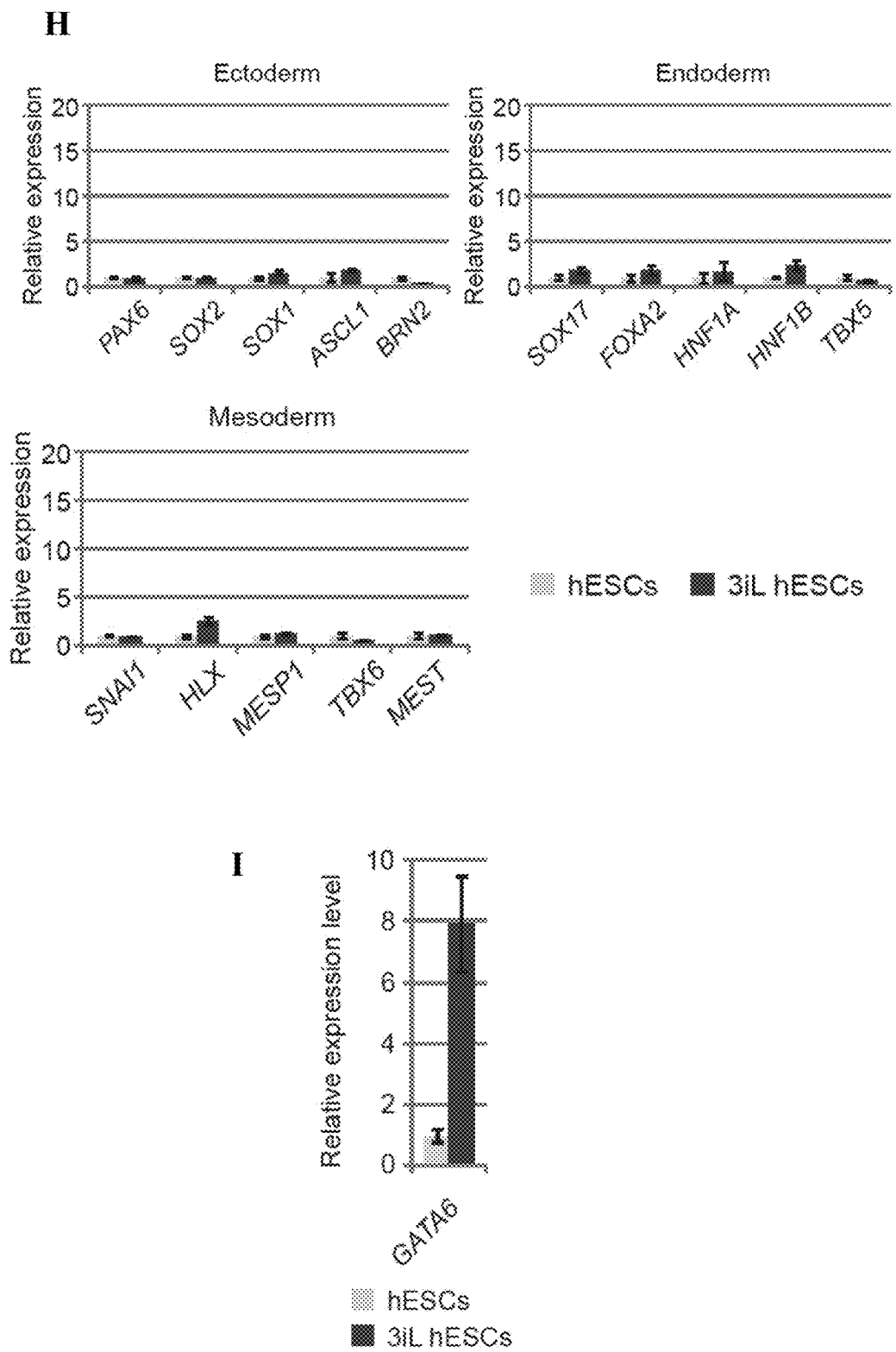
Figure 8:
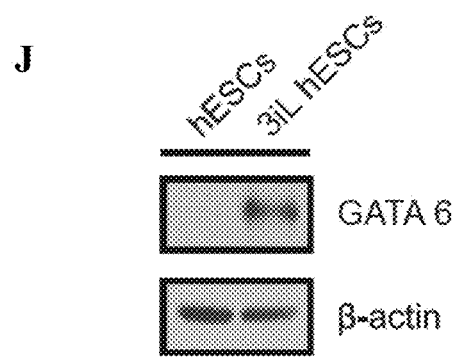
Figure 8:
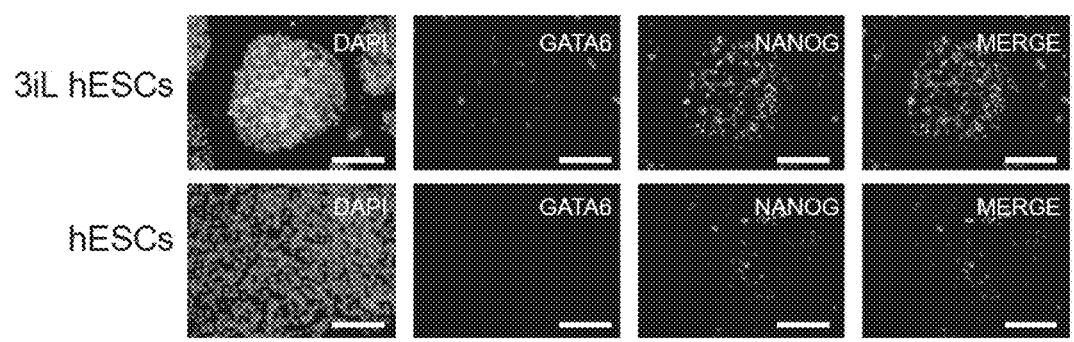
Figure 8:
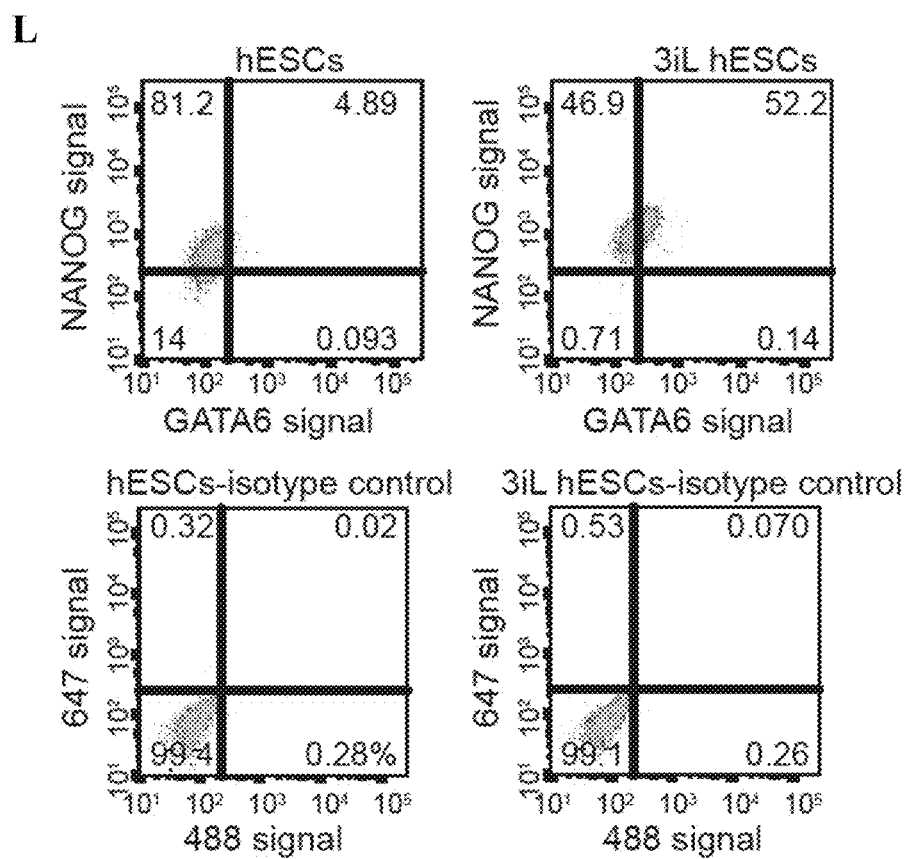
Figure 8:
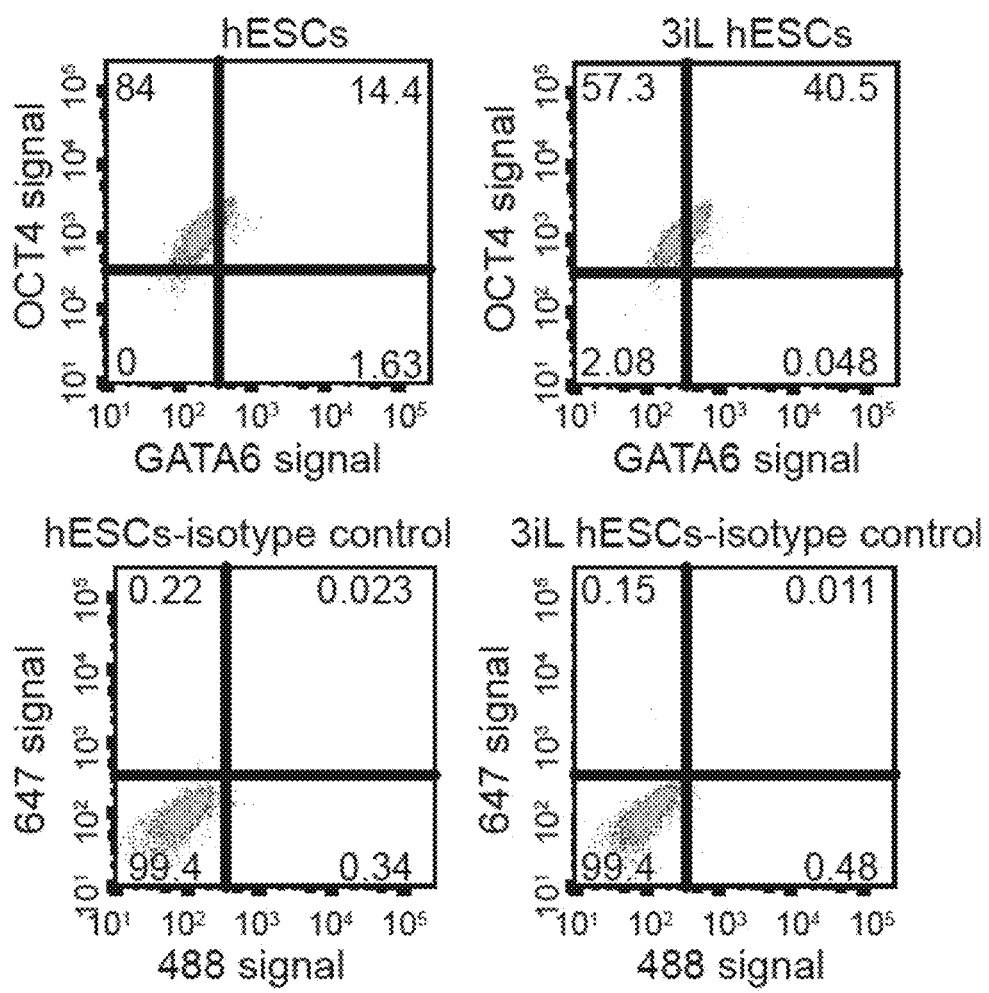
Figure 8:
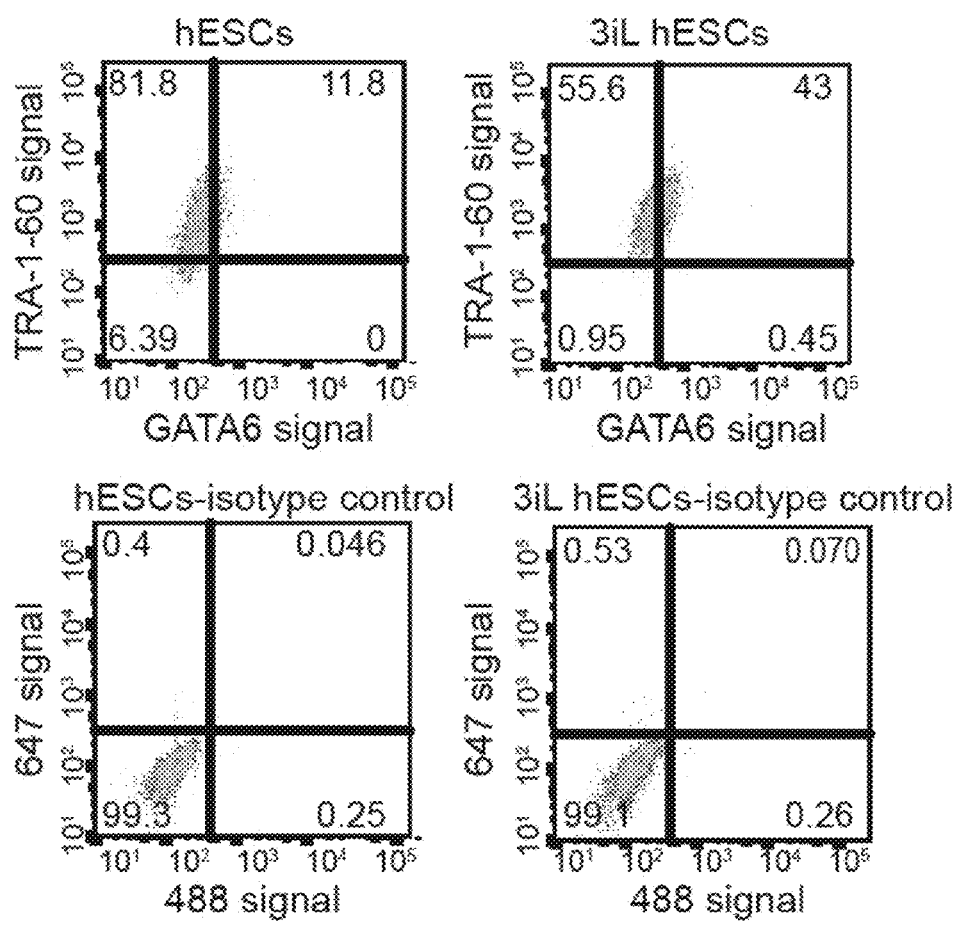
Figure 8:
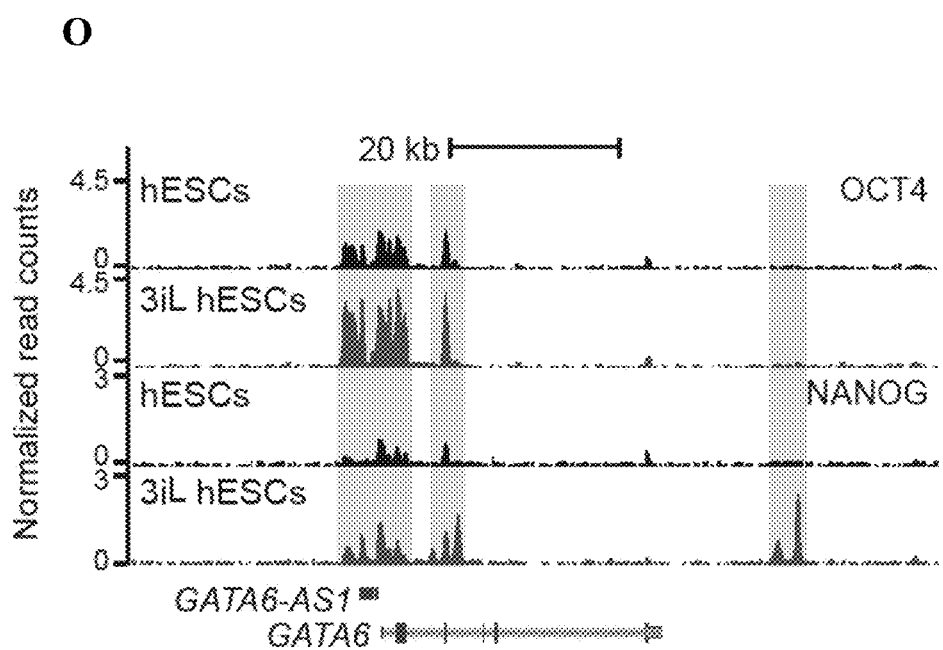

FIG. 8. Expression of native epiblast markers and GATA6 in 3iL cultured hESCs.

A) Overlap of genes that show increased expression in 3iL hESCs as compared to hESCs with genes that show increased expression in Epiblast cells as compared to hESCs. Significance score was determined using Fisher's exact test.

B) Overlap of genes that show decreased expression in 3iL hESCs as compared to hESCs with genes that show increased expression in Epiblast cells as compared to hESCs. Significance score was determined using Fisher's exact test.

C) Overlap of genes that show decreased expression in 3iL hESCs as compared to hESCs with genes that show decreased expression in Epiblast cells as compared to hESCs. Significance score was determined using Fisher's exact test.

D) Overlap of genes that show increased expression in 3iL hESCs compared to hESCs with genes that show decreased expression in Epiblast cells compared to hESCs. Significance score was determined using Fisher's exact test.

E) Single cell gene expression analysis of hESCs and 3iL hESCs. The POU5F1 expression level is comparable between hESCs and 3iL hESCs. There is increased expression of epiblast genes including NANOG in 3iL hESCs, and the data reveals the co-expression of these genes in 3iL hESCs. Differentiation genes are expressed at low and comparable levels in both hESCs and 3iL hESCs.

F) Genomic loci of GATA6 showing the normalized RNA-Seq read count in hESCs and 3iL hESCs. The black line shows the mean of three biological replicates, the individual replicates are shown in shades of grey (overlayed). Read counts were normalized by the number of mapped reads for every replicate, coordinates are for the human genome version hg19.

G) Log transformed FPKM values for hESC-specific genes in 3iL hESCs and hESCs. Significance was determined using the paired Wilcoxon test.

H) Quantitative PCR validation of genes associated with ectoderm, endoderm and mesoderm. All values are mean±s.d from 3 independent experiments.

I) Quantitative PCR validation of GATA6 expression in 3iL hESCs. All values are mean±s.d from 3 independent experiments.

J) Protein levels of GATA6 in 3iL hESCs and hESCs. β-actin served as the loading control.

K) Immunofluorescence co-staining of GATA6 and NANOG shows co-expression of these 2 proteins in 3iL hESCs. Scale bar represents 200 µm.

L) FACS analysis of NANOG and GATA6 co-expression in 3iL hESCs and hESCs. Isotype controls are only stained with the secondary antibody.

M) FACS analysis of OCT4 and GATA6 co-expression in 3iL hESCs and hESCs. Isotype controls are only stained with the secondary antibody.

N) FACS analysis of TRA-1-60 and GATA6 co-expression in 3iL hESCs and hESCs. Isotype controls are only stained with the secondary antibody.

O) Binding profiles of OCT4 and NANOG in 3iL hESCs and hESCs. Read counts were normalized by the total number of mapped reads.

Figure 9:
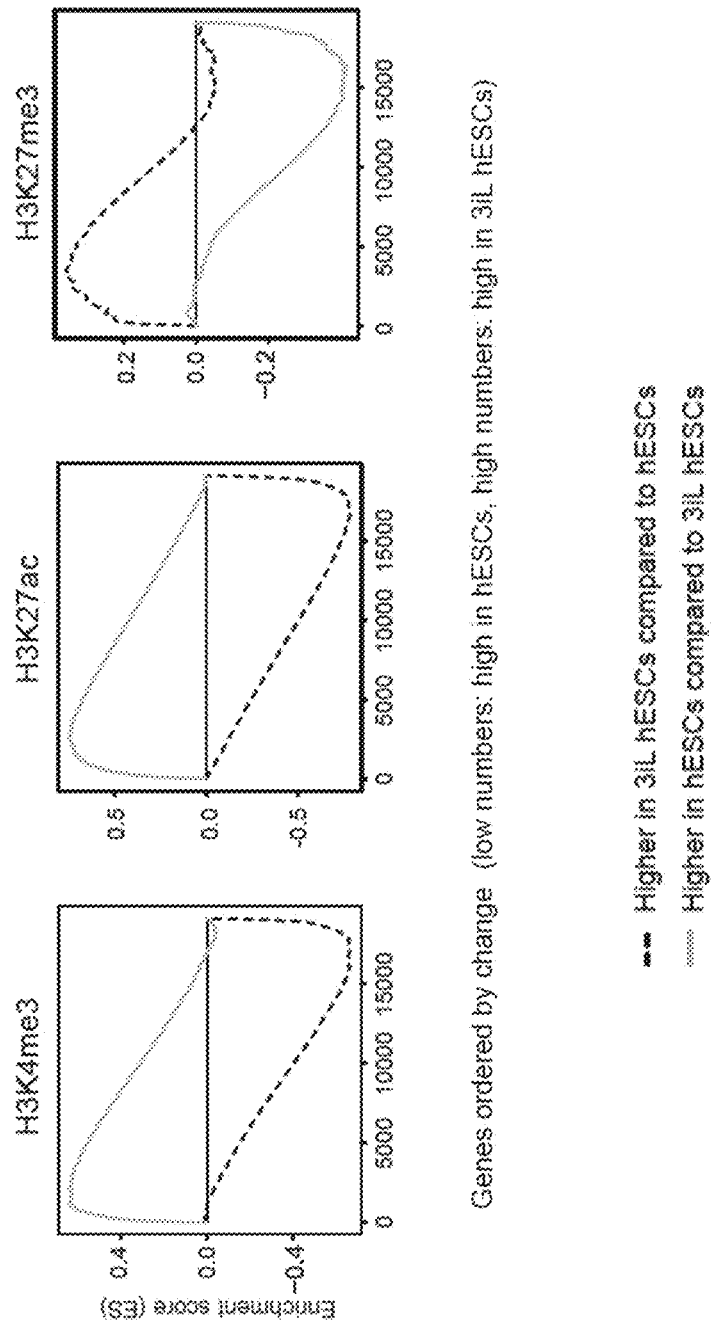
Figure 9:
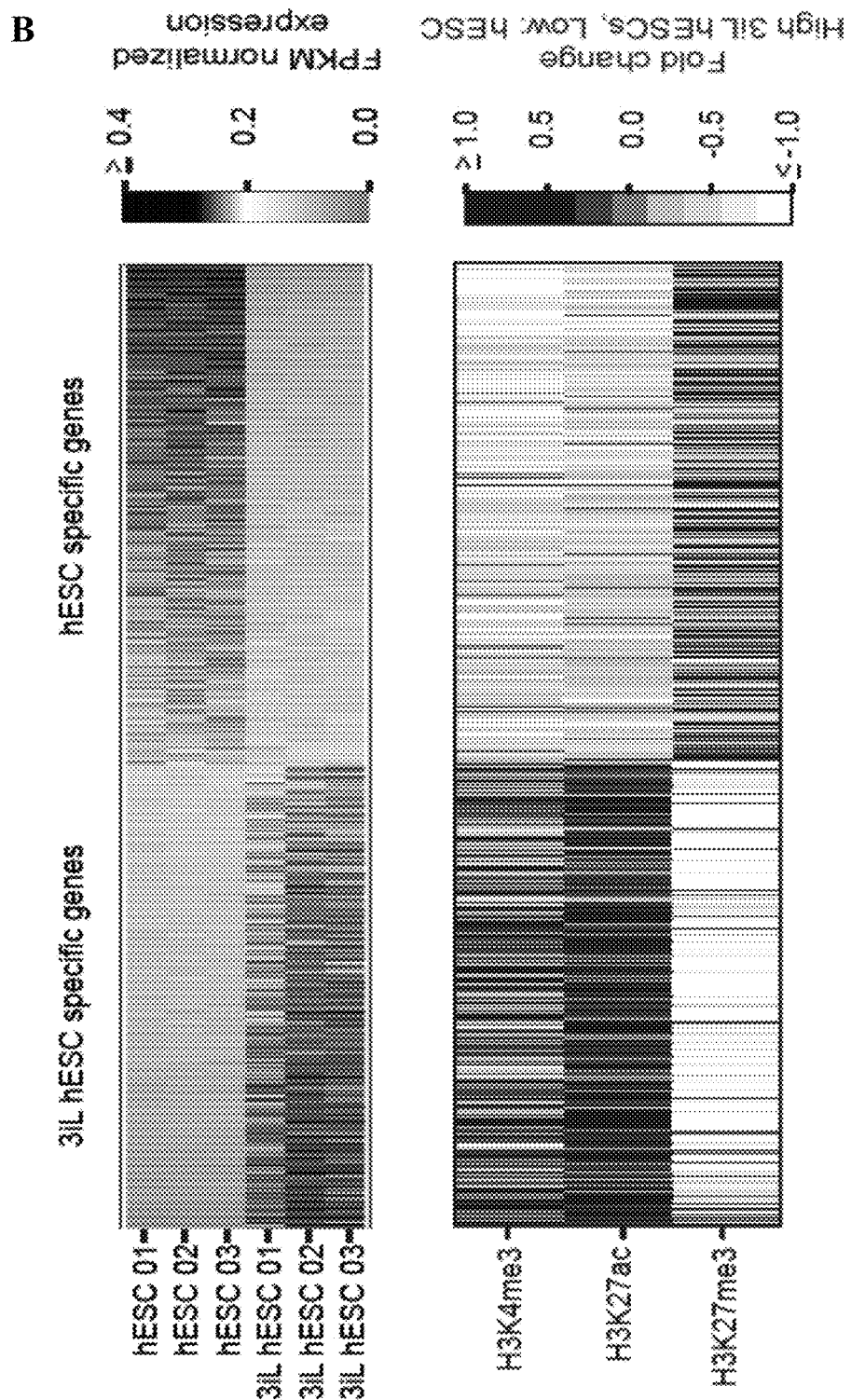
Figure 9:
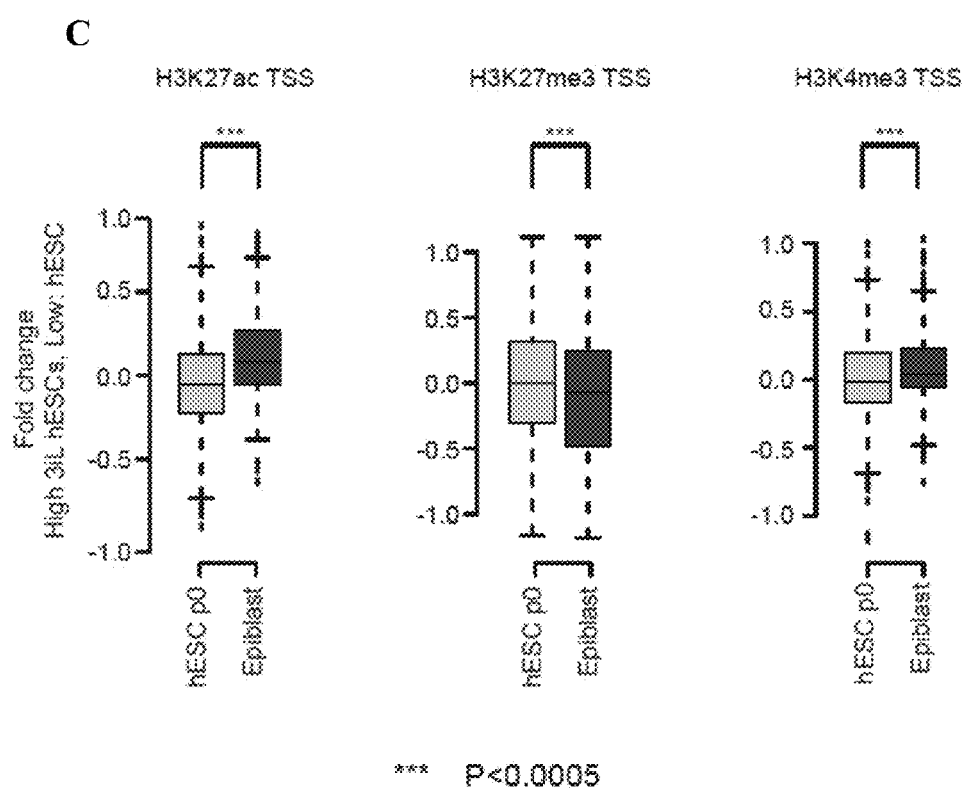
Figure 9:
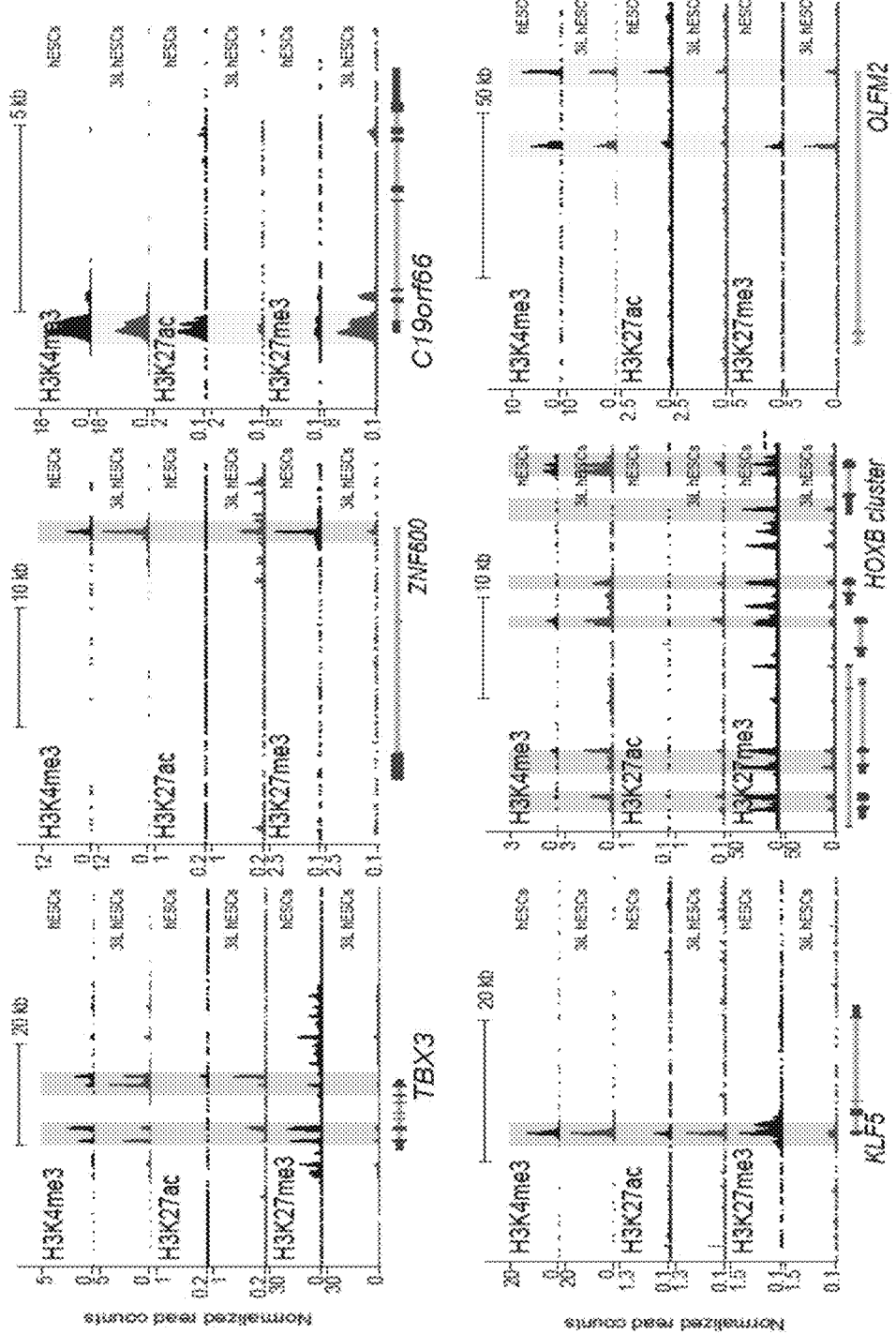

FIG. 9. The epigenomic landscape of 3iL hESCs.

A) GSEA plots showing enrichment of genes that show increase (dotted line) or decrease (solid line) of H3K4me3, H3K27ac and H3K27me3 at promoters in 3iL hESCs compared to hESCs. Genes are ordered by cuffdiff test statistic. Genes that show increased expression in 3iL hESCs are enriched in the set of genes that show increased H3K27ac (Wilcoxon rank-sum test p-value=8.83e-263), increased H3K4me3 (p-value=2.4e-69) and decreased H3K27me3 (p-value=4.90e-92). Genes that show decreased expression in 3iL hESCs are enriched in the set of genes that show decreased H3K27ac (p-value<1.0e-300), decreased H3K4me3 (p-value=3.38e-193) and increased H3K27me3 (p-value=1.44e-12).

B) Fold change of normalized read counts for histone modifications at promoters of differentially expressed genes, estimated using DESeq2 . . . . Genes are ranked by cuffdiff test statistic and normalized per gene.

C) Fold change of normalized read counts for histone modification at promoters (transcription start sites, TSS) of hESC passage 0-specific genes and epiblast specific genes. Significance was estimated using the Wilcoxon rank-sum test.

D) ChIP-Seq profiles of H3K4me3, H3K27ac and H3K27me3 in 3iL hESCs and hESCs. Highlighted regions represent changes in the histone methylation profile observed. For TBX3, ZNF600, KLF5 and HOXB cluster, highlighted regions marked loci with increased H3K27ac and/or decreased H3K27me3 in 3iL hESCs. For C19orf66 and OLFM2, highlighted regions marked loci with decreased H3K27ac and/or increased H3K27me3 in 3iL hESCs. Read counts were normalized by the total number of mapped reads.

Figure 10:
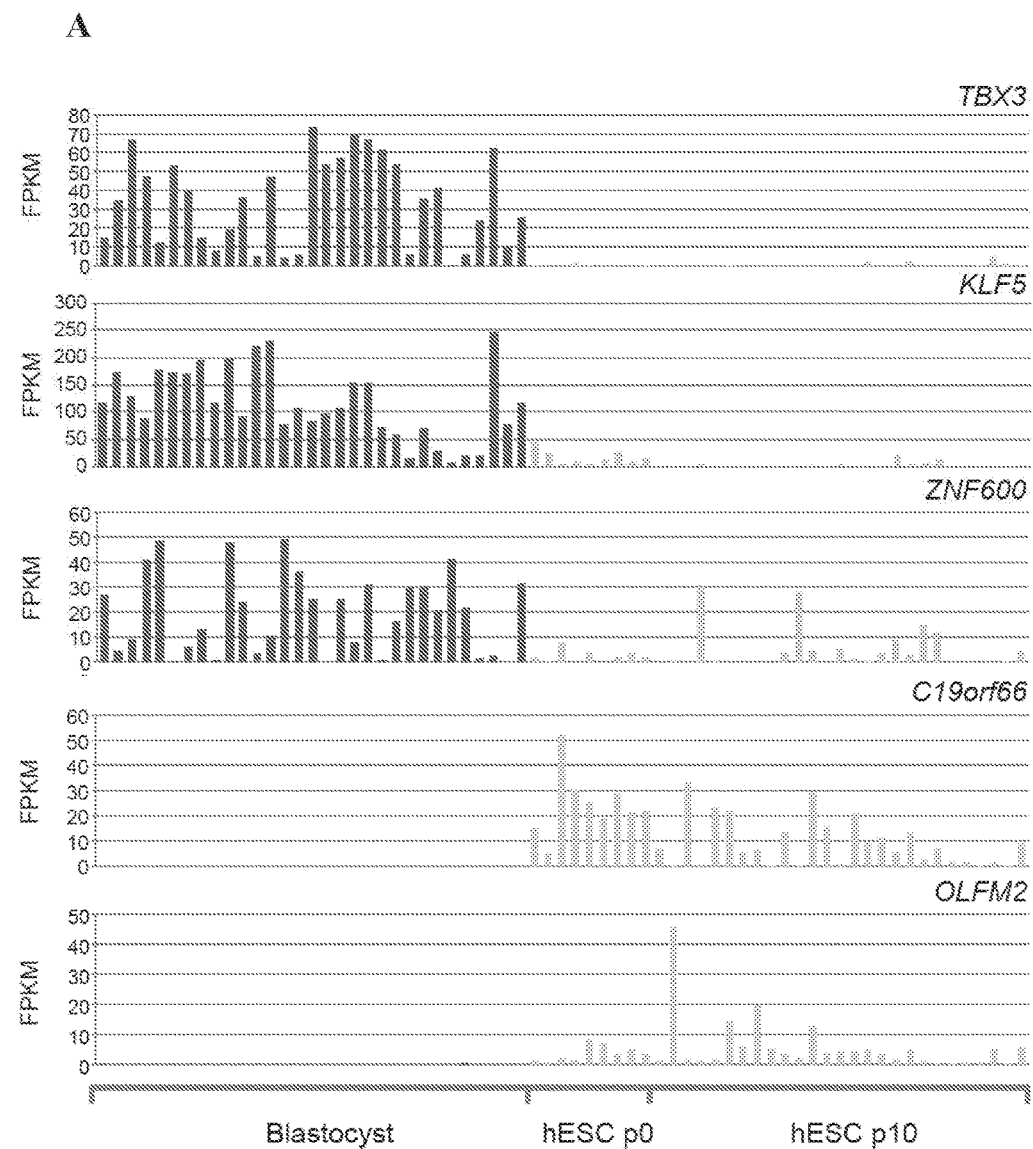

FIG. 10. Expression of selected native epiblast markers in blastocyst cells and hESCs.

A) Average FPKM values for genes that show increased H3K27ac in 3iL hESCs (TBX3, KLF5, ZNF600) and genes that show increased H3K27me3 in 3iL hESCs (C19orf66 and OLFM2) in blastocysts, hESC P0 and hESC P10.

Figure 11:
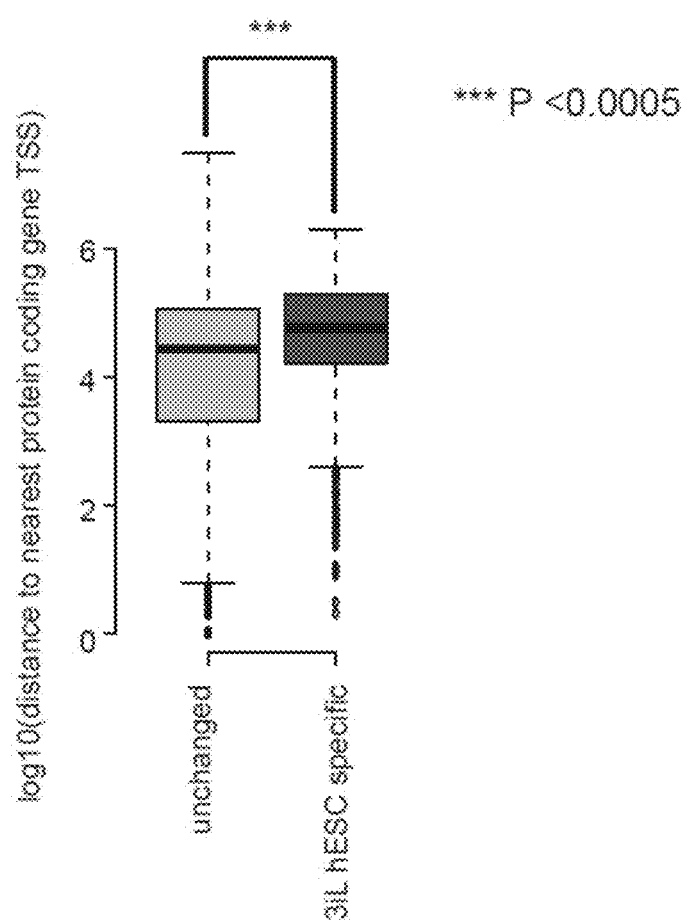
Figure 11:
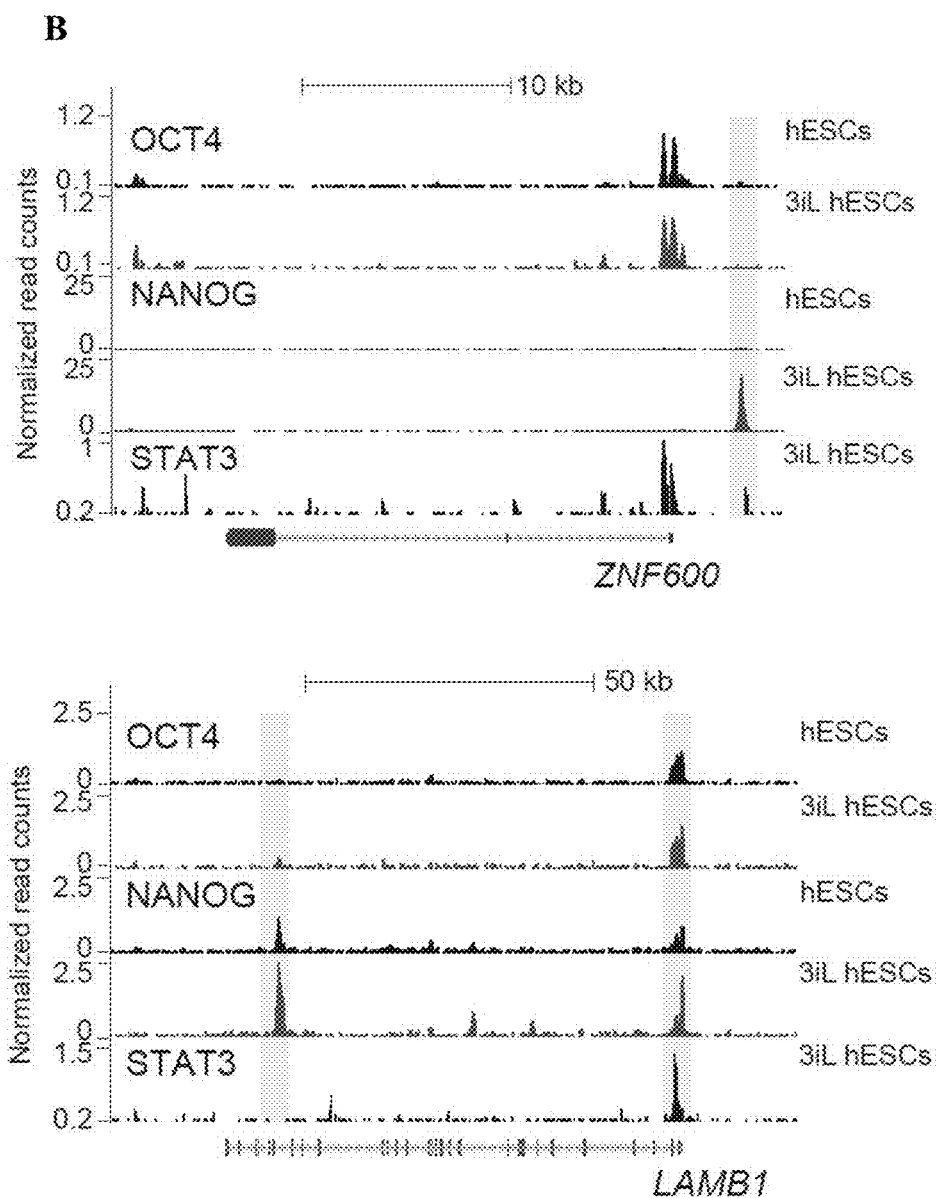

FIG. 11. Novel NANOG and OCT4 binding sites in 3iL hESC.

A) 3iL specific NANOG binding events are significantly more distal to the nearest genes than NANOG binding events which are unchanged. Significance was estimated using the Wilcoxon rank-sum test. p-value=$1.19e^{-166}$.

B) Binding profiles of OCT4, NANOG and STAT3 in 3iL hESCs and hESCs. Highlighted regions marked loci with increased NANOG binding in 3iL hESCs. Read counts were normalized by the total number of mapped reads.

Figure 12:
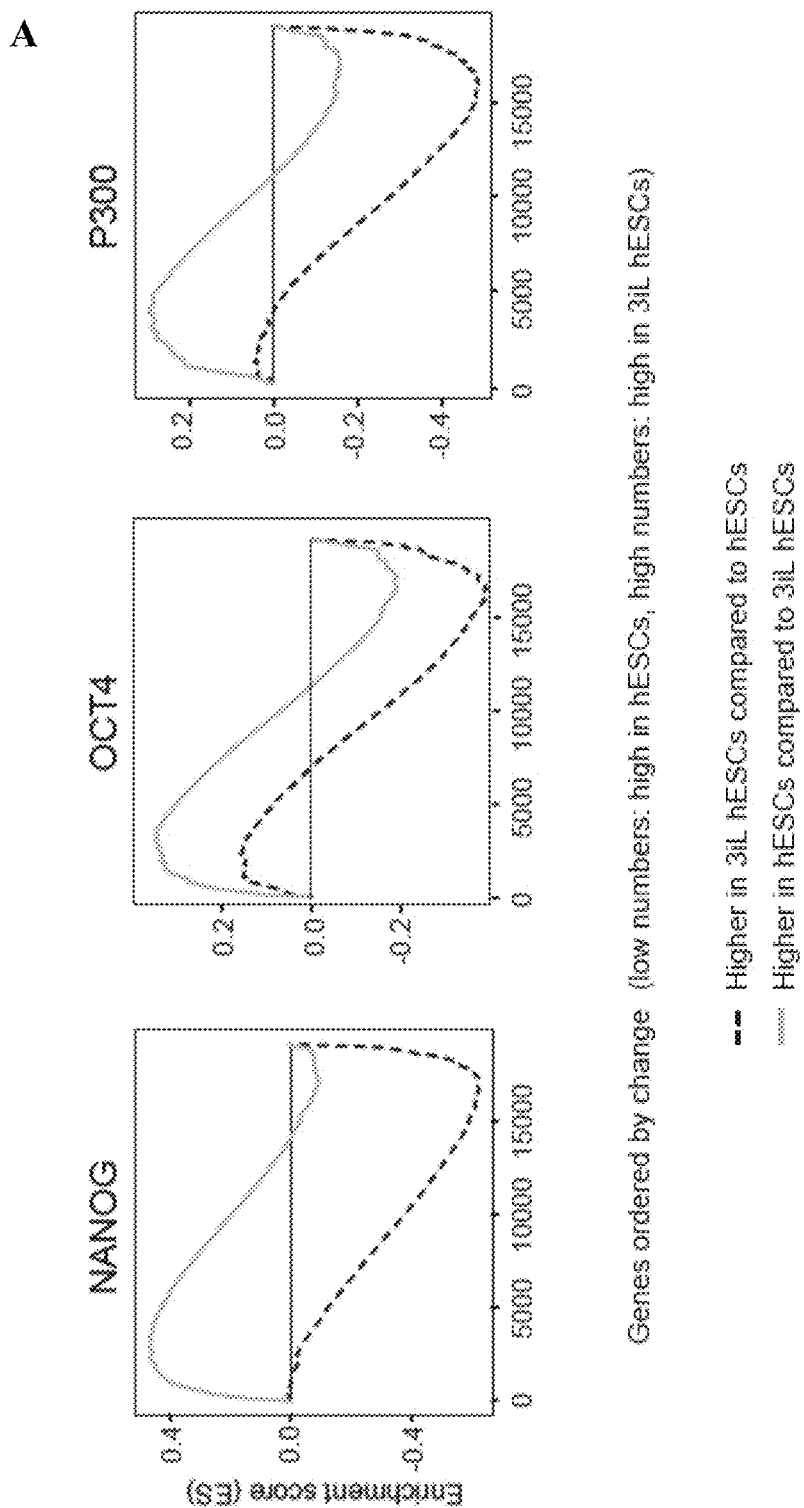
Figure 12:
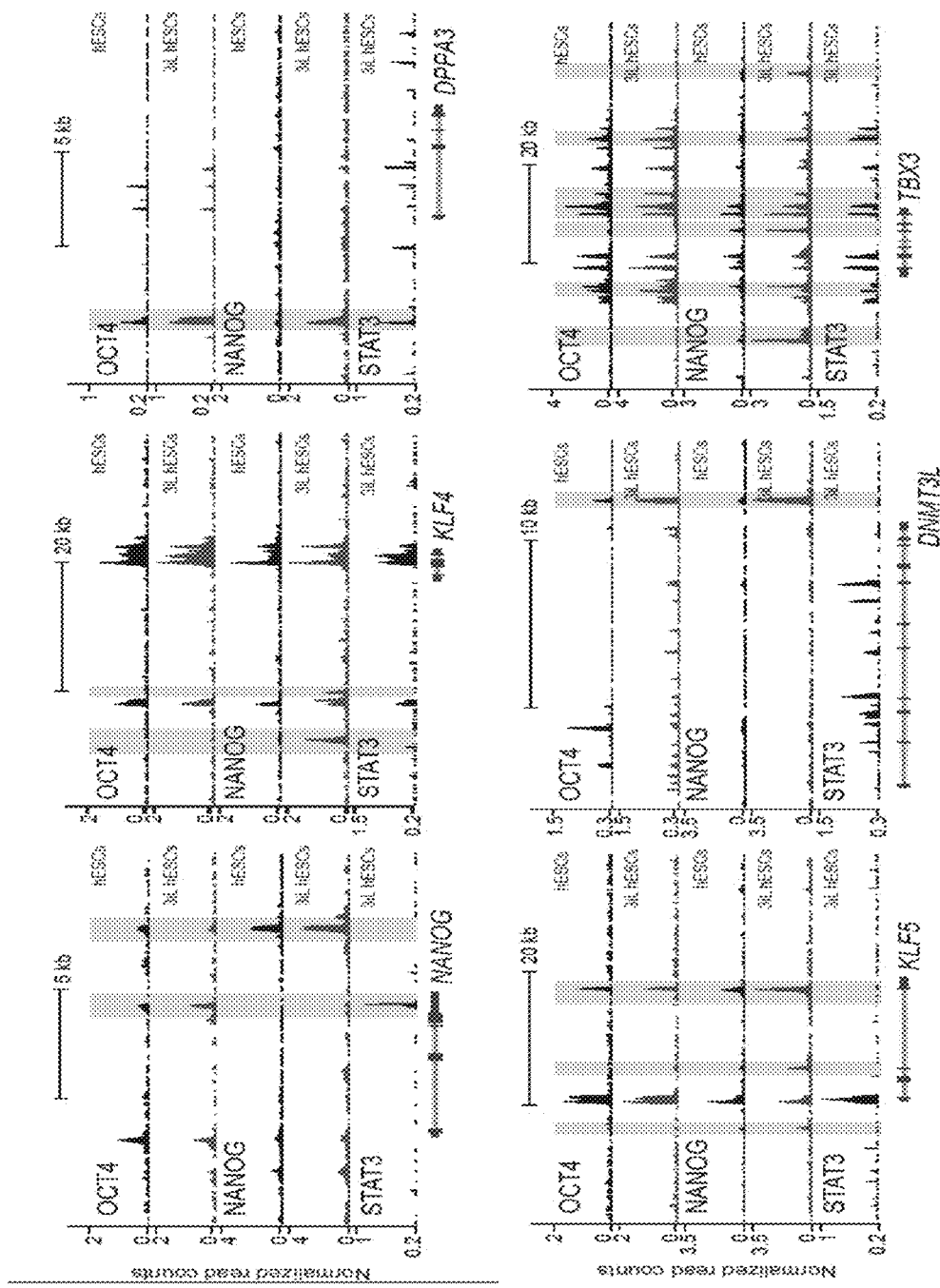
Figure 12:
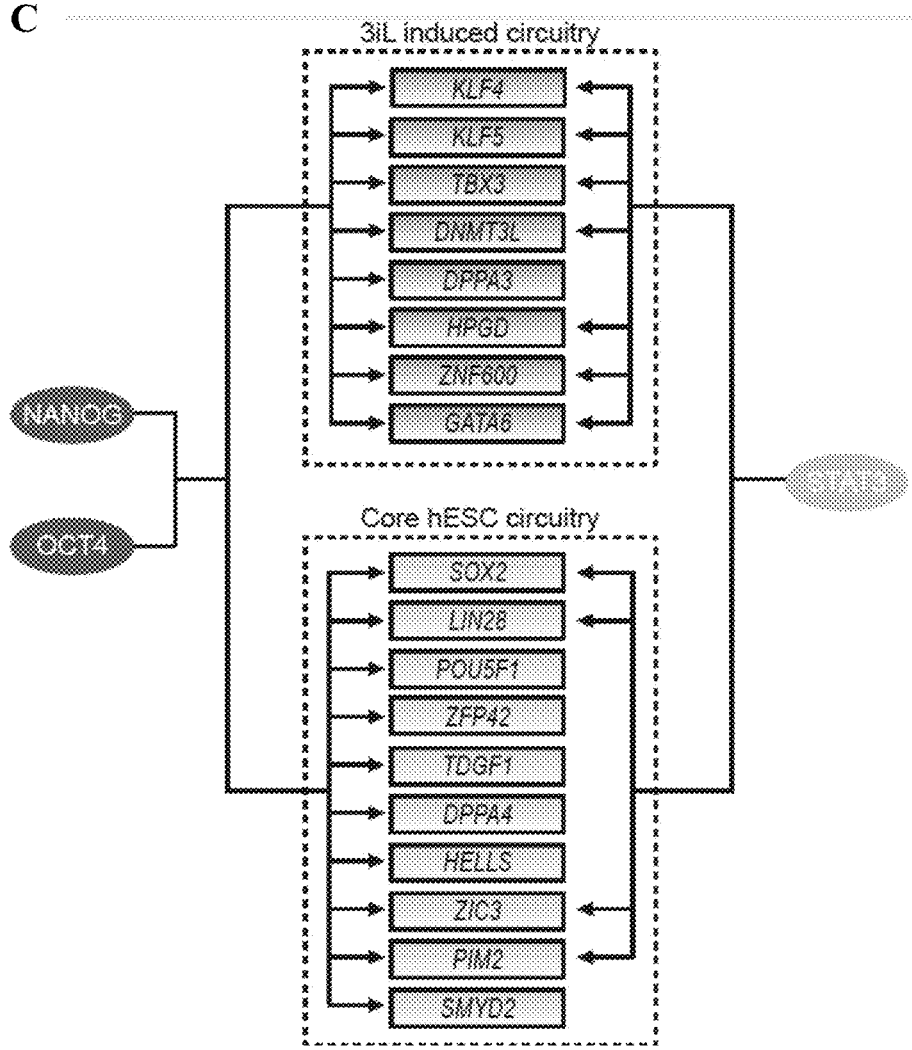
Figure 12:
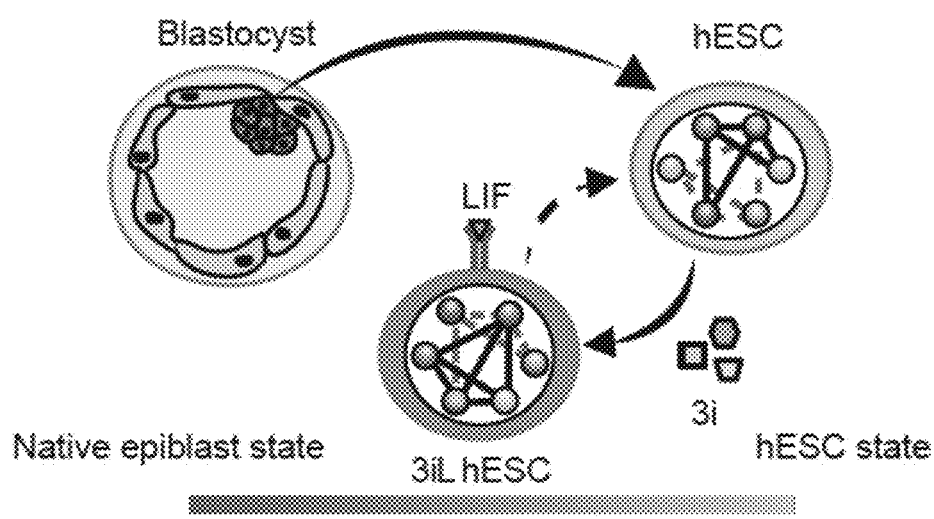

FIG. 12. Re-modeling of the pluripotency transcriptional network in 3iL hESCs.

A) GSEA plots showing enrichment of genes that show increase (dotted line) or decrease (solid line) of NANOG, OCT4 or p300 binding nearby. Genes are ordered by cuffdiff test statistic. Genes that show increased expression in 3iL hESCs are enriched in the set of genes that show increased NANOG binding (Wilcoxon rank-sum test p-value=3.97e-38), OCT4 binding (p-value=4.43e-11) and p300 binding (p-value=8.81e-24). Genes that show decreased expression in 3iL hESCs are enriched in the set of genes that show decreased NANOG binding (p-value=7.16e-06) and decreased OCT4 binding (p-value=5.5e-08).

B) Binding profiles of OCT4, NANOG and STAT3 in 3iL hESCs and hESCs. Highlighted regions marked loci with increased OCT4 and/or NANOG in 3iL hESCs. Read counts were normalized by the total number of mapped reads.

C) A rewired transcriptional circuitry in 3iL hESCs. The 3iL induced circuitry includes genes that are upregulated in 3iL hESCs and are expressed in the native epiblast, amongst others TBX3, DPPA3, KLF5. The core pluripotency circuitry network consisting of genes such as POU5F1 and SOX2 are still part of the new network, highlighting that the 3iL network is rewired, but not replaced. STAT3 also binds to genes of the network (arrows indicated peak with significance score >150), suggesting that the external signaling network potentially cooperates with the transcriptional network to induce a native epiblast signature in 3iL hESCs.

D) 3iL supports a LIF dependent hESC state that more closely resembles the native pre-implantation epiblast state. Each small circles represent transcription factors or cell type specific factors. Full or dotted lines between circles denote the interactions between these factors in regulating different pluripotent states. The gradient of grey from light to dark represents the proximity of 3iL hESC and hESC to the pluripotent epiblast cells of human blastocysts.

Figure 13:
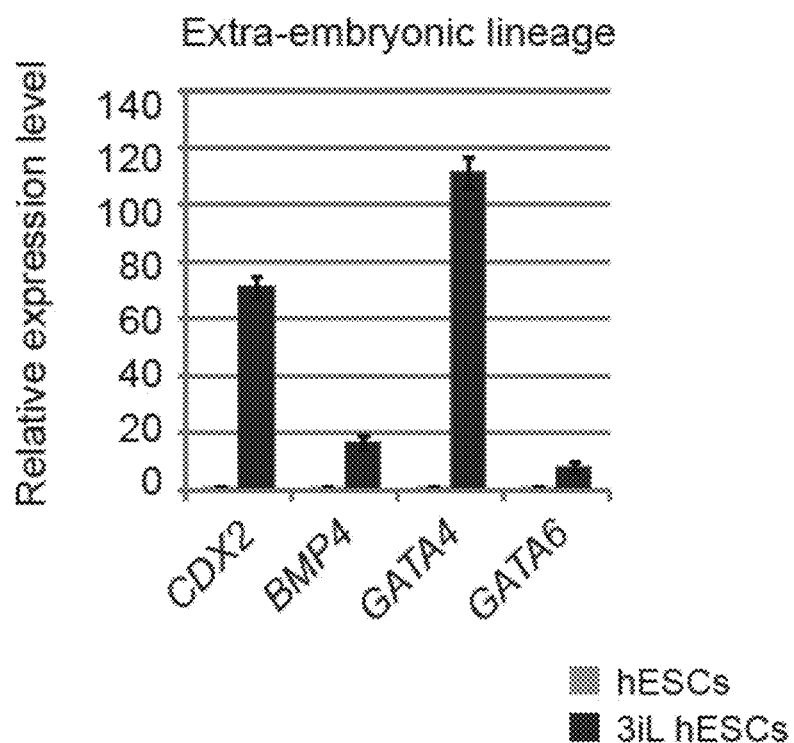
Figure 13:
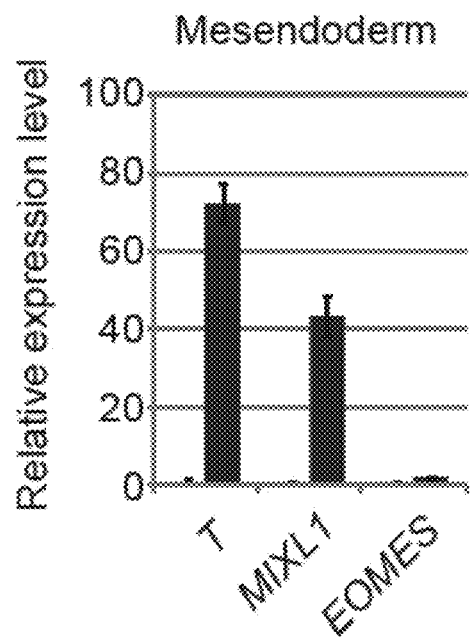
Figure 13:
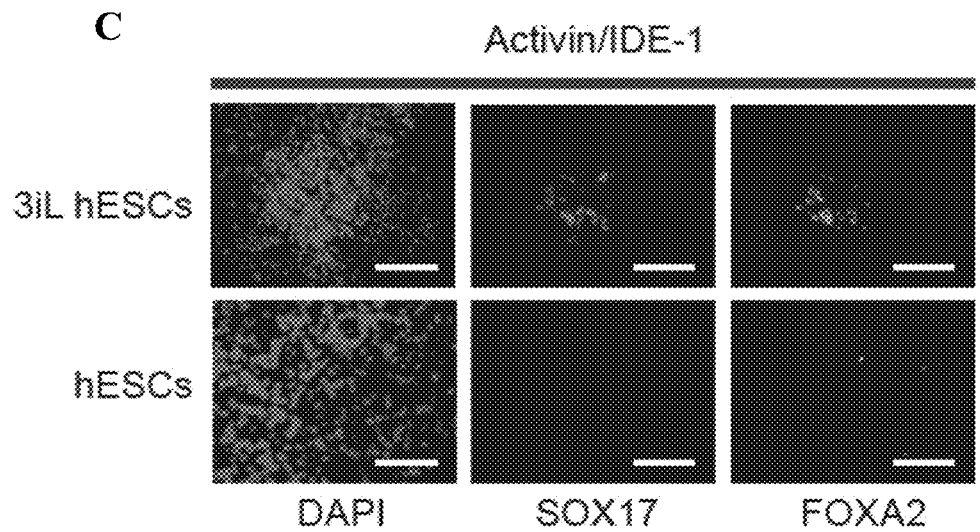
Figure 13:
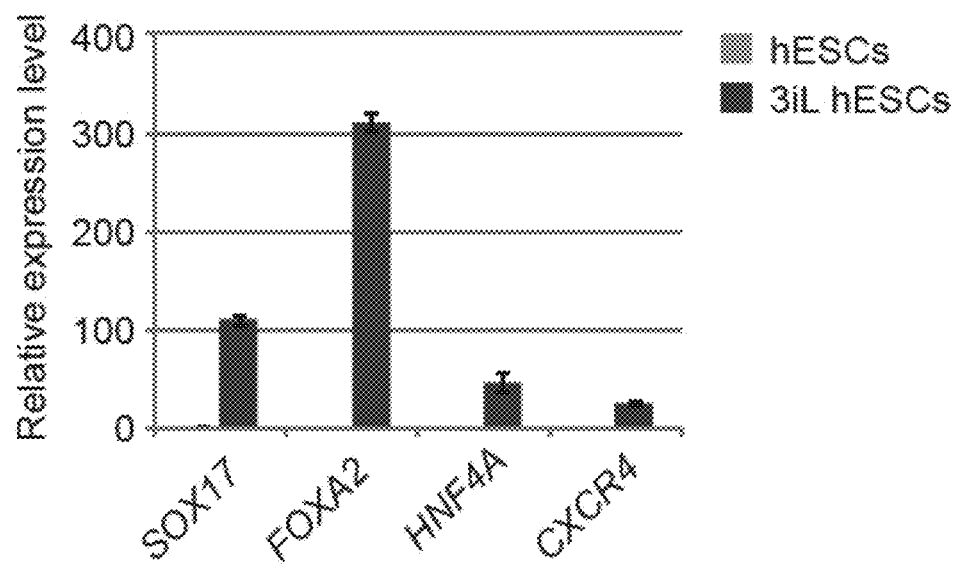
Figure 13:
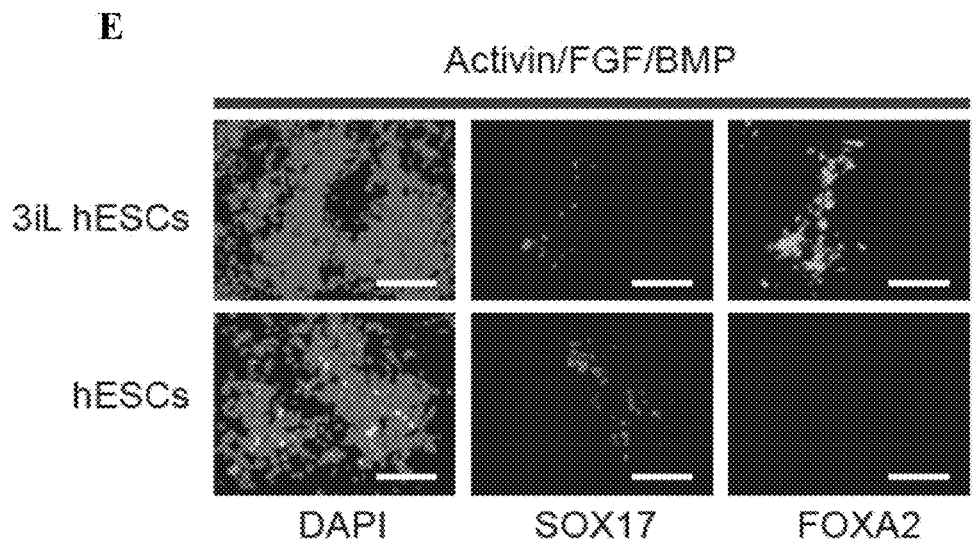
Figure 13:
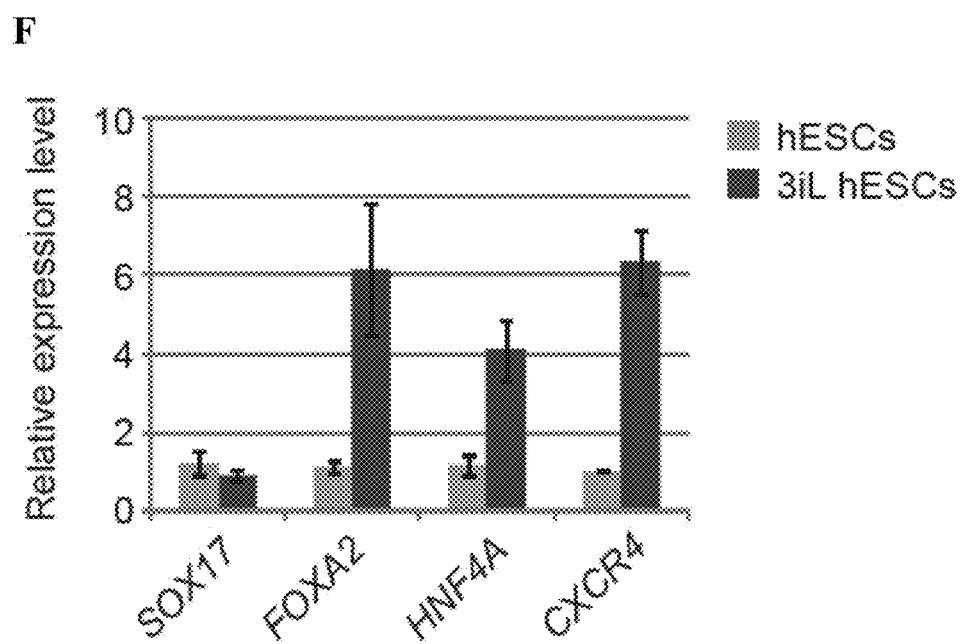

FIG. 13. Induction of developmental genes in 3iL hESCs enhances 3iL hESCs differentiation.

A) Upregulation of extra-embryonic lineage genes in 3iL hESCs. The expression of early trophoblast marker CDX2 and BMP4, and hypoblast marker GATA4 and GATA6 were upregulated in 3iL hESCs compared hESCs. All values are means±s.d from 3 independent experiments (n=3).

B) Upregulation of mesendoderm genes in 3iL hESCs. The expression of mesendoderm marker T, MIXL1 and EOMES were upregulated in 3iL hESCs compared to hESCs. All values are means±s.d from 3 independent experiments (n=3).

C) 3iL hESCs efficiently differentiate along the endoderm lineage with Activin A and IDE-1 treatment. 3iL hESCs and hESCs were seeded at similar densities on Matrigel coated dish and treated with Activin A and IDE-1 for differentiation towards the endoderm lineage. The cells were fixed at day 5 of treatment and stained for definitive endoderm markers SOX17 and FOXA2. Clusters of SOX17 and FOXA2 positive cells were detected 3iL hESCs samples whereas few cells in hESCs sample stained positive for the markers.

D) Stronger induction of endoderm markers in 3iL hESCs samples compared to hESCs samples treated with Activin A and IDE-1. Gene expression of endoderm markers SOX17, FOXA2, HNF4A and CXCR4 were much highly upregulated in 3iL hESCs samples compared to hESCs samples. All values are means±s.d from 3 independent experiments (n=3).

E) 3iL hESCs and hESCs efficiently differentiate along the endoderm lineage with Activin A/FGF2/BMP4 treatment. 3iL hESCs and hESCs seeded at similar densities on matrigel coated dish and treated with Activin A/FGF2/BMP4 for differentiation towards the endoderm lineage. The cells were fixed at day 5 of treatment and stained for definitive endoderm markers SOX17 and FOXA2. More cells in the 3iL hESCs samples express higher level of FOXA2 compared to cells in hESCs samples.

F) Stronger induction of endoderm markers in 3iL hESCs samples compared to hESCs samples treated with Activin A/FGF2/BMP4. Gene expression of endoderm markers FOXA2, HNF4A and CXCR4 were much highly upregulated in 3iL hESCs samples compared to hESCs samples. All values are means±s.d from 3 independent experiments (n=3).

DETAILED DESCRIPTION OF THE PRESENT INVENTION

In a first aspect, the present invention refers to a method for culturing and maintaining a pluripotent stem cell in an undifferentiated state comprising culturing the pluripotent stem cell in a medium comprising an MEK inhibitor, a GSK3 inhibitor, a dual inhibitor of AMPK and/or BMP signaling and LIF.

In one embodiment, the pluripotent stem cell is an induced pluripotent stem cell.

In another embodiment, the medium may be a conditioned medium.

In another embodiment, the medium may comprise feeder cells. In another embodiment, the medium may be free of feeder cells.

The pluripotent stem cell may be cultured on a matrix. The matrix may be a basement membrane matrix. In one embodiment, the matrix may be an extracellular matrix comprising one or more of laminins, collagen, gelatin, fibronectin, vitronectin, proteoglycan, entactin, heparan sulfate, synthetic biopolymers, or synthetic peptides.

The pluripotent stem cell may be an embryonic stem cell. The embryonic stem cell is preferably human. However, it will be appreciated that stem cells from other species may be suitable. For example, murine embryonic stem cells or primate embryonic stem cells may also be suitable.

The method as described herein may comprise the step of further passaging the pluripotent stem cell in an undifferentiated state.

The MEK inhibitor may be selected from the group consisting of Trametinib (GSK1120212), Selumetinib, Binimetinib or MEK162, PD-0325901, Cobimetinib or XL518, CI-1040, PD98059, PD184352, U0126 or any derivatives from these existing compounds.

The MEK inhibitor may be at a concentration of from about 0.1-5 µM, about 0.2-4 µM, about 0.3-3 µM, about 0.4-2 µM and about 0.5-1 µM. In one embodiment the MEK inhibitor may be at a concentration of from about 0.5-1 µM.

The GSK3 inhibitor may be selected from 6-bromoindirubin-3'-oxime (BIO), CHIR-99021, SB216763, CHIR-98014, TWS119, IM-12, 1-Azakenpaullone, AR-A014418, SB415286, AZD1080, AZD2858, Indirubin, and any derivatives of these compounds.

The GSK3 inhibitor may be at a concentration of about 0.5-5 µM, about 0.75-4 µM, about 0.8-3 µM, about 0.85-2 µM, about 0.9-2 µM, about 0.95-2 µM, about 1-2 µM and about 1.5-2 µM In one embodiment, the GSK3 inhibitor may be at a concentration of about 1-2 µM.

The BMP4 signaling and AMPK inhibitor may be selected from 6-[4-(2-Piperidin-1-ylethoxy)phenyl]-3-pyridin-4-ylpyrazolo[1,5-a]pyrimidine (Dorsomorphin), LDN-193189, LDN212854, K02288, A-769662, Acadesine, Phenformin and any derivatives from these compounds.

The BMP4 signaling and AMPK inhibitor may be at a concentration of about 0.5 µM about 1 µM about 1.25 µM about 1.5 µM about 1.75 µM and about 2 µM. In one embodiment, the AMPK inhibitor may be at a concentration of about 2 µM.

The LIF may be at a concentration of about 1-20 ng/ml about 2-20 ng/ml, about 2-18 ng/ml, about 3-16 ng/ml about 4-14 ng/ml about 5-12 ng/ml about 6-10 ng/ml about 7-10 ng/ml about 8-10 ng/ml. In one embodiment, the LIF may be at a concentration of about 8-10 ng/ml.

The medium comprising an MEK inhibitor, a GSK3 inhibitor, a dual inhibitor of AMPK and/or BMP signaling and LIF may further comprise epigenetic modifiers, for example, epigenetic inhibitors. Epigenetic inhibitors include but are not limited to DNA methyltransferase inhibitors and histone deacetylase (HDAC) inhibitors, for example, RG108, BIX, DNZEP, valproic acid, Sodium Butyrate and 5-aza-2'-deoxycytidine.

In another aspect, there is provided a pluripotent stem cell produced by the method as described herein. The pluripotent stem cell produced by the method as described herein may express at least one pluripotency marker selected from the group consisting of NANOG, TRA-1-60, OCT4, TRA-1-81, SOX2, LIN28, PRDM14 AND ZFP42. In another embodiment, the pluripotent stem cell described herein may express at least one epiblast-like gene expression marker selected from the group consisting of DPPA3, KLF4, KLF5, TBX3, DNMT3L, AHNAK, ARRB1, CLEC4D, GGT5, IL6R, LIMCH1, MFAP3L, SLC25A16, SMYD2, SOAT1 and ZNF600.

In another embodiment, the pluripotent stem as described herein may express at least one extra-embryonic marker selected from the group consisting of CDX2, BMP4, GATA4 and GATA6.

In another embodiment, the pluripotent stem cell described herein may express at least one mesendoderm marker selected from T, EOMES or MIXL1.

The pluripotent stem cell as described herein may comprise an expression level of at least one marker that is increased relative to a cell that has not been cultured in accordance with the method described herein.

The expression level of the at least one marker may be determined by RNA-sequencing or real-time PCR.

In one embodiment, the expression level of the at least one marker may be increased by at least 1.5 to 5 fold relative to a cell that has not been cultured in accordance with the method as described herein.

In one embodiment, the at least one marker is NANOG and the expression level may be increased by 1.5 to 2 fold relative to a cell that has not been cultured in accordance with the method as described herein.

In one embodiment, the differentiation of the pluripotent stem cell, as described herein, into an endoderm, a neuronal or a mesoderm cell is enhanced relative to differentiation of a cell that has not been cultured in accordance with the method as described herein.

In another aspect, there is also provided a culture medium for culturing and maintaining a pluripotent stem cell in an undifferentiated state, wherein said culture medium comprises an MEK inhibitor, GSK3 inhibitor, AMPK inhibitor and LIF.

In another aspect, there is also provided a method for generating lineage specific cells from a pluripotent stem cell, comprising: a) culturing a pluripotent stem cell in an undifferentiated state according to the method as described herein; b) isolating the undifferentiated pluripotent stem cell; and c) culturing the isolated undifferentiated pluripotent stem cell in a culture medium suitable to differentiate the isolated pluripotent stem cell into lineage specific cell.

In one embodiment, the lineage specific cells may be somatic cells or organoids. In another embodiment, the lineage specific cells may be endoderm lineage cells.

In another embodiment, the somatic cell may be a committed progenitor cell capable of self-renewal or differentiation into one or several somatic lineages, or a fully mature somatic differentiated cell.

In another aspect there is provided, a kit when used in the method as described herein, for culturing and maintaining a pluripotent stem cell in an undifferentiated state comprising a culture medium as described herein and instructions for use.

Experimental Section

Materials and Methods
Cell Culture

The hESC line H1 (WA-01, passage 28) was used for this study. For routine culture of hESCs in TeSR1 (Stem cell technologies), cells were cultured feeder free on matrigel (BD). Cell media was changed daily. The hESCs were subcultured with 1 mg/ml Dispase (Stem cell technologies) every 5-7 days. 3iL hESCs culture medium contains 1 µM of PD0325901 (Sigma), 2 µM of BIO (Sigma), 2 µM of Dorsomorphin (Sigma) and 10 ng/ml human LIF (Millipore) in TeSR1. 3iL media are prepared fresh and stored at 4° C. for not more than 2 weeks. For treatment with 3iL conditions, hESCs cultured in TeSR1 was treated with 3iL 48 hrs post-seeding. The cells are subsequently subcultured on mitomycin C inactivated mouse fibroblast. Cells are dissociated to single cells using TrypLE (Life Technologies). 3iL medium is refreshed daily and cells are subcultured upon confluency. ROCK inhibitor Thiazovivin is added at a final concentration of 1 µM to enhance cell survival for the first few passages. 3iL hESCs used in all the experiments have been cultured for at least 10 passages for adequate conditioning to the new culture condition.

Small Molecule Compounds Treatment hESCs were dissociated with dispase and treatment starts 48 hrs post seeding. For single chemical and combinatorial chemical treatment, the small molecules are used at the following final concentrations: 0.5 µM A83-01 (Stemgent), 2 µM BIO (Sigma), 3 µM CHIR99021 (Stemgent), 2 µM Dorsomorphin (Sigma), 8 µM Forskolin (Stemgent), 2 µM IDE-1 (Stemgent), 0.5 µM PD153035 (Sigma), 1 µM PD173074 (Sigma), 1 µM PD0325901 (Sigma), 5 µM Pifithrin-α (Sigma) and 1 µM RepSox (Sigma). All small molecules are reconstituted in DMSO. For PI3K pathway inhibition, LY294002 (Sigma) was used at final concentration of 10 µM.

RNA Extraction, Reverse Transcription, Quantitative Real-Time PCR and RNA-Sequencing (RNA-Seq) Preparation For expression analysis, total RNA was extracted using the TRIzol reagent (Invitrogen) with chloroform and precipitated with isopropanol. The precipitated RNA was centrifuged at 13000 rpm at 4° C. for 10 min. The RNA pellet was washed with 70% ethanol and subsequently reconstituted with DEPC-treated water (AMBION). DNA contaminants were digested with DNASE I (Ambion) at 37° C. for 30 min. The DNASE I enzyme is heat inactivated at 70° C. for 10 min. RNA concentration was determined with the NanoDrop 2000 (Thermo Scientific). 500 ng of RNA was used for each reverse transcription reaction using the SuperScript II Kit (Invitrogen) to produce the cDNA for subsequent quantitative assays. Quantitative real-time PCR (qPCR) analysis was performed with the SYBR Green Master Mix (KAPA) using the ABI PRISM 7900 sequence detection system. For RNA-Seq library preparation, the total RNA was further purified by column (Purelink RNA Mini kit, Ambion). RNA-Seq libraries were prepared using 4 ug of total RNA according to manufacturer's (TruSeq RNA Sample Preparation Kit v2, Illumina). Briefly, mRNA was obtained using two rounds of purification with poly-T oligo-attached magnetic beads. The mRNA was then fragmented and subjected to the first strand and second strand cDNA synthesis, then end-repaired, adenylated, adaptor ligated and finally subjected to 15 cycles of PCR. Samples were multiplexed and sequenced single read 76 bp (HiSeq 2000, Illumina).

Chromatin Immunoprecipitation

Chromatin immunoprecipitation (ChIP) was performed as previously described (Karwacki-Neisius et al., 2013). Briefly, cells were fixed with 1% formaldehyde for 10 min at room temperature, and formaldehyde was inactivated by the addition of glycine to a final concentration of 0.2 M. Cell lysates were sonicated and chromatin extracts were immunoprecipitated overnight at 4° C. using Protein G Dynal Magnetic Beads that have been coupled with antibodies against Oct4 (abcam ab19857), Nanog (R&D AF1997), STAT3 (Cell Signaling 9145), p300 (Santa cruz sc585), H3K4me3 (Millipore 04-745), H3K27ac (abcam ab4729) or H3K27me3 (Millipore 07-449). Chromatin immunoprecipitation sequencing (ChIP-Seq) library was prepared using the NEBNext® ChIP-Seq Library kit (NEB Biolabs) according to the manufacturer's instructions and sequenced with the HiSeq 2000 system (Illumina).

Single-Cell Gene Expression Analysis

Single-cell gene expression data were collected following the Single-Cell Gene Expression Using SsoFast EvaGreen SuperMix with Low ROX on the Biomark System Advanced Development Protocol 41. Briefly, hESCs and 3iL-cultured hESCs were sorted directly with the BD FACSAria II (BD Bioscience) into 96-well PCR plates loaded with the reverse transcription-specific target amplification solution (Life Technologies). Reverse transcription, 20-cycle pre-amplification and exonuclease 1 (NEB) treatment were performed prior to 7-fold dilution of pre-amplified products. Amplified single-cell samples were analyzed with 2× SsoFast EvaGreen Supermix with Low ROX (Bio-Rad) and individual qPCR primers using 48×48 Dynamic Arrays on a Biomark System (Fluidigm). Threshold crossing (Ct) values were calculated using the BioMark Real-Time PCR Analysis software (Fluidigm).

In Vitro Differentiation

For spontaneous differentiation through embryoid body formation, 3iL hESCs were dissociated by TrypLE and cultured in suspension in low attachment 10 cm dishes. After 2-3 weeks, embryoid bodies were transferred to gelatin-coated plates and cultured for another 6 days. For growth factor induced differentiation, cells were seeded onto matrigel and treated with the respective medium for differentiation along different lineages; 100 ng/ml Activin A in advanced RPMI medium (GIBCO) containing 2% FBS (GIBCO) for definitive endoderm differentiation, 100 ng/ml BMP4 and 4 ng/ml bFGF in F12 DMEM (GIBCO) containing 20% KSR (GIBCO) for mesoderm differentiation, 100 ng/ml BMP4 and 1 µM PD0325901 in F12 DMEM (GIBCO) containing 20% KSR (GIBCO) for trophectoderm differentiation, and 10 µM SB431542 and 2 µM Dorsomorphin in neural basal medium supplemented with 0.5× N2 and B27 supplements for neural ectoderm differentiation.

Teratoma Formation hESCs cultured in standard media or 3iL hESCs were dissociated with TrypLE and resuspended in 30% matrigel/F12 DMEM (GIBCO) at a concentration of $1\times10^7$ cells/ml. Rock inhibitor Thiazovivin (Stemgent) was added to hESCs culture in standard media at a final concentration of 0.5 µM. 200 µl of the cell suspension was injected into the dorsal flanks of SCID mice that were anesthetized with Avertin. Teratomas were formed after 6 to 8 weeks and they were surgically dissected, fixed in Bouin's solution and embedded in paraffin. They were sectioned and analyzed with Mallory's Tetrachrome staining.

Western Blot Analysis hESCs were lysed with a lysis buffer (50 mM Tris-HCl, pH 8.0, 150 mM NaCl, 10 µM ZnCl, 0.5% Nonidet P-40, 5% glycerol) supplemented with protease inhibitor cocktail (Merck). Protein concentration was measured with a Bradford assay kit (Bio-Rad). 50 µg of cell lysate was resolved on a 10% SDS-polyacrylamide gel and transferred to a polyvinylidine difluoride membrane (Millipore). The membrane was blocked with 5% skim milk dissolved in PBS containing 0.1% Tween20 (0.1% PBST). After blocking, the blot was incubated with either anti-OCT4 (Abcam), anti-NANOG (R&D), GP130 (Santa Cruz), anti-STAT3 (Cell signaling), anti-Phospho Tyr705 STAT3 (Cell signaling) or anti-GAPDH (Santa-Cruz) primary antibodies overnight, washed with 0.1% PBST and incubated with either horseradish peroxidase (HRP)-conjugated anti-rabbit IgG (Santa Cruz) or HRP-conjugated anti-goat IgG (Santa Cruz) respectively. After washing with PBST, signals were detected using the Western Blotting Luminol Reagents (Santa Cruz).

Immunofluorescence Staining hESCs or differentiation culture were fixed with 4% paraformaldehyde in PBS. After permeablization in 1% Triton X-100/PBS for 30 min, immunostaining was performed using the following primary antibodies: NANOG (R&D system), OCT4 (Abcam), TRA-1-60 (Santa Cruz), TRA-1-81 (Santa Cruz), PAX6 (Covance), GATA4 (Santa Cruz), SOX17 (abcam), p57kip2 (Neomarkers). Secondary antibodies used were Alexa Fluor 488/546 anti-mouse IgM, Alexa Fluor 488/546 anti goat IgG and Alexa Fluor 488/546 anti-mouse or anti-rabbit IgG (Invitrogen). DAPI or Hoechst (Invitrogen) was used for staining the nuclei.

Flow Cytometry Analysis of Immunostained Cells

Cells cultured in 3iL or standard media were harvested and fixed in 80% ethanol overnight. Cells were lysed in 200 µl 0.5% TritonX-100 PBS solution on ice for 10 min. After that, cells were block in 1% BSA and stained with antibodies against TRA-1-60 (Santa Cruz), TRA-1-81 (Santa Cruz), NANOG (R&D) or OCT4 (Abcam) on ice for 2 hrs. Cells were washed three times before and after secondary antibody staining. Secondary antibody staining alone was used as isotype control. Cells were analyzed on BD LSR II Flow Cytometer System. Data collected were analyzed by FlowJo vx.

Karyotyping

Cells were treated with colcemid for mitotic arrest and harvested by standard hypotonic treatment and methanol:acetic acid (3:1) fixation. Slides were prepared by standard air drying method and G-band karyotyping was performed.

Bioinformatics Analysis

RNA-Seq reads were mapped to the human genome assembly hg19 using TopHat2 version 2.0.9 with parameter-b2—very-sensitive, we also used the -GTF option with transcriptome annotations from Ensembl (GRCh37.69). Differential expression was estimated using cuffdiff version 2.1.1. The cuffdiff test statistic was used to rank genes for the gene set enrichment analysis. Expression data for the individual samples was estimated using cufflinks version 2.1.1 with options -b, -multi-read-correct, -g, repeatMasker annotation were used to mask rRNA, tRNA, snRNA and srpRNA genes. Single cell RNA-Seq expression data from preimplantation human embryos was downloaded, merged with 3iL and Tesr RNA-Seq data, and then quantile normalized. Expression values for every gene in every sample were further divided by the sum of the gene's expression. Differences in average expression for FIG. 4B were calculated using the multtest package, the test statistic is from a t-test, p-values are multiple testing corrected. Genes in FIG. 4C were further normalized on the subset of genes and samples. For visualization of RNA-Seq data at specific genomic loci, reads were normalized by the number of mapped reads.

ChIP-Seq reads were mapped against the hg19 reference genome using Bowtie (0.12.5), peak calling was done with MACS (1.4.0). Peaks were associated with the nearest TSS. Reads were counted in a 4 kb window around the transcription start site for all coding genes which are currently annotated (Ensembl version 69, total number: 19,978). In the case of multiple TSSs, only the TSS with the maximum number of PolII ChIP-Seq reads were selected, assuming that this represents the primary TSS for the respective genes in hESCs. The log-fold change for histone modifications and transcription factor occupancy was calculated using DESeq2. GSEA plots for ChIP-Seq data were created using the top 1000 loci with the strongest fold change between 3iL hESCs and hESCs. Box plots were generated in R using standard settings. All bioinformatics analyses were carried out using R version 3.0 and Bioconductor version 2.12.

Accession Numbers

RNA-Seq and ChIP-Seq data are available in the Array-Express database (www.ebi.ac.uk/arrayexpress) under accession numbers E-MTAB-2031 (RNA-Seq), E-MTAB-2041 (histone modifications), MTAB-2042 (STAT3) and E-MTAB-2044 (OCT4, NANOG, p300, input control).

EXAMPLES

Example 1

A Combination of Small Molecules Induces a Unique hESC State

To induce an alternative hESC state that is potentially closer to the in vivo pre-implantation epiblast state, 11 small molecules that target 8 signaling pathways were used to screen for conditions that increase the expression of NANOG (FIG. 1A). NANOG serves as a deterministic marker in the segregation of pluripotent epiblast from the hypoblast in the inner cell mass of pre-implantation embryos. The level of Nanog in mouse blastocyst is decreased during implantation, suggesting that the Nanog levels reflect different states of pluripotency. The expression of NANOG is also enriched in the human native pre-implantation epiblast compared to hESCs. The influence of these inhibitors was first investigated individually. Although the cells treated with most of the small molecules stained positive for hESC markers, they did not exhibit a change in either their morphology or induce the upregulation of the NANOG transcript (FIG. 1B-C). Therefore combinations of these molecules were then used (FIG. 1D). In contrast to the usage of individual molecules, the treatment with several combinations resulted in changes in both hESC morphology and upregulation of NANOG (FIG. 2A, FIG. 1E). In particular, combinations 21, 22, 23 and 24 induced a 1.5-2.0 fold increase in NANOG transcripts. The POU5F1 levels remained largely unchanged in these combinations (FIG. 2A), suggesting that these cells are still pluripotent.

Next, chemical combinations 21 to 24 were investigated to determine if they can stably sustain hESC self-renewal. However, a strong impairment in proliferation for 3 of the conditions was observed, such that few colonies survived after the first passage. Only hESCs treated with combination 22, (PD03/BIO/DOR, herein referred to as 3i) were able to form small, compact colonies on mouse fibroblast feeders (FIG. 2B). However, the number of colonies decreased in each subsequent passage indicating that self-renewal is disrupted (FIG. 2C-D). As the morphology of these cells resembles that of mouse embryonic stem cells (mESCs), it was investigated if the activation of signaling pathways that promote the self-renewal of mESCs can improve cell survival. LIF signaling is a key signaling pathway in the maintenance of mESCs, the ICM, and the conversion between mouse pluripotent states. Strikingly, the addition of LIF could rescue the impaired self-renewal of 3i hESCs and enabled these cells to be stably propagated for more than 30 passages (FIG. 2C-D). These 3i+LIF treated hESCs (herein referred to as 3iL hESCs) form smaller and more compact colonies compared to hESCs cultured in TeSR1 media (herein referred to hESCs) (FIG. 2E). In contrast to hESCs, 3iL hESCs can survive the passage as single cells without the addition of ROCK inhibitor (FIG. 2F). The combinatorial use of the 3 inhibitors is important to maintain the 3iL hESC state as the cells cannot be maintained when individual chemicals are removed from the media (FIG. 1G). In summary, the application of 3 inhibitors and LIF enables the efficient propagation of hESCs which are distinct from conventional hESCs.

Example 2

Active LIF Signaling in 3iL hESCs

In contrast to conventional hESCs which do not depend on LIF signaling, LIF appears to be essential for the self-renewal of 3iL hESCs. To further investigate the role of LIF in 3iL hESCs, a Jak inhibitor (inh) that targets the LIF signaling pathway was used. Treatment of 3iL hESCs with the Jak inh induced a decrease in pluripotency marker expression and a strong reduction in colony numbers (FIG. 3A-B). Gene expression of NANOG and LIF signaling responsive genes KLF4 and SOCS were reduced (FIG. 3C). These results further indicate that LIF signaling is required for the maintenance of hESCs.

LIF signaling can be induced in hESCs. However, in contrast to 3iL hESCs, LIF is not essential for hESC self-renewal. To investigate the cause of the difference in LIF requirement, the LIF signaling activity in both cell states was compared. In hESCs, the transcript of GP130, which is the co-receptor essential for LIF activity, is poorly expressed compared to other components of the LIF signaling pathway (FIG. 3D). The short treatment of hESCs with 3i and the stable culture of hESCs in 3iL both resulted in the upregulation of GP130 transcript (FIGS. 3E-F) and protein levels (FIG. 3G), indicating that these cells have become more sensitive to LIF signaling. Correspondingly, the level of phosphorylated STAT3 was also significantly higher in 3iL hESCs compared to hESCs that were cultured with LIF alone (FIG. 3H), suggesting that LIF signaling is more active in 3iL hESCs. The expression levels of known STAT3 targets SOCS3 and KLF4 were also increased in hESCs treated with 3i+LIF compared to LIF alone (FIG. 3I). Interestingly, NANOG expression levels increased with the addition of LIF in a dosage dependent manner under 3i treatment, suggesting that NANOG might be a direct target of LIF signaling (FIG. 4A). These results indicate that while 3i treatment could not sustain the hESCs self-renewal, it induces a hESC state which is highly responsive to LIF signaling. The elevated LIF signaling becomes essential for the maintenance of the pluripotent cell state under the 3i culture condition.

Next it was investigated if other signaling pathways important in hESCs also play a role in 3iL hESCs. The FGF, PI3K and Activin signaling pathways have been reported to play an important role in the maintenance of hESCs. 3iL hESCs were treated with the respective small molecule inhibitors of these three signaling pathways and also of EGF signaling which has not been reported to play a role in hESCs as a negative control. The inhibition of FGF, PI3K and Activin signaling pathways resulted in the loss of pluripotency markers after 10 days of treatment (FIG. 4B-C). This result suggests that other signaling pathways are still required to act in conjunction with the LIF signaling pathway to support the unique 3iL hESC state.

Example 3

3iL hESCs Exhibit Hallmarks of Pluripotency

Characterization to determine if these 3iL hESCs are indeed pluripotent followed. The cells stained positive for pluripotency markers OCT4, NANOG, TRA-1-60 and TRA-1-81 (FIG. 5A). The transcript levels of the pluripotency markers remained comparable between 3iL hESCs and untreated hESCs (FIG. 5B). 3iL hESCs maintained a 2-fold higher level of NANOG expression (FIG. 5B) which was also reflected at the protein level (FIG. 5C). Interestingly, an upregulation of epiblast-specific genes was observed including DPPA3, and TBX3 in 3iL hESCs (FIG. 5B). Fluorescence activated cell sorting (FACS) analysis reveals that 3iL hESCs clearly expressed OCT4, and have a marked increase in NANOG, TRA-1-60 and TRA-1-80 levels (FIG. 5D).

Next, it was investigated if the 3iL hESCs could differentiate to all germ lineages. 3iL hESCs form large embryoid bodies which can differentiate to cells of the extra-embryonic lineage and all three germ layers (FIG. 5E). In vivo, 3iL hESCs also generated tissues of all three germ lineages when injected into immunodeficient mice (FIG. 5F). Interestingly, the 3iL hESCs generated teratomas of a larger volume in a shorter time than hESCs (FIG. 5G). Importantly, 3iL hESCs maintained a normal karyotype after 2 months of culture in the 3iL condition (FIG. 5H). These results show that 3iL hESCs are indeed pluripotent. To confirm that the 3iL hESC state is not unique to H1 hESC, the 3i+LIF small molecule combination was tested on two other human hESC lines, hES2 and hES3 (FIG. 6A-L). Reproducible changes in morphology, induction of marker expression and ability to differentiate to all 3 germ layers in teratomas was observed. The 3iL condition was next tested to determine if it enables maintenance of induced pluripotent stem cells (iPSCs). The cells were treated with 3iL conditions after 3 weeks of virus induction. While an increase in total number of iPSC colonies was not observed (FIG. 6M), a significant improvement in virus silencing in these iPSC colonies was observed (FIG. 6N-O), suggesting an increase in the number of bona fide iPSC colonies. iPSC clones can also be stably cultured in 3iL conditions (FIG. 6P-R). These data confirm that the induction of a distinct cell state by 3iL is achievable across different human pluripotent cells.

Example 4

The Transcriptome of 3iL hESCs Resembles Native Pre-Implantation Epiblast

The above results indicate that 3iL hESCs are distinct from hESCs. To characterize these differences, the transcriptome of 3iL hESCs and hESCs was compared using RNA-Seq. First genes that showed significant changes in expression levels between 3iL hESCs and hESCs were identified, further referred to as 3iL hESC-specific (increased expression in 3iL hESCs) and hESC-specific genes (decreased expression 3iL hESCs). Table 1 shows a list of 3iL hESC-specific genes.

TABLE 1

| 3iL hESC-specific genes. |
|---|
| A4GALT |
| AGL |
| AHNAK |
| ANGPT2 |
| ANKRD55 |
| ANXA2 |
| ARRB1 |
| ASRGL1 |
| BBS5 |
| BMI1 |
| BMP4 |
| C17orf51 |
| C2orf18 |
| C6orf211 |
| CDA |
| CDX2 |
| CENPA |
| CFLAR |
| CLEC4D |
| CTSB |
| CYP1B1 |
| DDX43 |
| DEFA6 |
| DNAJC15 |
| DNMT3L |
| DPPA3 |
| DPPA5 |
| EOMES |
| FABP5 |
| FAM20A |
| FAM43B |
| FGF4 |
| FGF8 |
| GAD1 |
| GATA4 |
| GATA6 |
| GBX2 |
| GDF3 |
| GDPD3 |
| GGT5 |
| GLUD2 |
| GP130 |
| GPX2 |
| HERC3 |
| HHLA2 |
| HOXB7 |
| HPGD |
| IFI16 |
| IL6R |
| IL6ST |
| KLF2 |
| KLF4 |
| KLF5 |
| KLF8 |
| KLHL18 |
| KTI12 |
| LAMB1 |
| LIMCH1 |
| MFAP3L |
| NACAP1 |
| NANOG |
| NBPF15 |
| NEFH |
| NETO2 |
| NLRP2 |
| NLRP7 |
| NSMAF |
| OBFC2A |

TABLE 1-continued

3iL hESC-specific genes.

OOEP
PITX2
PMP22
PRDM1
PRDM14
PTH1R
RAB15
REST
RHOU
RIN2
S100A10
SLC25A16
SLC25A44
SLC3A2
SMPDL3A
SMYD2
SOAT1
SOCS3
SP100
T
TAGLN2
TBCA
TBX3
TCEA1
TFAP2C
TRIM61
TSPAN18
UPP1
UQCRH
WARS
WNT3
ZBTB10
ZNF600
ZNF823

Amongst the 3iL-specific genes are NANOG, DPPA3, KLF4 and TBX3 (FIG. 7A), confirming the initial observations. To investigate if 3iL hESCs resemble in vivo pluripotent cells, the 3iL hESC expression data was compared with single cell RNA-Seq data from human pre-implantation embryos and primary hESCs derived from blastocysts at passage 0 and 10. Strikingly, it was found that 3iL hESC-specific genes show significantly higher expression in pre-implantation blastocyst cells than in hESC-specific genes (FIG. 7B). In contrast, hESC-specific genes show higher expression than 3iL hESC-specific genes in primary hESC outgrowth from the blastocyst (FIG. 7B). Importantly, the set of 3iL hESC-specific and hESC-specific genes is sufficient to discriminate hESCs from pre-implantation blastocyst cells based on single cell RNA-Seq data (FIG. 7C). The ICM of the profiled blastocyst consists of cells of the pluripotent epiblast (EPI) and cells of the primitive endoderm (PE). Since the epiblast cells of the blastocyst is of particular interest, the expression of putative EPI-specific genes was assessed in 3iL hESCs. Genes which are expressed at a higher level in EPI cells compared to hESCs (epiblast-specific genes) are significantly enriched in 3iL hESCs (FIG. 7D-E, FIG. 8A-D). Increased expression of these epiblast-specific genes in 3iL hESCs is further confirmed by quantitative PCR (FIG. 7F). Single cell PCR data confirms that pluripotency genes and epiblast genes are indeed co-expressed and not a result of a heterogeneous cell population (FIG. 8E). Thus, 3iL treatment induces the conversion of hESCs towards a cellular state that more closely resembles pluripotent cells from the human pre-implantation embryo.

Example 5

Co-Expression of GATA6 and NANOG in 3iL hESCs

One of the genes which are expressed in blastocyst and 3iL hESCs but not in conventional hESCs is GATA6 (FIG. 8F). GATA6 has been reported to be able to replace OCT4 during reprogramming and is expressed in early pre-implantation embryos. As GATA6 is also implicated in primitive endoderm and mesoderm differentiation, we wanted to exclude the possibility that GATA6 expression is caused by spontaneous differentiation. Examination of the expression of pluripotency-associated genes indicated that these genes show similar expression levels in 3iL hESCs and hESCs (FIG. 8G). Validation by quantitative PCR also confirms that differentiation-associated genes are not upregulated in 3iL hESCs (FIG. 8H). The expression of GATA6 in the 3iL hESCs was further confirmed with quantitative PCR and the protein levels was further confirmed with Western blot analysis (FIG. 8I-J). Co-immunostaining of GATA6 and NANOG reveals the co-expression of these 2 proteins in 3iL hESCs (FIG. 8K). To further confirm this result, flow cytometry analysis was performed and it was found that remarkably more than 50% of the 3iL hESCs express both NANOG and GATA6 compared to less than 5% in the hESCs (FIG. 8L). GATA6 is also co-expressed with OCT4 and TRA-1-60 (FIG. 8M-N). These results indicate that expression of GATA6 is not caused by differentiation or loss of pluripotency, but rather reflects a specific property of 3iL hESCs. NANOG and GATA6 are co-expressed in cells within the ICM of the blastocyst before the segregation of the pluripotent epiblast from the hypoblast. The results suggest that 3iL hESCs potentially resemble these NANOG and GATA6 co-expressing cells. As such, 3iL hESCs could provide a model to study the role of GATA6 and other early embryo developmental genes in pluripotency.

Example 6

De-Repression of Pre-Implantation Epiblast Associated Genes in 3iL hESCs

To investigate if the gene expression profile of 3iL hESCs is stabilized by a concomitant change in the epigenetic landscape, genome-wide profiles of histone modifications associated with active (H3K27ac, H3K4me3) and repressive (H3K27me3) chromatin was generated. For every gene, a normalized fold change of the respective histone marks between 3iL hESCs and hESCs was calculated. Indeed, it was found that the change in gene expression is reflected in a global change of histone modifications at the promoters (FIG. 9A-B). Genes that show increased expression in 3iL hESCs are significantly enriched in the set of genes that show an increase of active histone modifications H3K27ac (p-value=8.83e-263) and H3K4me3 (p-value=2.38e-69), and a reduction in H3K27me3 value=4.90e-92), which is a repressive mark usually associated with developmental genes (FIG. 9B). Strikingly, when promoters of genes which are differentially expressed in the native pre-implantation epiblast and in vitro hESCs was investigated, it was found that loss of H3K27me3 occurs at epiblast-specific genes (FIG. 9C). Thus, genes which are silenced during derivation of hESCs from the blastocyst such as TBX3, KLF5, ZNF600 and HOXB cluster (FIG. 9D, FIG. 10) show re-activation in 3iL hESCs. Together these data indicate that 3iL hESCs reside in a distinct state that provides a unique model to study epigenetics of pre-implantation embryogenesis.

Example 7

A Rewired Regulatory Circuitry in 3iL hESCs

The gene regulatory network that controls pluripotency has been studied in ESCs and provided fundamental insights into the regulation of embryonic stem cell identity. These analyses on gene expression and epigenetic modifications suggest that 3iL hESCs represent a pluripotent state which is distinct from conventional hESCs. In order to investigate whether the transcriptional regulatory network is altered between both cell states, genome-wide binding maps of the master pluripotency regulators NANOG and OCT4 was generated, as well as the general enhancer binding protein P300. For every binding site of OCT4, NANOG and P300, differential binding between 3iL hESCs and conventional hESCs to identify 3iL-specific and hESC-specific binding events was calculated. Strikingly, it was found that thousands of binding events change between the two pluripotent states, indicating that the regulatory network indeed is rewired (FIG. 11A, FIGS. 12A, B and C). In support of a rewired network, it was found that transcription factor differential binding is significantly associated with differential expression of their target genes (FIG. 12A).

Since 3iL hESCs show epigenetic and transcriptional re-activation of epiblast-specific genes that are silenced in conventional hESCs, it was investigated if 3iL hESCs can be used to identify novel enhancers which are potentially active in human pre-implantation development. Indeed, it was found that the increase in NANOG occupancy at distal enhancers is Significantly associated with upregulation of epiblast specific genes (FIG. 12B) (Fisher's test p-value=5.46e-13, FIG. 12B, C). Genes which are expressed in the native pre-implantation epiblast and which show new or enhanced binding sites in 3iL hESCs include NANOG, KLF4, DPPA3, KLF5, DNMT3L, TBX3, ZNF600 and LAMB1 (FIG. 12B, C, FIG. 11B). Interestingly, STAT3 binding was detected near some of these genes (FIG. 12B, C), suggesting that LIF signaling potentially integrates with the core pluripotency network in 3iL cells (FIG. 12B, C).

In this study, it is shown that combinatorial treatment with 3 small molecules successfully induces a distinct hESC state. These 3iL hESCs require LIF to self-renew, and share an expression signature with the pluripotent epiblast cells of the native human blastocyst, cells. Single cell analysis of human pre-implantation embryos and hESCs has revealed significant differences between the two. The novel 3iL hESC state of this study narrows the gap between these in vivo and in vitro pluripotent states (FIG. 12D). The resemblance between 3iL hESCs and native pre-implantation epiblast cells provides a platform for future studies in deciphering the molecular pathways that specify pluripotency.

hESCs have been maintained in multiple chemically defined conditions using various external signaling factors, including LIF. Previous LIF dependent hESCs show similarities with the naïve state of mESCs. In contrast, 3iL hESCs, which are also LIF dependent, show similarities with the pluripotent state of native pre-implantation epiblast cells. STAT3 binding sites were observed in the rewired circuitry suggesting that LIF signaling potentially cooperates with the core transcriptional network to contribute to the 3iL hESC expression signature. LIF signaling has been reported to enhance the formation of human blastocysts in vitro. However, how LIF signaling could play a role in pluripotent cells of the blastocyst remains unknown. Hence, dissecting the role of LIF in 3iL hESCs could provide a better understanding of how LIF signaling contributes to blastocyst development.

One of the hallmarks of 3iL hESCs is the upregulation of a group of genes that are expressed in early human embryogenesis, some of which are thought to act as lineage specifiers. An example for this is GATA6, which is expressed in the early ICM of both mouse and human embryos. Interestingly, GATA3, GATA4 and GATA6 were able to replace OCT4 in reprogramming, indicating a role of lineage specifiers in pluripotency. Although the GATA6 locus is bound by OCT4, NANOG and STAT3, the role of GATA6 in 3iL hESC remains to be studied. In the 3iL hESCs, GATA6 could be a component of the pluripotency network through interaction with the core pluripotency-associated transcription factors. Alternatively, GATA6 could mark genes that will be induced during lineage-specific differentiation. The 3iL hESCs might therefore be used as a paradigm to understand the interplay between pluripotency-associated transcription factors and lineage specifiers.

Although it was shown that 3iL induces profound transcriptional and epigenetic changes in hESCs, the mechanism for this conversion is not completely understood. The data from this study demonstrates that 3iL can induce the expression of GP130, which appears to be one of the rate limiting factors for the activation of LIF signaling in hESCs. It is also conceivable that 3iL, through modulation of cellular signaling, can alter the binding of pluripotency-associated transcription factors by creating new sites. Indeed, it was observed that many new binding sites occur in 3iL hESCs, and these are significantly associated with a change in expression (FIG. 12A-C). Thus, a re-wiring of the regulatory network in response to treatment with 3i and LIF appears to be involved in the cell state conversion.

Since regulatory genomic studies require a large number of cells which are unavailable for human embryos, 3iL hESCs can serve as a system to study gene regulation of pluripotency in the blastocyst. Using ChIP-seq profiling of chromatin marks and transcription factor binding sites, many previously unknown enhancers of genes which are expressed in human blastocysts but repressed in hESCs were identified, demonstrating that 3iL hESCs provide insights into functions which have been inaccessible prior to this study. Besides gene regulation, epigenetic properties also differ between 3iL hESCs and hESCs. For example, a global de-repression of genes which are expressed in cells from human pre-implantation embryos was observed and it was found that several epigenetic regulators such as DNMT3L are differentially expressed. DNMT3L regulates DNA methylation, one of the key processes during early embryonic development. 3iL hESCs may serve as a model system to study these epigenetic pathways and their roles in the regulation of pluripotency.

In conclusion, it is found that treatment of hESCs with 3iL induces a pluripotent state that is epigenetically, transcriptionally, and morphologically distinct from conventional hESCs. It is demonstrated that a rewired regulatory circuitry in 3iL hESCs supports a native pre-implantation epiblast-like expression signature. The more native state of 3iL hESCs presents new opportunities. Thus, the study of 3iL hESCs raises numerous possibilities to revise and extend our understanding of pluripotency of human cells.

Example 8

Induction of Developmental Genes in 3iL hESCs Enhances 3iL hESCs Differentiation A strong upregulation of extra-embryonic lineage specifiers CDX2, GATA4 and GATA6, and mesendoderm marker T and MIXL was observed in 3iL hESCs (FIGS. 13A and 13B). At the same time, pluripotency associated genes show similar levels of expression in 3iL hESCs and hESCs (FIG. 8G), indicating that this is not caused by differentiation or loss of pluripotency, but rather reflects a specific property of 3iL hESCs.

The maintenance of a pluripotent state despite an increased expression of developmental genes is surprising. Investigation to determine if the expression of these developmental genes could biologically prime the cells for differentiation followed. To test this hypothesis, the endoderm differentiation efficiency of 3iL hESCs was compared with hESCs, using two endoderm differentiation protocols. In the first protocol, hESCs were differentiated using the small molecule inhibitor IDE-1 and Activin A. When 3iL hESCs were used, more cells which stain positively for the endoderm markers SOX17 and FOXA2 was observed compared to cells differentiated from hESCs (FIG. 13C). Correspondingly, there is a stronger upregulation of endoderm gene SOX17, FOXA2, HNF4A and CXCR4 in cells differentiated from 3iL hESCs (FIG. 13D). Using the second differentiation protocol, a strong induction of endoderm progenitor marker SOX17 expression was observed in most cells differentiated from 3iL hESCs and hESCs (FIG. 13E). However, more cells stained positive for the endoderm progenitor marker FOXA2 when 3iL hESCs were used (FIG. 13E). There is also stronger upregulation of the endoderm genes HNF4A and CXCR4 in cells differentiated from 3iL hESCs (FIG. 13F). Thus, 3iL hESCs appear to differentiate more easily towards endoderm lineage.

The invention claimed is:

1. A method for culturing and maintaining a pluripotent stem cell in an undifferentiated state comprising culturing the pluripotent stem cell in a medium comprising an MEK inhibitor, a GSK3 inhibitor, a dual inhibitor of AMPK and/or BMP signaling and LIF; wherein the MEK inhibitor is PD0325901 in a concentration of 0.5-1 µM, wherein the GSK3 inhibitor is BIO in a concentration of 1-2 µM, wherein the dual inhibitor of AMPK and/or BMP signaling is dorsomorphin in a concentration of 2 µM and wherein LIF is in a concentration of 8-10 ng/ml.

2. The method of claim 1, wherein the medium is selected from the group consisting of:
   a conditioned medium;
   a medium comprising feeder cells; and
   a medium free of feeder cells.

3. The method of claim 1, wherein the pluripotent stem cell is cultured on a matrix.

4. The method of claim 1, wherein the pluripotent stem cell is an embryonic stem cell.

5. The method of claim 1, wherein the PD032591 is in a concentration of 1 µM.

6. The method of claim 1, wherein the BIO is at a concentration of 2 µM.

7. The method of claim 1, wherein the dorsomorphin is at a concentration of 2 µM.

8. The method of claim 1, wherein the LIF is at a concentration of 8-10 ng/ml.

9. The method of claim 3, wherein the matrix is a basement membrane matrix or an extracellular matrix comprising one or more of laminin, collagen, gelatin, fibronectin, proteoglycan, entactin, heparan sulfate, or synthetic biopolymers.

10. The method of claim 4, wherein the embryonic stem cell is human.

* * * * *